United States Patent
Gelman et al.

(10) Patent No.: US 11,466,018 B2
(45) Date of Patent: *Oct. 11, 2022

(54) TGF-β INHIBITORS

(71) Applicant: Rigel Pharmaceuticals, Inc., South San Francisco, CA (US)

(72) Inventors: Marina Gelman, San Francisco, CA (US); Todd Kinsella, Redwood City, CA (US); Somasekhar Bhamidipati, Foster City, CA (US); Ihab Darwish, San Carlos, CA (US); Rajinder Singh, Belmont, CA (US); Jiaxin Yu, San Carlos, CA (US)

(73) Assignee: Rigel Pharmaceuticals, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/087,459

(22) Filed: Nov. 2, 2020

(65) Prior Publication Data

US 2021/0130361 A1 May 6, 2021

Related U.S. Application Data

(63) Continuation of application No. 15/563,075, filed as application No. PCT/US2016/024840 on Mar. 30, 2016, now Pat. No. 10,822,337.

(60) Provisional application No. 62/141,511, filed on Apr. 1, 2015.

(51) Int. Cl.
| | | |
|---|---|---|
| C07D 487/04 | (2006.01) |
| C07D 401/04 | (2006.01) |
| C07D 403/04 | (2006.01) |
| C07D 417/04 | (2006.01) |
| C07D 471/04 | (2006.01) |
| C07D 519/00 | (2006.01) |

(52) U.S. Cl.
CPC ......... *C07D 487/04* (2013.01); *C07D 401/04* (2013.01); *C07D 403/04* (2013.01); *C07D 417/04* (2013.01); *C07D 471/04* (2013.01); *C07D 519/00* (2013.01)

(58) Field of Classification Search
CPC .. C07D 487/04; C07D 401/04; C07D 403/04; C07D 417/04; C07D 471/04; C07D 519/00

See application file for complete search history.

(56) References Cited

U.S. PATENT DOCUMENTS

| | | | |
|---|---|---|---|
| 6,958,354 B2 | 10/2005 | Munchhof et al. |
| 7,074,801 B1 | 7/2006 | Yoshida et al. |
| 7,087,626 B2 | 8/2006 | Beight et al. |
| 7,151,110 B2 | 12/2006 | Munchhof et al. |
| 7,265,225 B2 | 9/2007 | Beight et al. |
| 7,365,066 B2 | 4/2008 | Beight et al. |
| 7,405,299 B2 | 7/2008 | Beight et al. |
| 7,834,029 B2 | 11/2010 | Beight et al. |
| 10,822,337 B2* | 11/2020 | Gelman ................ A61P 19/00 |

FOREIGN PATENT DOCUMENTS

| | | |
|---|---|---|
| EP | 1916240 | 4/2008 |
| WO | WO 2002/062787 | 8/2002 |
| WO | WO 2002/094833 | 11/2002 |
| WO | WO 2003/049542 | 6/2003 |
| WO | WO 2004/014900 | 2/2004 |
| WO | WO 2004/026302 | 4/2004 |
| WO | WO 2004/026306 | 4/2004 |
| WO | WO 2004/026871 | 4/2004 |
| WO | WO 2004/048381 | 6/2004 |
| WO | WO 2004/048382 | 6/2004 |
| WO | WO 2004/048383 | 6/2004 |
| WO | WO 2004/050659 | 6/2004 |
| WO | WO 2004/072033 | 8/2004 |
| WO | WO 2009/005675 | 1/2009 |

(Continued)

OTHER PUBLICATIONS

Tenora et al., "Application of Pd-Catalyzed Cross-Coupling Reactions in the Synthesis of 5,5-Dimethyl-5, 6-:lihydro-4H-pyrrolo[1,2-b]pyrazoles that Inhibit ALK5 Kinase," *The Journal of Organic Chemistry*, 2016, 81, 11841-11856.

(Continued)

*Primary Examiner* — Rebecca L Anderson
(74) *Attorney, Agent, or Firm* — Klarquist Sparkman, LLP

(57) ABSTRACT

Disclosed are pyrazole compounds, as well as pharmaceutical compositions and methods of use thereof. One embodiment is a compound having the structure

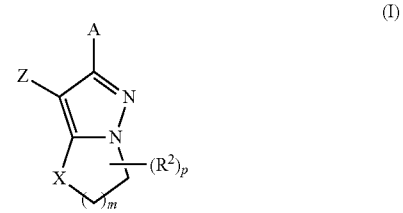

(I)

and pharmaceutically acceptable salts, prodrugs and N-oxides thereof (and solvates and hydrates thereof), wherein A, X, Z, m, p, and $R^2$ are as described herein. In certain embodiments, a compound disclosed herein inhibits the activity of one or more members of the TGF-β superfamily, and can be used to treat disease by blocking such activity.

16 Claims, No Drawings

(56) References Cited

FOREIGN PATENT DOCUMENTS

| | | |
|---|---|---|
| WO | WO 2009/076440 | 6/2009 |
| WO | WO 2010/010154 | 1/2010 |
| WO | WO 2015/195880 | 12/2015 |

OTHER PUBLICATIONS

International Search Report and Written Opinion dated Aug. 3, 2017 for International Application No. PCT/US2016/024840 filed Mar. 30, 2016, 17 pages.

* cited by examiner

TGF-β INHIBITORS

CROSS REFERENCE TO RELATED APPLICATIONS

This application is a continuation of U.S. application Ser. No. 15/563,075, filed Sep. 29, 2017, which is a U.S. national phase application under 35 USC 371 of International Patent Application No. PCT/US2016/024840, filed Mar. 30, 2016, which claims the benefit of U.S. Provisional Patent Application No. 62/141,511, filed Apr. 1, 2015.

BACKGROUND OF DISCLOSURE

Field of Invention

This invention relates to the field of compounds, pharmaceutical compositions comprising them, and methods of using the compounds and compositions. This invention relates more particularly to the field of pyrazole compounds and pharmaceutical compositions thereof, methods of inhibiting TGF-β receptor signaling with the compounds, and methods of treating and/or preventing disease with the compounds.

Technical Background

Growth and Differentiation Factor-8 (GDF-8), also known as myostatin, and TGF-β1 are members of the Transforming Growth Factor-beta (TGF-β) superfamily of structurally related growth factors, all of which possess physiologically important growth-regulatory and morphogenetic properties (Kingsley et al. (1994) Genes Dev., 8: 133-46; Hoodless et al. (1998) Curr. Topics Microbiol. Immunol., 228: 235-72). For example, activation of TGF-β1 signaling and expansion of extracellular matrix are early and persistent contributors to the development and progression of fibrotic disorders, such as involved in chronic renal disease and vascular disease. Border W. A., et al, N. Engl. J. Med., 1994; 331(19), 1286-92. GDF-8 is a negative regulator of skeletal muscle mass. For example, GDF-8 is highly expressed in the developing and adult skeletal muscle. The GDF-8 null mutation in transgenic mice is characterized by a marked hypertrophy and hyperplasia of the skeletal muscle (McPherron et al. (1997) Nature, 387: 83-90). Similar increases in skeletal muscle mass are evident in naturally occurring mutations of GDF-8 in cattle (Ashmore et al. (1974) Growth, 38: 501 507; Swatland and Kieffer (1994) J. Anim Sci., 38: 752-757; McPherron and Lee (1997) Proc. Natl. Acad. Sci. USA, 94: 12457-12461; and Kambadur et al. (1997) Genome Res., 7: 910-915). Because GDF-8 is expressed in both developing and adult muscles, it is not clear whether it regulates muscle mass during development or in adults. Recent studies have also shown that muscle wasting associated with HIV-infection in humans is accompanied by increases in GDF-8 protein expression (Gonzalez-Cadavid et al. (1998) PNAS, 95: 14938-43). In addition, GDF-8 can modulate the production of muscle-specific enzymes (e.g., creatine kinase) and modulate myoblast cell proliferation (WO 00/43781).

A number of human and animal disorders are associated with loss or functional impairment of muscle tissue, including muscular dystrophy, muscle atrophy, congestive obstructive pulmonary disease, muscle wasting syndrome, sarcopenia, and cachexia. To date, very few reliable or effective therapies exist for these disorders. However, the terrible symptoms associated with these disorders may be substantially reduced by employing therapies that increase the amount of muscle tissue in patients suffering from the disorders. While not curing the conditions, such therapies would significantly improve the quality of life for these patients and could ameliorate some of the effects of these diseases.

In addition to its growth-regulatory and morphogenetic properties in skeletal muscle, GDF-8 may also be involved in a number of other physiological processes, including glucose homeostasis in the development of type 2 diabetes and adipose tissue disorders, such as obesity. For example, GDF-8 modulates pre-adipocyte differentiation to adipocytes (Kim et al. (2001) BBRC, 281: 902-906).

There are also a number of conditions associated with a loss of bone, including osteoporosis, especially in the elderly and/or postmenopausal women. Currently available therapies for these conditions work by inhibiting bone resorption.

Like TGF-β-1, -2, and -3, the GDF-8 protein is synthesized as a precursor protein consisting of an amino-terminal propeptide and a carboxy-terminal mature domain (McPherron and Lee, (1997) Proc. Natl. Acad. Sci. USA, 94: 12457-12461). Before cleavage, the precursor GDF-8 protein forms a homodimer. The amino-terminal propeptide is then cleaved from the mature domain. The cleaved propeptide may remain noncovalently bound to the mature domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). It is believed that two GDF-8 propeptides bind to the GDF-8 mature dimer (Thies et al. (2001) Growth Factors, 18: 251-259). Due to this inactivating property, the propeptide is known as the "latency-associated peptide" (LAP), and the complex of mature domain and propeptide is commonly referred to as the "small latent complex" (Gentry and Nash (1990) Biochemistry, 29: 6851-6857; Derynck et al. (1995) Nature, 316: 701-705; and Massague (1990) Ann. Rev. Cell Biol., 12: 597-641). Other proteins are also known to bind to GDF-8 or structurally related proteins and inhibit their biological activity. Such inhibitory proteins include follistatin, and potentially, follistatin-related proteins (Gamer et al. (1999) Dev. Biol., 208: 222-232). The mature domain is believed to be active as a homodimer when the propeptide is removed.

GDF-8 is highly conserved in sequence and in function across species. The amino acid sequence of murine and human GDF-8 is identical, as is the pattern of mRNA expression (McPherron et al. (1997) Nature 387: 83-90; Gonzalez-Cadavid et al. (1998) Proc. Natl. Acad. Sci. USA 95: 14938-14943). This conservation of sequence and function suggests that inhibition of GDF-8 in humans is likely to have a similar effect to inhibition of GDF-8 in mice.

U.S. Pat. No. 7,320,789 shows that GDF-8 antibodies in mouse models can increase muscle strength (e.g., for treating sarcopenia), increase muscle mass and strength in dystrophic muscle (e.g., for treating Duchenne's muscular dystrophy), increase bone mass and bone density (e.g., for prevention and treatment of osteoporosis), augment bone healing (e.g., for treating an established muscle or bone degenerative disease (e.g., fracture repair and spine fusion, preventing the decline in bone mass, microarchitecture and strength associated with estrogen deficiency, increasing trabecular bone density), and are useful for treatment of metabolic disorders such as type 2 diabetes, impaired glucose tolerance, metabolic syndrome (e.g., syndrome X), insulin resistance induced by trauma (e.g., burns), and adipose tissue disorders (e.g., obesity).

SUMMARY

We recognized that new therapeutic agents that inhibit the activity of one or more members of the TGF-β superfamily are useful for treating human or animal disorders in which TGF-β signaling is implicated. In one aspect, such disorders include those in which immunomodulation, regulation of fibrosis and/or an increase in muscle tissue would be therapeutically beneficial, particularly oncology, fibrotic diseases, muscle and adipose tissue disorders, bone degenerative diseases, neuromuscular disorders, and diabetes.

Accordingly, the present invention comprises compounds, pharmaceutical compositions comprising them, and methods of using them to inhibit TGF-β superfamily activity both in vitro and in vivo and to treat and/or prevent disease by inhibiting TGF-β superfamily activity.

Disclosed herein are compounds having structural formula (I):

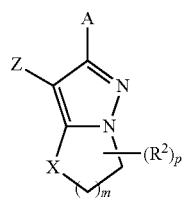

(I)

and pharmaceutically acceptable salts, prodrugs, and N-oxides thereof (and solvates and hydrates thereof), wherein A, X, Z, m, p, and $R^2$ are as described herein.

Also disclosed herein are pharmaceutical compositions. Examples of such compositions include those having at least one pharmaceutically acceptable carrier, diluent, and/or excipient together with a compound, pharmaceutically acceptable salt, prodrug, or N-oxide (or solvate or hydrate) as described herein.

Another aspect of the present invention comprises methods for treating and/or preventing disease by blocking GDF 8, TGF-0, activin, nodal or combinations thereof. Accordingly, the invention also comprises methods for treating disease using the presently disclosed compounds and pharmaceutical compositions.

Another aspect of the invention is the use of the compounds described herein to block TGF-β superfamily activity in vitro and in vivo for the purpose of studying their role in biological processes.

All publications referenced herein are incorporated by reference in their entirety to the extent they are not inconsistent with the teachings presented herein.

DETAILED DESCRIPTION

In one aspect, the invention comprises compounds that inhibit TGF-0.

In embodiment $I_1$ of this first aspect, the compounds have structural formula (I):

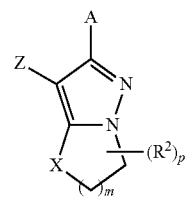

(I)

or a pharmaceutically acceptable salt, prodrug or N-oxide thereof, or solvate or hydrate thereof,
wherein
m is 1 or 2;
p is 0 or 1;
X is —$CH_2$— or —O—;
A is

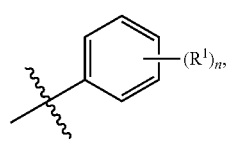

(a)

n is 0, 1, 2, 3, 4, or 5;
wherein each $R^1$ is independently halogen, —$C_1$-$C_6$alkyl, —$C_1$-$C_6$haloalkyl, —$C_1$-$C_6$alkoxy, —$C_1$-$C_6$haloalkoxy, $C_{3-8}$ Cak($C_{0-6}$ alkyl), Hca($C_{0-6}$ alkyl), Ar($C_{0-6}$ alkyl), Het($C_{0-6}$alkyl), —O—($C_0$-$C_6$alkyl)-Ar, —O—($C_0$-$C_6$alkyl)-Het, —O—($C_0$-$C_6$alkyl)-Cak, —O—($C_0$-$C_6$alkyl)-Hca, —$NO_2$, or —CN, wherein the Ar, Het, Cak, Hca, and alkyl are optionally substituted with 1, 2, 3, or 4 groups that are each independently halogen, cyano, nitro, —$OR^a$, —$SR^a$, —$NR^a_2$, —C(O)$OR^a$, —C(O)$NR^a_2$, —C(O)$R^a$, —S(O)$R^a$, —S(O)$_2R^a$, —S(O)$OR^a$, —S(O)$_2OR^a$, —S(O)$NR^a_2$, —S(O)$_2NR^a_2$, —OC(O)$R^a$, —OC(O)$OR^a$, —OC(O)$NR^a_2$, —N(R)C(O)$R^a$, —N(R)C(O)$OR^a$, —N(R)C(O)$NR^a_2$, —N(R)S(O)$R^a$, —N($R^a$)S(O)$_2R^a$, $C_1$-$C_6$alkyl, or $C_1$-$C_6$haloalkyl;
each $R^a$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano;
or

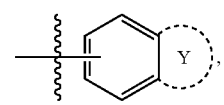

(b)

wherein the Y ring is a 5- to 9-membered Hca optionally substituted by halo or $C_1$-$C_6$alkyl;
each $R^2$ is independently halogen, $C_1$-$C_6$alkyl, $C_1$-$C_6$haloalkyl, —OR', —SR', —$NR^e_2$, $C_{3-8}$Cak, —$NO_2$ or —CN, wherein each $R^c$ is independently hydrogen, $C_1$-$C_6$alkyl, or $C_1$-$C_6$haloalkyl; and Z is a fused bicyclic ring of the formula,

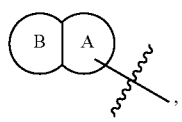

wherein
ring A is Ar or 5- or 6-membered Het,
ring B is 5- or 6-membered Het,
wherein
Z is optionally substituted by one or two —$R^Z$ groups that are each independently halogen, cyano, $C_{1-6}$alkyl, $C_{1-6}$haloalkyl, —OR, —SR, —$NR_2$, —C(O)R, —C(O)OR, —C(O)$NR_2$, —S(O)$_2NR_2$, —S(O)$_2$R, —OC(O)R, —N(R)C(O)R, —OC(O)OR, —OC(O)$NR_2$, —N(R)S(O)$_2$R, —O—$C_{1-6}$ alkyl-OR, —O—$C_{1-6}$ alkyl-SR, —O—$C_{1-6}$ alkyl-$NR_2$, or $C_{3-8}$Cak wherein each Cak and alkyl group is optionally substituted by one or two —$R^{Z2}$ groups;
wherein each —$R^{Z2}$ is independently halogen, cyano, $C_{1-6}$alkyl, $C_{1-6}$haloalkyl, —$C_1$-$C_6$alkoxy, —$OR^b$, —$NR^b_2$, —C(O)$R^b$, —C(O)O$R^b$, —C(O)$NR^b_2$, —S(O)$_2NR^b_2$, or —S(O)$_2R^b$;
each R is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, and alkyl are optionally substituted with $C_1$-$C_6$alkyl, halogen, or $C_1$-$C_6$haloalkyl;
each $R^b$ is independently hydrogen or $C_1$-$C_6$alkyl.

In embodiment $I_2$, the compounds are of embodiment $I_1$, provided that the compound is not:
4-(2-phenyl-5,6-dihydro-4H-pyrrolo[1,2-b]pyrazol-3-yl)quinoline,
4-(2-(4-fluorophenyl)-5,6-dihydro-4H-pyrrolo[1,2-b]pyrazol-3-yl)quinoline,
4-(2-(3-fluorophenyl)-5,6-dihydro-4H-pyrrolo[1,2-b]pyrazol-3-yl)quinoline,
4-(2-(2-fluorophenyl)-5,6-dihydro-4H-pyrrolo[1,2-b]pyrazol-3-yl)quinoline,
4-(2-(4-(trifluoromethyl)phenyl)-5,6-dihydro-4H-pyrrolo[1,2-b]pyrazol-3-yl)quinoline,
4-(2-(3-(trifluoromethyl)phenyl)-5,6-dihydro-4H-pyrrolo[1,2-b]pyrazol-3-yl)quinoline, 4-(2-(3-fluoro-5-(trifluoromethyl)phenyl)-5,6-dihydro-4H-pyrrolo[1,2-b]pyrazol-3-yl)quinoline,
4-(2-(3-(trifluoromethoxy)phenyl)-5,6-dihydro-4H-pyrrolo[1,2-b]pyrazol-3-yl)quinoline,
4-(2-(4-fluoro-3-(trifluoromethyl)phenyl)-5,6-dihydro-4H-pyrrolo[1,2-b]pyrazol-3-yl)quinoline,
4-(2-(2-fluoro-3-(trifluoromethyl)phenyl)-5,6-dihydro-4H-pyrrolo[1,2-b]pyrazol-3-yl)quinoline,
6-(2-phenyl-5,6-dihydro-4H-pyrrolo[1,2-b]pyrazol-3-yl)-1H-benzo[d]imidazole,
6-(2-(2,4-difluorophenyl)-5,6-dihydro-4H-pyrrolo[1,2-b]pyrazol-3-yl)-3-isopropyl-[1,2,4]triazolo[4,3-b]pyridazine, or
1-(isopropylsulfonyl)-6-(2-phenyl-5,6-dihydro-4H-pyrrolo[1,2-b]pyrazol-3-yl)-1H-benzo[d]imidazol-2-amine.

In embodiment $I_3$, the compound of embodiment $I_1$ is not one wherein m is 1, l is 0, n is 0, 1, or 2, X is —$CH_2$—, Z is not unsubstituted 4-quinolinyl.

In embodiment $I_4$, the compounds are of embodiment $I_1$, provided that the compound is not:
6-(2-phenyl-5,6-dihydro-4H-pyrrolo[1,2-b]pyrazol-3-yl)-1H-benzo[d]imidazole,
6-(2-(2,4-difluorophenyl)-5,6-dihydro-4H-pyrrolo[1,2-b]pyrazol-3-yl)-3-isopropyl-[1,2,4]triazolo[4,3-b]pyridazine, or
1-(isopropylsulfonyl)-6-(2-phenyl-5,6-dihydro-4H-pyrrolo[1,2-b]pyrazol-3-yl)-1H-benzo[d]imidazol-2-amine.

In embodiment $I_5$, the compounds are of embodiment $I_1$, provided that
(a) when m is 1, l is 0, n is 0, 1, or 2, X is —$CH_2$—, Z is not unsubstituted 4-quinolinyl; and
(b) the compound is not:
6-(2-phenyl-5,6-dihydro-4H-pyrrolo[1,2-b]pyrazol-3-yl)-1H-benzo[d]imidazole,
6-(2-(2,4-difluorophenyl)-5,6-dihydro-4H-pyrrolo[1,2-b]pyrazol-3-yl)-3-isopropyl-[1,2,4]triazolo[4,3-b]pyridazine, or
1-(isopropylsulfonyl)-6-(2-phenyl-5,6-dihydro-4H-pyrrolo[1,2-b]pyrazol-3-yl)-1H-benzo[d]imidazol-2-amine.

The invention further comprises subgenera of formula (I) in which structural formula (I), n, R', p and $R^2$, and Z are independently selected from the groups (Ia) et seq., (1a) et seq., (2a) et seq., and (3a) et seq. defined hereinbelow (e.g., wherein the compound is of structural formula (I) as defined in any of the above embodiments:

Structural Formula (I) is one of formulae (Ia)-(Ih):

(Ia)
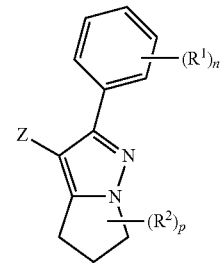

(Ib)
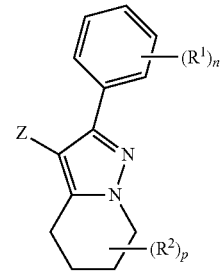

(Ic)
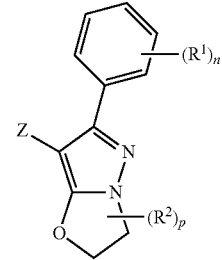

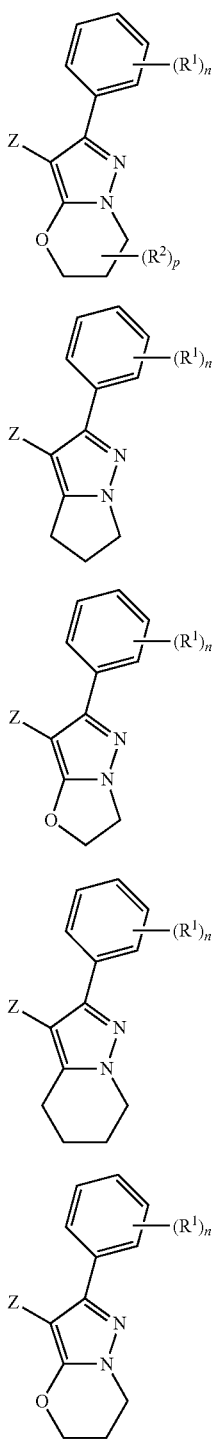

n is selected from one of the following groups (1a)-(1i):
(1a) n is 0, 1, 2, 3, or 4.
(1b) n is 0, 1, 2, or 3.
(1c) n is 0, 1, or 2.
(1d) n is 0 or 1.
(1e) n is 0.
(1f) n is 1, 2, or 3.
(1g) n is 1 or 2.
(1h) n is 1.
(1i) n is 2.

$R^1$ is selected from one of the following groups (2a)-(2ff):

(2a) Each $R^1$ is independently halogen, $-C_1$-$C_6$alkyl, $-C_1$-$C_6$haloalkyl, $-C_1$-$C_6$alkoxy, $-C_1$-$C_6$haloalkoxy, $C_{3-8}$ Cak($C_{0-6}$ alkyl), Hca($C_{0-6}$ alkyl), Ar($C_{0-6}$ alkyl), Het($C_{0-6}$ alkyl), $-O-(C_0$-$C_6$alkyl)-Ar, $-O-(C_0$-$C_6$alkyl)-Het, $-O-(C_0$-$C_6$alkyl)-Cak, $-O-(C_0$-$C_6$alkyl)-Hca, $-NO_2$, or $-CN$, wherein the Ar, Het, Cak, Hca, and alkyl are optionally substituted with 1, 2, 3, or 4 groups that are each independently halogen, cyano, nitro, $-OR'$, $-SR^a$, $-NR^a_2$, $-C(O)OR^a$, $-C(O)NR^a_2$, $-C(O)R^a$, $-S(O)R^a$, $-S(O)_2R^a$, $-S(O)OR^a$, $-S(O)_{20}R^a$, $-S(O)NR^a_2$, $-S(O)_2NR^a_2$, $-OC(O)R^a$, $-OC(O)OR^a$, $-OC(O)NR^a_2$, $-N(R)C(O)R^a$, $-N(R)C(O)OR^a$, $-N(R)C(O)NR^a_2$, $-N(R)S(O)R^a$, $-N(R^a)S(O)_2R^a$, $C_1$-$C_6$alkyl, or $C_1$-$C_6$haloalkyl;

each $R^a$ is independently hydrogen, $C_1$-$C_6$alkyl, $C_1$-$C_6$haloalkyl, $-(C_0$-$C_6$alkyl)-Ar, $-(C_0$-$C_6$alkyl)-Het, $-(C_0$-$C_6$alkyl)-Cak, or $-(C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(2b) Each $R^1$ is independently halogen, $-C_1$-$C_6$alkyl, $-C_1$-$C_6$haloalkyl, $-C_1$-$C_6$alkoxy, $-C_1$-$C_6$haloalkoxy, $-O-(C_0$-$C_6$alkyl)-Ar, $-O-(C_0$-$C_6$alkyl)-Het, $-O-(C_0$-$C_6$alkyl)-Cak, $-O-(C_0$-$C_6$alkyl)-Hca, $-NO_2$ or $-CN$, wherein the Ar, Het, Cak, Hca, alkyl, and haloalkyl are optionally substituted with 1, 2, 3, or 4 groups that are each independently halogen, cyano, nitro, $-OR'$, $-SR^a$, $-NR^a_2$, $-C(O)OR^a$, $-C(O)NR^a_2$, $-C(O)R^a$, $-S(O)R^a$, $-S(O)_2R^a$, $-S(O)OR^a$, $-S(O)_2OR^a$, $-S(O)NR^a_2$, $-S(O)_2NR^a_2$, $-OC(O)R^a$, $-OC(O)OR^a$, $-OC(O)NR^a_2$, $-N(R)C(O)R^a$, $-N(R)C(O)OR^a$, $-N(R)C(O)NR^a_2$, $-N(R)S(O)R^a$, $-N(R^a)S(O)_2R^a$, $C_1$-$C_6$alkyl, or $C_1$-$C_6$haloalkyl.

(2c) Each $R^1$ is independently halogen, $-C_1$-$C_6$alkyl, $-C_1$-$C_6$haloalkyl, $-C_1$-$C_6$alkoxy, $-C_1$-$C_6$haloalkoxy, $-NO_2$ or $-CN$, wherein the alkyl, and haloalkyl are optionally substituted with 1, 2, 3, or 4 groups that are each independently halogen, cyano, nitro, $-OR'$, $-SR^a$, $-NR^a_2$, $-C(O)OR^a$, $-C(O)NR^a_2$, $-C(O)R^a$, $-S(O)R^a$, $-S(O)_2R^a$, $-S(O)OR^a$, $-S(O)_2OR^a$, $-S(O)NR^a_2$, $-S(O)_2NR^a_2$, $-OC(O)R^a$, $-OC(O)OR^a$, $-OC(O)NR^a_2$, $-N(R)C(O)R^a$, $-N(R)C(O)OR^a$, $-N(R)C(O)NR^a_2$, $-N(R)S(O)R^a$, $-N(R^a)S(O)_2R^a$, $C_1$-$C_6$alkyl, or $C_1$-$C_6$haloalkyl.

(2d) Each $R^1$ is independently halogen, $-C_1$-$C_6$alkyl, $-C_1$-$C_6$haloalkyl, $-C_1$-$C_6$alkoxy, $-C_1$-$C_6$haloalkoxy, $-O-(C_0$-$C_6$alkyl)-Ar, $-O-(C_0$-$C_6$alkyl)-Het, $-O-(C_0$-$C_6$alkyl)-Cak, $-O-(C_0$-$C_6$alkyl)-Hca, $-NO_2$ or $-CN$, wherein the Ar, Het, Cak, Hca, alkyl, and haloalkyl are optionally substituted with 1, 2, 3, or 4 groups that are each independently halogen, cyano, nitro, $-OR'$, $-SR^a$, $-NR^a_2$, $-C(O)OR^a$, $-C(O)NR^a_2$, $-C(O)R^a$, $-S(O)R^a$, $-S(O)_2R^a$, $-S(O)OR^a$, $-S(O)_2OR^a$, $-S(O)NR^a_2$, $-S(O)_2NR^a_2$, $-OC(O)R^a$, $-OC(O)OR^a$, $-OC(O)NR^a_2$, $-N(R)C(O)R^a$, $-N(R)C(O)OR^a$, $-N(R)C(O)NR^a_2$, $-N(R)S(O)R^a$, $-N(R^a)S(O)_2R^a$, $C_1$-$C_6$alkyl, or $C_1$-$C_6$haloalkyl.

(2e) Each $R^1$ is independently halogen, $-C_1$-$C_6$alkyl, $-C_1$-$C_6$haloalkyl, $-C_1$-$C_6$alkoxy, $-C_1$-$C_6$haloalkoxy, or $-CN$, wherein the alkyl is optionally substituted with 1, 2, 3, or 4 groups that are each independently halogen, cyano, nitro, $-OR'$, $-SR'$, $-NR^a_2$, $-C(O)OR^a$, $-C(O)NR^a_2$, $-C(O)R^a$, —S(O)R$^a$, —S(O)$_2$R$^a$, —S(O)OR$^a$, —S(O)$_2$OR$^a$, —S(O)NR$^a_2$, —S(O)$_2$NR$^a_2$, —OC(O)R$^a$, —OC(O)OR$^a$, —OC(O)NR$^a_2$, —N(R)C(O)R$^a$, —N(R)C(O)OR$^a$, —N(R)C(O)NR$^a_2$, —N(R)S(O)R$^a$, —N(R$^a$)S(O)$_2$R$^a$, C$_1$-C$_6$alkyl, or C$_1$-C$_6$haloalkyl.

(2f) Each R$^1$ is independently halogen, —C$_1$-C$_6$alkyl, —C$_1$-C$_6$haloalkyl, —C$_1$-C$_6$alkoxy, —C$_1$-C$_6$haloalkoxy, —NO$_2$ or —CN.

(2g) Each R$^1$ is independently halogen, —C$_1$-C$_6$alkyl, —C$_1$-C$_6$haloalkyl, —C$_1$-C$_6$alkoxy, C$_{3-8}$Cak(C$_{0-6}$alkyl), Hca(C$_{0-6}$ alkyl), Ar(C$_{0-6}$ alkyl), Het(C$_{0-6}$ alkyl), —O—(C$_0$-C$_6$alkyl) —Ar, —O—(C$_0$-C$_6$alkyl)-Het, —O—(C$_0$-C$_6$alkyl)-Cak, —O—(C$_0$-C$_6$ alkyl)-Hca, —NO$_2$ or —CN.

(2h) Each R$^1$ is independently halogen, —C$_1$-C$_6$alkyl, —C$_1$-C$_6$haloalkyl, —C$_1$-C$_6$alkoxy, C$_{3-8}$ Cak(C$_{0-6}$ alkyl), Hca(C$_{0-6}$ alkyl), Ar(C$_{0-6}$ alkyl), Het(C$_{0-6}$ alkyl), —NO$_2$ or —CN.

(2i) Each R$^1$ is independently halogen, —C$_1$-C$_6$alkyl, —C$_1$-C$_6$haloalkyl, —C$_1$-C$_6$alkoxy, C$_{3-8}$ Cak(C$_{0-6}$ alkyl), Hca(C$_{0-6}$ alkyl), Ar(C$_{0-6}$ alkyl), Het(C$_{0-6}$ alkyl), —NO$_2$ or —CN.

(2j) Each R$^1$ is independently halogen, —C$_1$-C$_6$alkyl, —C$_1$-C$_6$haloalkyl, —C$_1$-C$_6$alkoxy, —NO$_2$ or —CN.

(2k) Each R$^1$ is independently halogen, —C$_1$-C$_6$alkyl, —C$_1$-C$_6$haloalkyl, —C$_1$-C$_6$alkoxy, or —C$_1$-C$_6$haloalkoxy.

(2l) Each R$^1$ is independently halogen, —C$_1$-C$_3$alkyl, —C$_1$-C$_3$haloalkyl, —C$_1$-C$_3$alkoxy, or —C$_1$-C$_3$haloalkoxy.

(2m) Each R$^1$ is independently halogen, —C$_1$-C$_6$alkyl, —C$_1$-C$_6$haloalkyl or —C$_1$-C$_6$alkoxy.

(2n) Each R$^1$ is independently halogen, —C$_1$-C$_3$alkyl, —C$_1$-C$_3$haloalkyl or —C$_1$-C$_3$alkoxy.

(2o) Each R$^1$ is independently halogen, —C$_1$-C$_6$alkyl or —C$_1$-C$_6$haloalkyl.

(2p) Each R$^1$ is independently halogen, —C$_1$-C$_3$alkyl or —C$_1$-C$_3$haloalkyl.

(2q) Each R$^1$ is independently halogen or —C$_1$-C$_6$alkyl.

(2r) Each R$^1$ is independently halogen or —C$_1$-C$_3$alkyl.

(2s) Each R$^1$ is independently halogen.

(2t) Each R$^1$ is independently fluoro or chloro.

(2u) Each R$^1$ is independently fluoro.

(2v) Each R$^1$ is independently —C$_1$-C$_6$alkyl or —C$_1$-C$_6$alkoxy.

(2w) Each R$^1$ is independently —C$_1$-C$_3$alkyl or —C$_1$-C$_3$alkoxy.

(2x) Each R$^1$ is independently —C$_1$-C$_6$alkyl, —C$_1$-C$_6$haloalkyl or —C$_1$-C$_6$alkoxy.

(2y) Each R$^1$ is independently —C$_1$-C$_3$alkyl, —C$_1$-C$_3$haloalkyl or —C$_1$-C$_3$alkoxy.

(2z) Each R$^1$ is independently halogen, methyl, trifluoromethyl, methoxy, or trifluoromethoxy.

(2aa) Each R$^1$ is independently fluoro, chloro, methyl, trifluoromethyl, methoxy, or trifluoromethoxy.

(2bb) Each R$^1$ is independently fluoro, methyl, trifluoromethyl, methoxy, or trifluoromethoxy.

(2cc) Each R$^1$ is independently fluoro, methyl, trifluoromethyl, or methoxy.

When p is 1, R$^2$ is selected from one of the following groups (3a)-(3o):

(3a) Each R$^2$ is independently halogen, C$_1$-C$_6$alkyl, C$_1$-C$_6$haloalkyl, —OR', —NR'2, C$_{3-8}$ Cak, —NO$_2$ or —CN, wherein each R$^c$ is independently hydrogen, C$_1$-C$_6$alkyl, or C$_1$-C$_6$haloalkyl.

(3b) Each R$^2$ is independently halogen, C$_1$-C$_6$alkyl, C$_1$-C$_6$haloalkyl, —OR', —NR'2, C$_{3-8}$Cak, —NO$_2$ or CN.

(3c) Each R$^2$ is independently halogen, C$_1$-C$_6$alkyl, C$_1$-C$_6$haloalkyl, —OR', —NR'2, or C$_{3-8}$ Cak.

(3d) Each R$^2$ is independently halogen, C$_1$-C$_6$alkyl, C$_1$-C$_6$haloalkyl, or —OR'.

(3e) Each R$^2$ is independently C$_1$-C$_6$alkyl, C$_1$-C$_6$haloalkyl, or —OR'.

(3f) Each R$^2$ is independently halogen, C$_1$-C$_6$alkyl, or C$_1$-C$_6$haloalkyl.

(3g) Each R$^2$ is independently C$_1$-C$_6$alkyl or —OR'.

(3h) Each R$^2$ is independently halogen, C$_1$-C$_3$alkyl, C$_1$-C$_3$haloalkyl, or —OR'.

(3i) Each R$^2$ is independently C$_1$-C$_3$alkyl, C$_1$-C$_3$haloalkyl, or —OR'.

(3j) Each R$^2$ is independently halogen, C$_1$-C$_3$alkyl, or C$_1$-C$_3$haloalkyl.

(3k) Each R$^2$ is independently C$_1$-C$_3$alkyl or —OR'.

(3l) Each R$^2$ is independently C$_1$-C$_6$alkyl.

(3m) Each R$^2$ is independently C$_1$-C$_3$alkyl.

(3n) Each R$^2$ is independently halogen, methyl, trifluoromethyl, methoxy, or trifluoromethoxy.

(3o) Each R$^2$ is independently methyl, trifluoromethyl, methoxy, or trifluoromethoxy.

Z is selected from one of the following groups (4a)-(4sss):

(4a) Z is a fused bicyclic ring of the formula, wherein ring A is Ar or 5- or 6-membered Het, ring B is 5- or 6-membered Het, wherein Z is optionally substituted by one or two —R$^Z$ groups that are each independently halogen, cyano, C$_{1-6}$alkyl, C$_{1-6}$haloalkyl, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)S(O)$_2$R, —O—C$_{1-6}$ alkyl-OR, —O—C$_{1-6}$ alkyl-SR, —O—C$_{1-6}$ alkyl-NR$_2$, or C$_{3-8}$Cak wherein each Cak and alkyl group is optionally substituted by one or two —R$^{ZZ}$ groups;

wherein each —R$^{ZZ}$ is independently halogen, cyano, C$_{1-6}$alkyl, C$_{1-6}$haloalkyl, —C$_1$-C$_6$alkoxy, —OR$^b$, —NR$^b_2$, —C(O)R$^b$, —C(O)OR$^b$, —C(O)NR$^b_2$, —S(O)$_2$NR$^b_2$, or —S(O)$_2$R$^b$;

each R is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, and alkyl are optionally substituted with C$_1$-C$_6$alkyl, halogen, or C$_1$-C$_6$haloalkyl;

each R$^b$ is independently hydrogen or C$_1$-C$_6$alkyl.

(4b) Z is as described in (4a), provided that Z is not

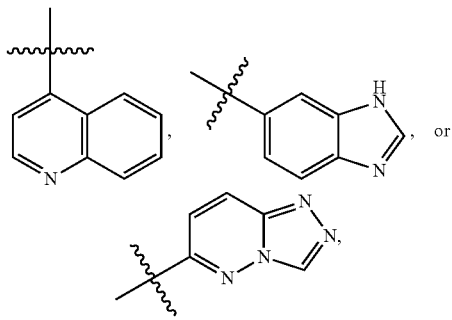

wherein each is optionally substituted.

(4c) Z is as described in (4a), provided that Z is not

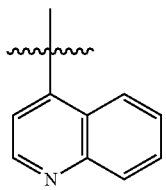 [SMILES: *c1ccnc2ccccc12]

or a substituted analog thereof.

(4d) Z is as described in (4a), provided that Z is not

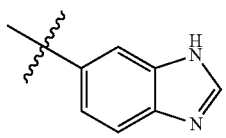 [SMILES: *c1ccc2nc[nH]c2c1]

or a substituted analog thereof.

(4e) Z is as described in (4a), provided that Z is not

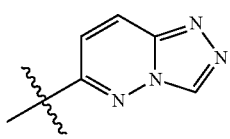 [SMILES: *c1ccc2nncn2n1]

or a substituted analog thereof.

(4f) Z is a fused bicyclic ring of the formula,

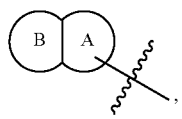

wherein
ring A is Ar; and
ring B is 5- or 6-membered Het; wherein
optionally substituted as described in (4a) above.

(4g) Z is a fused bicyclic ring of the formula,

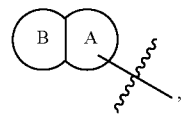

wherein
ring A is Ar; and
ring B is 5-membered Het; wherein
optionally substituted as described in (4a) above.

(4h) Z is a fused bicyclic ring of the formula,

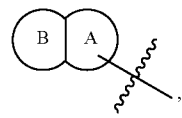

wherein
ring A is Ar; and
ring B is 6-membered Het; wherein
optionally substituted as described in (4a) above.

(4i) Z is a fused bicyclic ring of the formula,

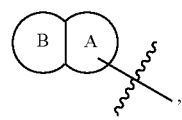

wherein
ring A is 5-membered Het; and
ring B is 5- or 6-membered Het; wherein
optionally substituted as described in (4a) above.

(4j) Z is a fused bicyclic ring of the formula,

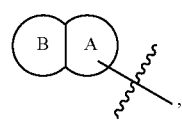

wherein
ring A is 5-membered Het; and
ring B is 5-membered Het; wherein
optionally substituted as described in (4a) above.

(4k) Z is a fused bicyclic ring of the formula,

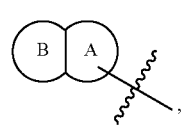

wherein
ring A is 5-membered Het; and
ring B is 6-membered Het; wherein
optionally substituted as described in (4a) above.

(4l) Z is a fused bicyclic ring of the formula,

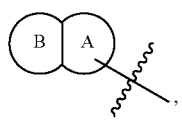

wherein
ring A is 6-membered Het; and
ring B is 5- or 6-membered Het; wherein
optionally substituted as described in (4a) above.

(4m) Z is a fused bicyclic ring of the formula,

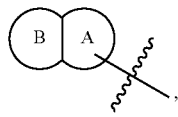

wherein
ring A is 6-membered Het; and
ring B is 5-membered Het; wherein
optionally substituted as described in (4a) above.

(4n) Z is a fused bicyclic ring of the formula,

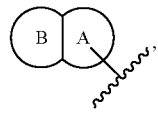

wherein
ring A is 6-membered Het; and
ring B is 6-membered Het; wherein
optionally substituted as described in (4a) above.

(4o) Z is

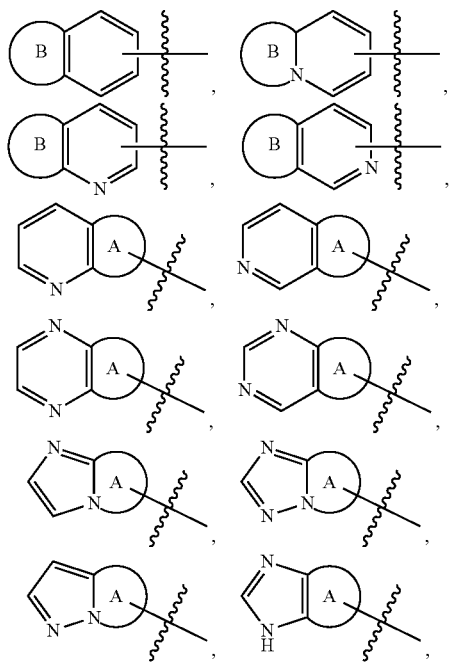

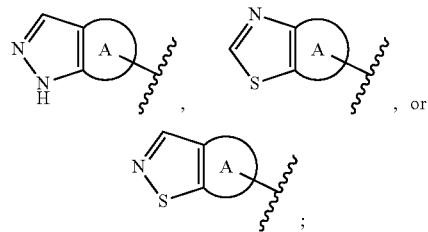

wherein ring A and B are as described in (4a), and Z is optionally substituted as described in (4a) above.

(4p) Z is

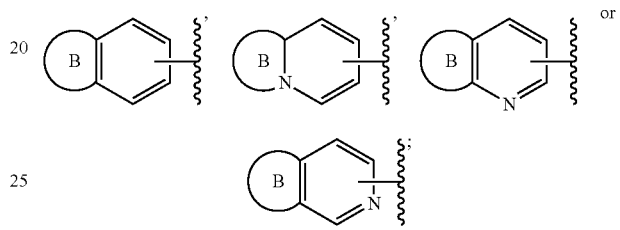

wherein ring B is as described in (4a), and Z is optionally substituted as described in (4a) above.

(4q) Z is

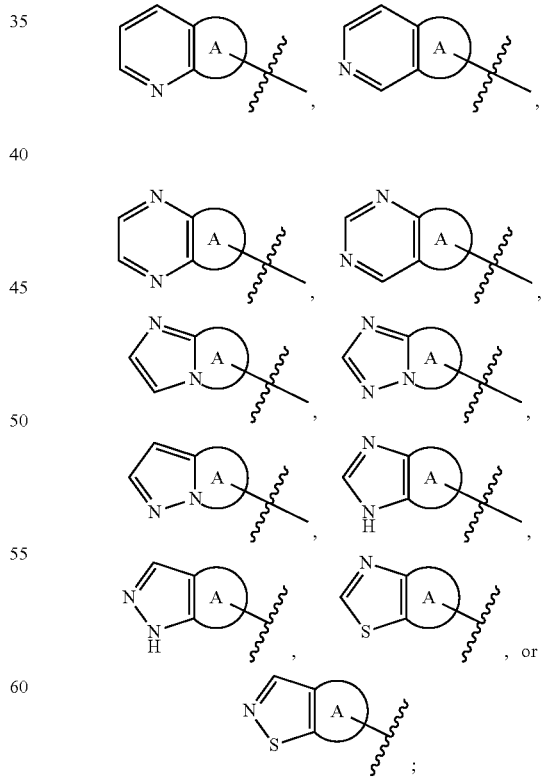

wherein ring A is as described in (4a), and Z is optionally substituted as described in (4a) above.

(4r) Z is

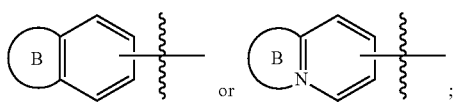

wherein ring B is as described in (4a), and Z is optionally substituted as described in (4a) above.

(4s) Z is

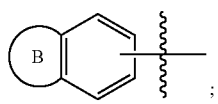

wherein ring B is as described in (4a), and Z is optionally substituted as described in (4a) above.

(4t) Z is

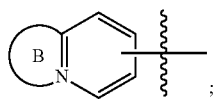

wherein ring B is as described in (4a), and Z is optionally substituted as described in (4a) above.

(4u) Z is

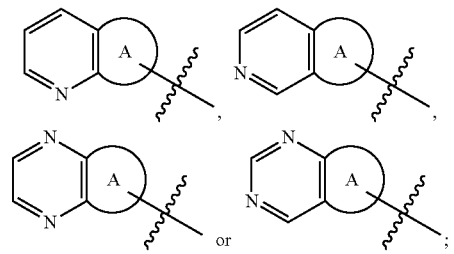

wherein ring A is as described in (4a), and Z is optionally substituted as described in (4a) above.

(4v) Z is

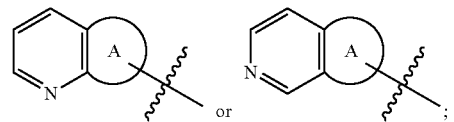

wherein ring A is as described in (4a), and Z is optionally substituted as described in (4a) above.

(4w) Z is

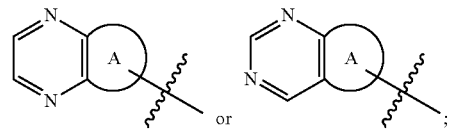

wherein ring A is as described in (4a), and Z is optionally substituted as described in (4a) above.

(4x) Z is

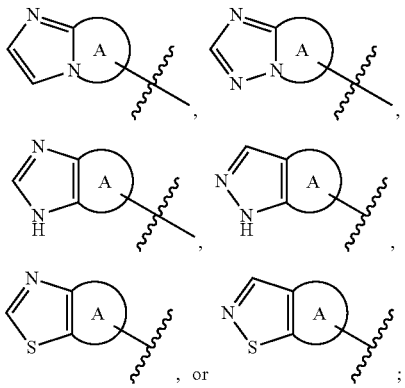

wherein ring A is as described in (4a), and Z is optionally substituted as described in (4a) above.

(4y) Z is

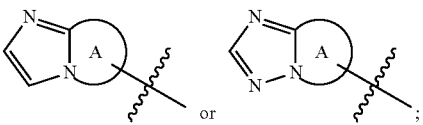

wherein ring A is as described in (4a), and Z is optionally substituted as described in (4a) above.

(4z) Z is

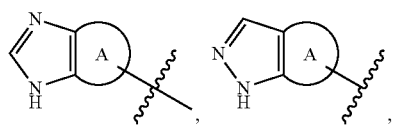

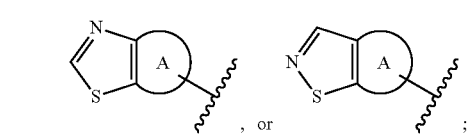

wherein ring A is as described in (4a), and Z is optionally substituted as described in (4a) above.

(4aa) Z is

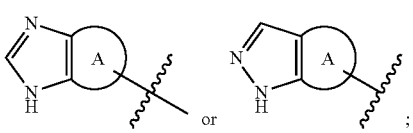

wherein ring A is as described in (4a), and Z is optionally substituted as described in (4a) above.

(4bb) Z is

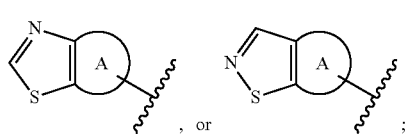, or ;

wherein ring A is as described in (4a), and Z is optionally substituted as described in (4a) above.

(4cc) Z is

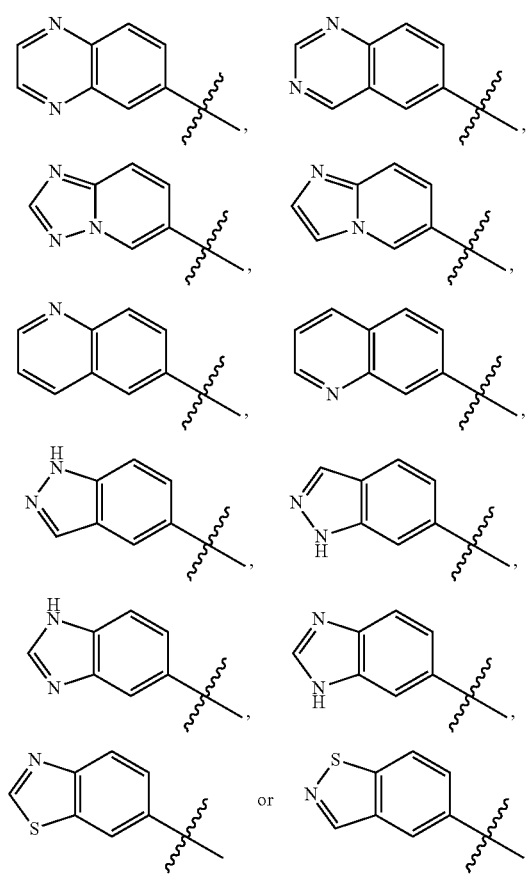

each optionally substituted as described in (4a) above.

(4dd) Z is

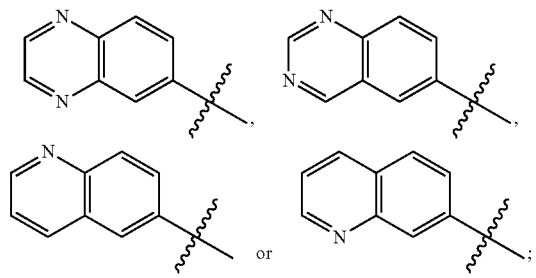

each optionally substituted as described in (4a) above.

(4ee) Z is

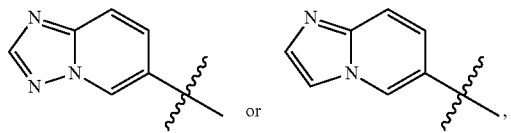 [SMILES: *c1ccc2ncnn2c1 ; *c1ccc2nccn2c1] or , each optionally substituted as described in (4a) above.

(4ff) Z is

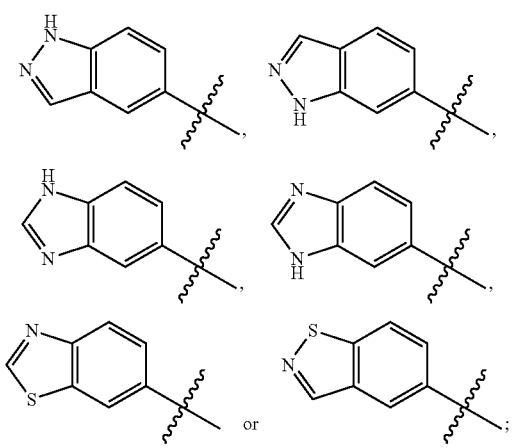 or ;

each optionally substituted as described in (4a) above.

(4gg) Z is

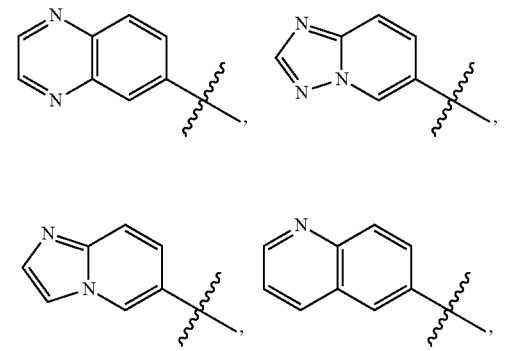

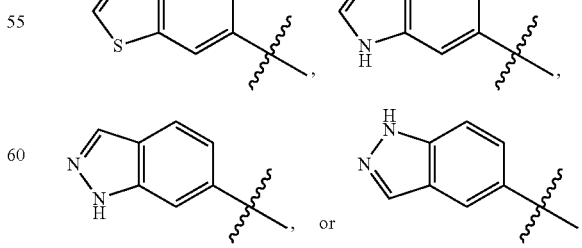, or ;

(4hh) each optionally substituted as described in (4a) above.

(4ii) Z is

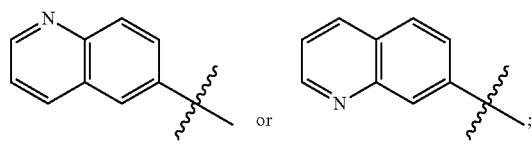 [SMILES: *c1ccc2ncccc2c1 ; *c1ccc2cccnc2c1]
or optionally substituted as described in (4a) above.

(4jj) Z is

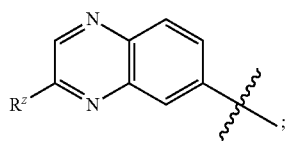

wherein $R^Z$ is as described in (4a).

(4kk) Z is

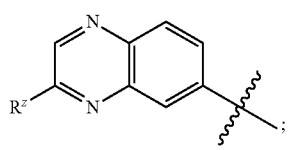

wherein $R^Z$ is hydrogen, —OR, —O—$C_{1-6}$ alkyl-OR, or —O—$C_{1-6}$ alkyl-NR$_2$.

(4ll) The group (4kk) wherein $R^Z$ is hydrogen, —OR, or —O—$C_{1-6}$alkyl-OR.

(4 mm) The group (4kk) wherein $R^Z$ is hydrogen.

(4nn) Z is

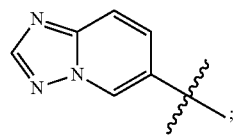 [SMILES: *c1ccc2ncnn2c1]

optionally substituted as described in (4a) above.

(4oo) Z is

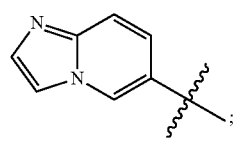 [SMILES: *c1ccc2nccn2c1]

optionally substituted as described in (4a) above.

(4pp) Z is

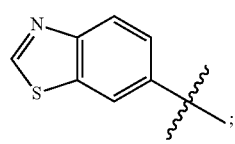 [SMILES: *c1ccc2ncsc2c1]

optionally substituted as described in (4a) above.

(4qq) Z is

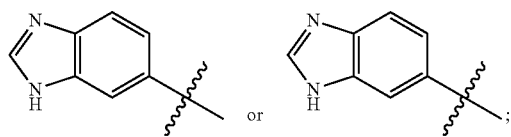 [SMILES: *c1ccc2nc[nH]c2c1 ; *c1ccc2nc[nH]c2c1]
or optionally substituted as described in (4a) above.

(4rr) Z is

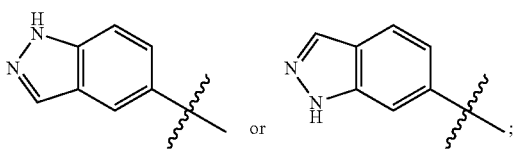 [SMILES: *c1ccc2[nH]ncc2c1 ; *c1ccc2cn[nH]c2c1]
or optionally substituted as described in (4a) above.

(4ss) Z is

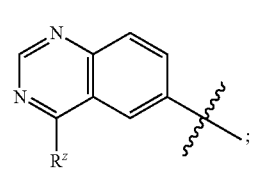

wherein $R^Z$ is as described in (4a).

(4tt) Z is

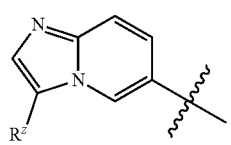

wherein $R^Z$ is as described in (4a).

(4uu) Z is

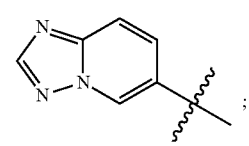 [SMILES: *c1ccc2ncnn2c1]

optionally substituted with one or two $R^Z$ groups as described in (4a).

(4vv) Z is

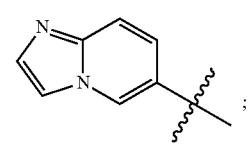 [SMILES: *c1ccc2nccn2c1]

optionally substituted with one or two $R^Z$ groups as described in (4a).

(4ww) Z is

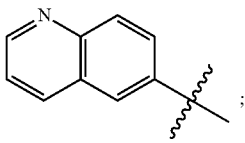 [SMILES: *c1ccc2ncccc2c1]

optionally substituted with one or two R^Z groups as described in (4a).

(4xx) Z is

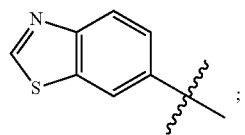 [SMILES: *c1ccc2ncsc2c1]

optionally substituted with one or two R^Z groups as described in (4a).

(4yy) Z is

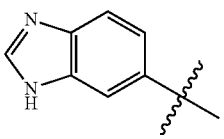 or 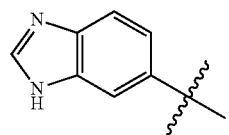

optionally substituted with one or two R^Z groups as described in (4a).

(4zz) Z is

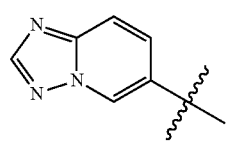 or 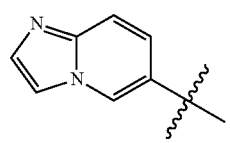

optionally substituted with one or two R^Z groups as described in (4a).

(4aaa) Z is (4bbb) Z is (4ccc) Z is

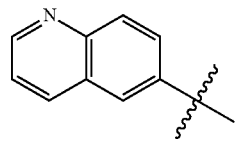

(4ddd) Z is

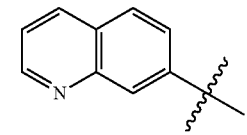

(4eee) Z is

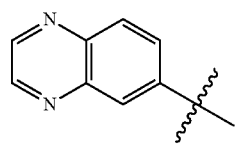

(4fff) Z is

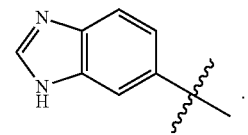 [SMILES: *c1ccc2nc[nH]c2c1]

(4ggg) Z is

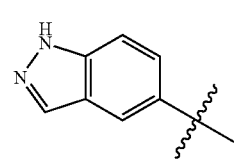

(4hhh) Z is (4iii) Z is

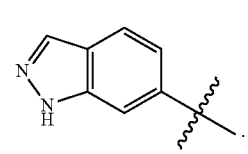

(4jjj) Z is

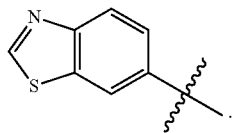 [SMILES: *c1ccc2ncsc2c1]

(4kkk) The group of (4a)-(4jjj), wherein each $R^Z$ is independently halogen, $C_{1-6}$ alkyl, $C_{1-6}$haloalkyl, —OR, —NR$_2$, —C(O)NR$_2$, or $C_{3-8}$Cak.

(4lll) The group of (4a)-(4jjj), wherein each $R^Z$ is independently halogen, $C_{1-6}$alkyl, or $C_{1-6}$haloalkyl.

(4mmm) The group of (4a)-(4jjj), wherein each $R^Z$ is independently $C_{1-6}$ alkyl or $C_{1-6}$haloalkyl.

(4nnn) The group of (4a)-(4jjj), wherein each $R^Z$ is independently $C_{1-3}$alkyl or $C_{1-3}$haloalkyl.

(4ooo) The group of (4a)-(4jjj), wherein each $R^Z$ is independently methyl or trifluoroalkyl.

(4ppp) The group of (4a)-(4jjj), wherein Z is unsubstituted.

(4qqq) Z is

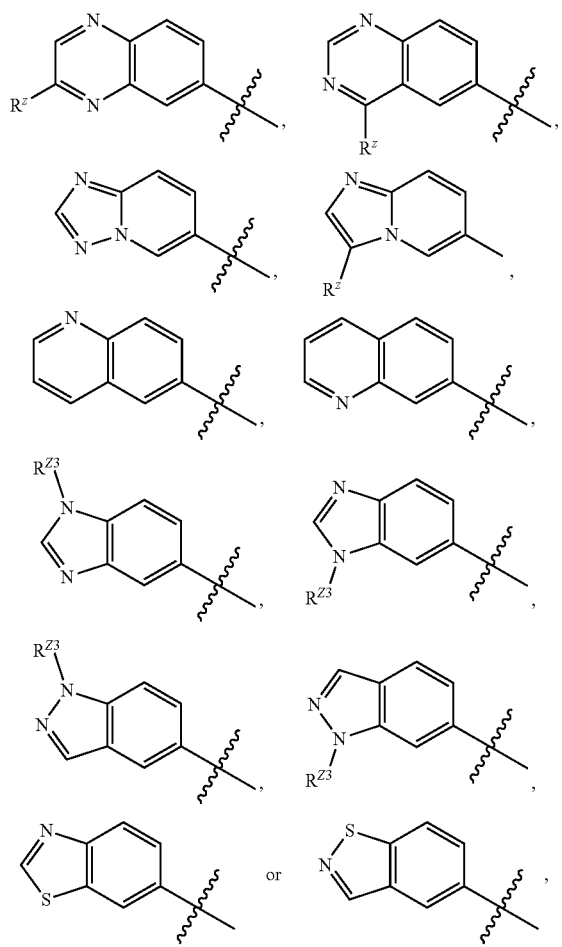

wherein $R^{Z3}$ is hydrogen or $C_{1-6}$ alkyl.

(4rrr) Z is

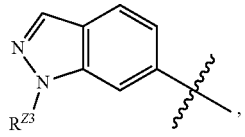 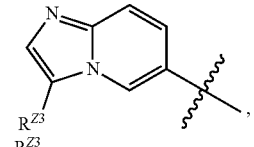

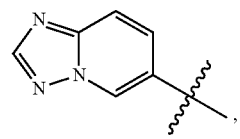 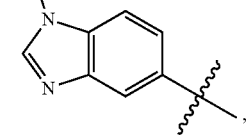

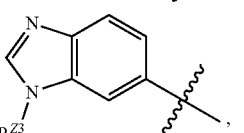 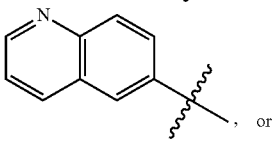

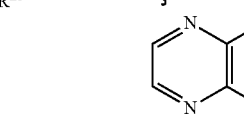, wherein $R^{Z3}$ is hydrogen or $C_{1-6}$ alkyl.

(4sss) The group of (4qqq) or (4rrr), wherein each $R^{Z3}$ is independently hydrogen or methyl.

Particular embodiments of this aspect of the invention comprise compounds of any one of the formulae (I) and (Ia)-(Ih), each as defined in each of the following rows (or a pharmaceutically acceptable salt, prodrug, or N-oxide thereof, or a solvate or hydrate thereof), wherein each entry is a group number as defined above (e.g., (1g) refers to n being 1 or 2), and a dash "-" indicates that the variable is as defined in any one of embodiments or defined according to any one of the applicable variable definitions (Ia)-(Ih), (1a)-(1i), (2a)-(2ff), (3a)-(3o), and (4a)-(4sss) [e.g., when n is a dash, it can be either as defined in any of embodiments $I_1$-$I_5$ or any one of applicable definitions (1a)-(1i)]:

|  | (I) | n | $R^1$ | $R^2$ | Z |
|---|---|---|---|---|---|
| (1)-1 | (I) | (1a) | (2a) | (3c) | (4a) |
| (1)-2 | (I) | (1f) | (2a) | (3c) | (4a) |
| (1)-3 | (I) | (1a) | (2a) | (3c) | (4o) |
| (1)-4 | (I) | (1f) | (2a) | (3c) | (4o) |
| (1)-5 | (I) | (1a) | (2a) | (3c) | (4cc) |
| (1)-6 | (I) | (1f) | (2a) | (3c) | (4cc) |
| (1)-7 | (I) | (1a) | (2a) | (3c) | (4lll) |
| (1)-8 | (I) | (1f) | (2a) | (3c) | (4lll) |
| (1)-9 | (I) | (1a) | (2a) | (3c) | (4qqq) |
| (1)-10 | (I) | (1f) | (2a) | (3c) | (4qqq) |
| (1)-11 | (I) | (1a) | (2k) | (3c) | (4a) |
| (1)-12 | (I) | (1f) | (2k) | (3c) | (4a) |
| (1)-13 | (I) | (1a) | (2k) | (3c) | (4o) |
| (1)-14 | (I) | (1f) | (2k) | (3c) | (4o) |
| (1)-15 | (I) | (1a) | (2k) | (3c) | (4cc) |
| (1)-16 | (I) | (1f) | (2k) | (3c) | (4cc) |
| (1)-17 | (I) | (1a) | (2k) | (3c) | (4lll) |
| (1)-18 | (I) | (1f) | (2k) | (3c) | (4lll) |
| (1)-19 | (I) | (1a) | (2k) | (3c) | (4qqq) |
| (1)-20 | (I) | (1f) | (2k) | (3c) | (4qqq) |
| (1)-21 | (I) | (1a) | (2z) | (3c) | (4a) |
| (1)-22 | (I) | (1f) | (2z) | (3c) | (4a) |
| (1)-23 | (I) | (1a) | (2z) | (3c) | (4o) |
| (1)-24 | (I) | (1f) | (2z) | (3c) | (4o) |
| (1)-25 | (I) | (1a) | (2z) | (3c) | (4cc) |
| (1)-26 | (I) | (1f) | (2z) | (3c) | (4cc) |
| (1)-27 | (I) | (1a) | (2z) | (3c) | (4lll) |
| (1)-28 | (I) | (1f) | (2z) | (3c) | (4lll) |

| (I) | n | R¹ | R² | Z | | (I) | n | R¹ | R² | Z |
|---|---|---|---|---|---|---|---|---|---|---|
| (1)-29 | (I) | (1a) | (2z) | (3c) | (4qqq) | (1)-106 | (Ib) | (1f) | (2z) | (3c) | (4cc) |
| (1)-30 | (I) | (1f) | (2z) | (3c) | (4qqq) | (1)-107 | (Ib) | (1a) | (2z) | (3c) | (4lll) |
| (1)-31 | (I) | (1a) | (2aa) | (3c) | (4a) | (1)-108 | (Ib) | (1f) | (2z) | (3c) | (4lll) |
| (1)-32 | (I) | (1f) | (2aa) | (3c) | (4a) | (1)-109 | (Ib) | (1a) | (2z) | (3c) | (4qqq) |
| (1)-33 | (I) | (1a) | (2aa) | (3c) | (4o) | (1)-110 | (Ib) | (1f) | (2z) | (3c) | (4qqq) |
| (1)-34 | (I) | (1f) | (2aa) | (3c) | (4o) | (1)-111 | (Ib) | (1a) | (2aa) | (3c) | (4a) |
| (1)-35 | (I) | (1a) | (2aa) | (3c) | (4cc) | (1)-112 | (Ib) | (1f) | (2aa) | (3c) | (4a) |
| (1)-36 | (I) | (1f) | (2aa) | (3c) | (4cc) | (1)-113 | (Ib) | (1a) | (2aa) | (3c) | (4o) |
| (1)-37 | (I) | (1a) | (2aa) | (3c) | (4lll) | (1)-114 | (Ib) | (1f) | (2aa) | (3c) | (4o) |
| (1)-38 | (I) | (1f) | (2aa) | (3c) | (4lll) | (1)-115 | (Ib) | (1a) | (2aa) | (3c) | (4cc) |
| (1)-39 | (I) | (1a) | (2aa) | (3c) | (4qqq) | (1)-116 | (Ib) | (1f) | (2aa) | (3c) | (4cc) |
| (1)-40 | (I) | (1f) | (2aa) | (3c) | (4qqq) | (1)-117 | (Ib) | (1a) | (2aa) | (3c) | (4lll) |
| (1)-41 | (Ia) | (1a) | (2a) | (3c) | (4a) | (1)-118 | (Ib) | (1f) | (2aa) | (3c) | (4lll) |
| (1)-42 | (Ia) | (1f) | (2a) | (3c) | (4a) | (1)-119 | (Ib) | (1a) | (2aa) | (3c) | (4qqq) |
| (1)-43 | (Ia) | (1a) | (2a) | (3c) | (4o) | (1)-120 | (Ib) | (1f) | (2aa) | (3c) | (4qqq) |
| (1)-44 | (Ia) | (1f) | (2a) | (3c) | (4o) | (1)-121 | (Ic) | (1a) | (2a) | (3c) | (4a) |
| (1)-45 | (Ia) | (1a) | (2a) | (3c) | (4cc) | (1)-122 | (Ic) | (1f) | (2a) | (3c) | (4a) |
| (1)-46 | (Ia) | (1f) | (2a) | (3c) | (4cc) | (1)-123 | (Ic) | (1a) | (2a) | (3c) | (4o) |
| (1)-47 | (Ia) | (1a) | (2a) | (3c) | (4lll) | (1)-124 | (Ic) | (1f) | (2a) | (3c) | (4o) |
| (1)-48 | (Ia) | (1f) | (2a) | (3c) | (4lll) | (1)-125 | (Ic) | (1a) | (2a) | (3c) | (4cc) |
| (1)-49 | (Ia) | (1a) | (2a) | (3c) | (4qqq) | (1)-126 | (Ic) | (1f) | (2a) | (3c) | (4cc) |
| (1)-50 | (Ia) | (1f) | (2a) | (3c) | (4qqq) | (1)-127 | (Ic) | (1a) | (2a) | (3c) | (4lll) |
| (1)-51 | (Ia) | (1a) | (2k) | (3c) | (4a) | (1)-128 | (Ic) | (1f) | (2a) | (3c) | (4lll) |
| (1)-52 | (Ia) | (1f) | (2k) | (3c) | (4a) | (1)-129 | (Ic) | (1a) | (2a) | (3c) | (4qqq) |
| (1)-53 | (Ia) | (1a) | (2k) | (3c) | (4o) | (1)-130 | (Ic) | (1f) | (2a) | (3c) | (4qqq) |
| (1)-54 | (Ia) | (1f) | (2k) | (3c) | (4o) | (1)-131 | (Ic) | (1a) | (2k) | (3c) | (4a) |
| (1)-55 | (Ia) | (1a) | (2k) | (3c) | (4cc) | (1)-132 | (Ic) | (1f) | (2k) | (3c) | (4a) |
| (1)-56 | (Ia) | (1f) | (2k) | (3c) | (4cc) | (1)-133 | (Ic) | (1a) | (2k) | (3c) | (4o) |
| (1)-57 | (Ia) | (1a) | (2k) | (3c) | (4lll) | (1)-134 | (Ic) | (1f) | (2k) | (3c) | (4o) |
| (1)-58 | (Ia) | (1f) | (2k) | (3c) | (4lll) | (1)-135 | (Ic) | (1a) | (2k) | (3c) | (4cc) |
| (1)-59 | (Ia) | (1a) | (2k) | (3c) | (4qqq) | (1)-136 | (Ic) | (1f) | (2k) | (3c) | (4cc) |
| (1)-60 | (Ia) | (1f) | (2k) | (3c) | (4qqq) | (1)-137 | (Ic) | (1a) | (2k) | (3c) | (4lll) |
| (1)-61 | (Ia) | (1a) | (2z) | (3c) | (4a) | (1)-138 | (Ic) | (1f) | (2k) | (3c) | (4lll) |
| (1)-62 | (Ia) | (1f) | (2z) | (3c) | (4a) | (1)-139 | (Ic) | (1a) | (2k) | (3c) | (4qqq) |
| (1)-63 | (Ia) | (1a) | (2z) | (3c) | (4o) | (1)-140 | (Ic) | (1f) | (2k) | (3c) | (4qqq) |
| (1)-64 | (Ia) | (1f) | (2z) | (3c) | (4o) | (1)-141 | (Ic) | (1a) | (2z) | (3c) | (4a) |
| (1)-65 | (Ia) | (1a) | (2z) | (3c) | (4cc) | (1)-142 | (Ic) | (1f) | (2z) | (3c) | (4a) |
| (1)-66 | (Ia) | (1f) | (2z) | (3c) | (4cc) | (1)-143 | (Ic) | (1a) | (2z) | (3c) | (4o) |
| (1)-67 | (Ia) | (1a) | (2z) | (3c) | (4lll) | (1)-144 | (Ic) | (1f) | (2z) | (3c) | (4o) |
| (1)-68 | (Ia) | (1f) | (2z) | (3c) | (4lll) | (1)-145 | (Ic) | (1a) | (2z) | (3c) | (4cc) |
| (1)-69 | (Ia) | (1a) | (2z) | (3c) | (4qqq) | (1)-146 | (Ic) | (1f) | (2z) | (3c) | (4cc) |
| (1)-70 | (Ia) | (1f) | (2z) | (3c) | (4qqq) | (1)-147 | (Ic) | (1a) | (2z) | (3c) | (4lll) |
| (1)-71 | (Ia) | (1a) | (2aa) | (3c) | (4a) | (1)-148 | (Ic) | (1f) | (2z) | (3c) | (4lll) |
| (1)-72 | (Ia) | (1f) | (2aa) | (3c) | (4a) | (1)-149 | (Ic) | (1a) | (2z) | (3c) | (4qqq) |
| (1)-73 | (Ia) | (1a) | (2aa) | (3c) | (4o) | (1)-150 | (Ic) | (1f) | (2z) | (3c) | (4qqq) |
| (1)-74 | (Ia) | (1f) | (2aa) | (3c) | (4o) | (1)-151 | (Ic) | (1a) | (2aa) | (3c) | (4a) |
| (1)-75 | (Ia) | (1a) | (2aa) | (3c) | (4cc) | (1)-152 | (Ic) | (1f) | (2aa) | (3c) | (4a) |
| (1)-76 | (Ia) | (1f) | (2aa) | (3c) | (4cc) | (1)-153 | (Ic) | (1a) | (2aa) | (3c) | (4o) |
| (1)-77 | (Ia) | (1a) | (2aa) | (3c) | (4lll) | (1)-154 | (Ic) | (1f) | (2aa) | (3c) | (4o) |
| (1)-78 | (Ia) | (1f) | (2aa) | (3c) | (4lll) | (1)-155 | (Ic) | (1a) | (2aa) | (3c) | (4cc) |
| (1)-79 | (Ia) | (1a) | (2aa) | (3c) | (4qqq) | (1)-156 | (Ic) | (1f) | (2aa) | (3c) | (4cc) |
| (1)-80 | (Ia) | (1f) | (2aa) | (3c) | (4qqq) | (1)-157 | (Ic) | (1a) | (2aa) | (3c) | (4lll) |
| (1)-81 | (Ib) | (1a) | (2a) | (3c) | (4a) | (1)-158 | (Ic) | (1f) | (2aa) | (3c) | (4lll) |
| (1)-82 | (Ib) | (1f) | (2a) | (3c) | (4a) | (1)-159 | (Ic) | (1a) | (2aa) | (3c) | (4qqq) |
| (1)-83 | (Ib) | (1a) | (2a) | (3c) | (4o) | (1)-160 | (Ic) | (1f) | (2aa) | (3c) | (4qqq) |
| (1)-84 | (Ib) | (1f) | (2a) | (3c) | (4o) | (1)-161 | (Id) | (1a) | (2a) | (3c) | (4a) |
| (1)-85 | (Ib) | (1a) | (2a) | (3c) | (4cc) | (1)-162 | (Id) | (1f) | (2a) | (3c) | (4a) |
| (1)-86 | (Ib) | (1f) | (2a) | (3c) | (4cc) | (1)-163 | (Id) | (1a) | (2a) | (3c) | (4o) |
| (1)-87 | (Ib) | (1a) | (2a) | (3c) | (4lll) | (1)-164 | (Id) | (1f) | (2a) | (3c) | (4o) |
| (1)-88 | (Ib) | (1f) | (2a) | (3c) | (4lll) | (1)-165 | (Id) | (1a) | (2a) | (3c) | (4cc) |
| (1)-89 | (Ib) | (1a) | (2a) | (3c) | (4qqq) | (1)-166 | (Id) | (1f) | (2a) | (3c) | (4cc) |
| (1)-90 | (Ib) | (1f) | (2a) | (3c) | (4qqq) | (1)-167 | (Id) | (1a) | (2a) | (3c) | (4lll) |
| (1)-91 | (Ib) | (1a) | (2k) | (3c) | (4a) | (1)-168 | (Id) | (1f) | (2a) | (3c) | (4lll) |
| (1)-92 | (Ib) | (1f) | (2k) | (3c) | (4a) | (1)-169 | (Id) | (1a) | (2a) | (3c) | (4qqq) |
| (1)-93 | (Ib) | (1a) | (2k) | (3c) | (4o) | (1)-170 | (Id) | (1f) | (2a) | (3c) | (4qqq) |
| (1)-94 | (Ib) | (1f) | (2k) | (3c) | (4o) | (1)-171 | (Id) | (1a) | (2k) | (3c) | (4a) |
| (1)-95 | (Ib) | (1a) | (2k) | (3c) | (4cc) | (1)-172 | (Id) | (1f) | (2k) | (3c) | (4a) |
| (1)-96 | (Ib) | (1f) | (2k) | (3c) | (4cc) | (1)-173 | (Id) | (1a) | (2k) | (3c) | (4o) |
| (1)-97 | (Ib) | (1a) | (2k) | (3c) | (4lll) | (1)-174 | (Id) | (1f) | (2k) | (3c) | (4o) |
| (1)-98 | (Ib) | (1f) | (2k) | (3c) | (4lll) | (1)-175 | (Id) | (1a) | (2k) | (3c) | (4cc) |
| (1)-99 | (Ib) | (1a) | (2k) | (3c) | (4qqq) | (1)-176 | (Id) | (1f) | (2k) | (3c) | (4cc) |
| (1)-100 | (Ib) | (1f) | (2k) | (3c) | (4qqq) | (1)-177 | (Id) | (1a) | (2k) | (3c) | (4lll) |
| (1)-101 | (Ib) | (1a) | (2z) | (3c) | (4a) | (1)-178 | (Id) | (1f) | (2k) | (3c) | (4lll) |
| (1)-102 | (Ib) | (1f) | (2z) | (3c) | (4a) | (1)-179 | (Id) | (1a) | (2k) | (3c) | (4qqq) |
| (1)-103 | (Ib) | (1a) | (2z) | (3c) | (4o) | (1)-180 | (Id) | (1f) | (2k) | (3c) | (4qqq) |
| (1)-104 | (Ib) | (1f) | (2z) | (3c) | (4o) | (1)-181 | (Id) | (1a) | (2z) | (3c) | (4a) |
| (1)-105 | (Ib) | (1a) | (2z) | (3c) | (4cc) | (1)-182 | (Id) | (1f) | (2z) | (3c) | (4a) |

| (I) | n | R¹ | R² | Z |
|---|---|---|---|---|
| (1)-183 | (Id) | (1a) | (2z) | (3c) | (4o) |
| (1)-184 | (Id) | (1f) | (2z) | (3c) | (4o) |
| (1)-185 | (Id) | (1a) | (2z) | (3c) | (4cc) |
| (1)-186 | (Id) | (1f) | (2z) | (3c) | (4cc) |
| (1)-187 | (Id) | (1a) | (2z) | (3c) | (4lll) |
| (1)-188 | (Id) | (1f) | (2z) | (3c) | (4lll) |
| (1)-189 | (Id) | (1a) | (2z) | (3c) | (4qqq) |
| (1)-190 | (Id) | (1f) | (2z) | (3c) | (4qqq) |
| (1)-191 | (Id) | (1a) | (2aa) | (3c) | (4a) |
| (1)-192 | (Id) | (1f) | (2aa) | (3c) | (4a) |
| (1)-193 | (Id) | (1a) | (2aa) | (3c) | (4o) |
| (1)-194 | (Id) | (1f) | (2aa) | (3c) | (4o) |
| (1)-195 | (Id) | (1a) | (2aa) | (3c) | (4cc) |
| (1)-196 | (Id) | (1f) | (2aa) | (3c) | (4cc) |
| (1)-197 | (Id) | (1a) | (2aa) | (3c) | (4lll) |
| (1)-198 | (Id) | (1f) | (2aa) | (3c) | (4lll) |
| (1)-199 | (Id) | (1a) | (2aa) | (3c) | (4qqq) |
| (1)-200 | (Id) | (1f) | (2aa) | (3c) | (4qqq) |
| (1)-201 | (Ie) | (1a) | (2a) | absent | (4a) |
| (1)-202 | (Ie) | (1f) | (2a) | absent | (4a) |
| (1)-203 | (Ie) | (1a) | (2a) | absent | (4o) |
| (1)-204 | (Ie) | (1f) | (2a) | absent | (4o) |
| (1)-205 | (Ie) | (1a) | (2a) | absent | (4cc) |
| (1)-206 | (Ie) | (1f) | (2a) | absent | (4cc) |
| (1)-207 | (Ie) | (1a) | (2a) | absent | (4lll) |
| (1)-208 | (Ie) | (1f) | (2a) | absent | (4lll) |
| (1)-209 | (Ie) | (1a) | (2a) | absent | (4qqq) |
| (1)-210 | (Ie) | (1f) | (2a) | absent | (4qqq) |
| (1)-211 | (Ie) | (1a) | (2k) | absent | (4a) |
| (1)-212 | (Ie) | (1f) | (2k) | absent | (4a) |
| (1)-213 | (Ie) | (1a) | (2k) | absent | (4o) |
| (1)-214 | (Ie) | (1f) | (2k) | absent | (4o) |
| (1)-215 | (Ie) | (1a) | (2k) | absent | (4cc) |
| (1)-216 | (Ie) | (1f) | (2k) | absent | (4cc) |
| (1)-217 | (Ie) | (1a) | (2k) | absent | (4lll) |
| (1)-218 | (Ie) | (1f) | (2k) | absent | (4lll) |
| (1)-219 | (Ie) | (1a) | (2k) | absent | (4qqq) |
| (1)-220 | (Ie) | (1f) | (2k) | absent | (4qqq) |
| (1)-221 | (Ie) | (1a) | (2z) | absent | (4a) |
| (1)-222 | (Ie) | (1f) | (2z) | absent | (4a) |
| (1)-223 | (Ie) | (1a) | (2z) | absent | (4o) |
| (1)-224 | (Ie) | (1f) | (2z) | absent | (4o) |
| (1)-225 | (Ie) | (1a) | (2z) | absent | (4cc) |
| (1)-226 | (Ie) | (1f) | (2z) | absent | (4cc) |
| (1)-227 | (Ie) | (1a) | (2z) | absent | (4lll) |
| (1)-228 | (Ie) | (1f) | (2z) | absent | (4lll) |
| (1)-229 | (Ie) | (1a) | (2z) | absent | (4qqq) |
| (1)-230 | (Ie) | (1f) | (2z) | absent | (4qqq) |
| (1)-231 | (Ie) | (1a) | (2aa) | absent | (4a) |
| (1)-232 | (Ie) | (1f) | (2aa) | absent | (4a) |
| (1)-233 | (Ie) | (1a) | (2aa) | absent | (4o) |
| (1)-234 | (Ie) | (1f) | (2aa) | absent | (4o) |
| (1)-235 | (Ie) | (1a) | (2aa) | absent | (4cc) |
| (1)-236 | (Ie) | (1f) | (2aa) | absent | (4cc) |
| (1)-237 | (Ie) | (1a) | (2aa) | absent | (4lll) |
| (1)-238 | (Ie) | (1f) | (2aa) | absent | (4lll) |
| (1)-239 | (Ie) | (1a) | (2aa) | absent | (4qqq) |
| (1)-240 | (Ie) | (1f) | (2aa) | absent | (4qqq) |
| (1)-241 | (If) | (1a) | (2a) | absent | (4a) |
| (1)-242 | (If) | (1f) | (2a) | absent | (4a) |
| (1)-243 | (If) | (1a) | (2a) | absent | (4o) |
| (1)-244 | (If) | (1f) | (2a) | absent | (4o) |
| (1)-245 | (If) | (1a) | (2a) | absent | (4cc) |
| (1)-246 | (If) | (1f) | (2a) | absent | (4cc) |
| (1)-247 | (If) | (1a) | (2a) | absent | (4lll) |
| (1)-248 | (If) | (1f) | (2a) | absent | (4lll) |
| (1)-249 | (If) | (1a) | (2a) | absent | (4qqq) |
| (1)-250 | (If) | (1f) | (2a) | absent | (4qqq) |
| (1)-251 | (If) | (1a) | (2k) | absent | (4a) |
| (1)-252 | (If) | (1f) | (2k) | absent | (4a) |
| (1)-253 | (If) | (1a) | (2k) | absent | (4o) |
| (1)-254 | (If) | (1f) | (2k) | absent | (4o) |
| (1)-255 | (If) | (1a) | (2k) | absent | (4cc) |
| (1)-256 | (If) | (1f) | (2k) | absent | (4cc) |
| (1)-257 | (If) | (1a) | (2k) | absent | (4lll) |
| (1)-258 | (If) | (1f) | (2k) | absent | (4lll) |
| (1)-259 | (If) | (1a) | (2k) | absent | (4qqq) |
| (1)-260 | (If) | (1f) | (2k) | absent | (4qqq) |
| (1)-261 | (If) | (1a) | (2z) | absent | (4a) |
| (1)-262 | (If) | (1f) | (2z) | absent | (4a) |
| (1)-263 | (If) | (1a) | (2z) | absent | (4o) |
| (1)-264 | (If) | (1f) | (2z) | absent | (4o) |
| (1)-265 | (If) | (1a) | (2z) | absent | (4cc) |
| (1)-266 | (If) | (1f) | (2z) | absent | (4cc) |
| (1)-267 | (If) | (1a) | (2z) | absent | (4lll) |
| (1)-268 | (If) | (1f) | (2z) | absent | (4lll) |
| (1)-269 | (If) | (1a) | (2z) | absent | (4qqq) |
| (1)-270 | (If) | (1f) | (2z) | absent | (4qqq) |
| (1)-271 | (If) | (1a) | (2aa) | absent | (4a) |
| (1)-272 | (If) | (1f) | (2aa) | absent | (4a) |
| (1)-273 | (If) | (1a) | (2aa) | absent | (4o) |
| (1)-274 | (If) | (1f) | (2aa) | absent | (4o) |
| (1)-275 | (If) | (1a) | (2aa) | absent | (4cc) |
| (1)-276 | (If) | (1f) | (2aa) | absent | (4cc) |
| (1)-277 | (If) | (1a) | (2aa) | absent | (4lll) |
| (1)-278 | (If) | (1f) | (2aa) | absent | (4lll) |
| (1)-279 | (If) | (1a) | (2aa) | absent | (4qqq) |
| (1)-280 | (If) | (1f) | (2aa) | absent | (4qqq) |
| (1)-281 | (Ig) | (1a) | (2a) | absent | (4a) |
| (1)-282 | (Ig) | (1f) | (2a) | absent | (4a) |
| (1)-283 | (Ig) | (1a) | (2a) | absent | (4o) |
| (1)-284 | (Ig) | (1f) | (2a) | absent | (4o) |
| (1)-285 | (Ig) | (1a) | (2a) | absent | (4cc) |
| (1)-286 | (Ig) | (1f) | (2a) | absent | (4cc) |
| (1)-287 | (Ig) | (1a) | (2a) | absent | (4lll) |
| (1)-288 | (Ig) | (1f) | (2a) | absent | (4lll) |
| (1)-289 | (Ig) | (1a) | (2a) | absent | (4qqq) |
| (1)-290 | (Ig) | (1f) | (2a) | absent | (4qqq) |
| (1)-291 | (Ig) | (1a) | (2k) | absent | (4a) |
| (1)-292 | (Ig) | (1f) | (2k) | absent | (4a) |
| (1)-293 | (Ig) | (1a) | (2k) | absent | (4o) |
| (1)-294 | (Ig) | (1f) | (2k) | absent | (4o) |
| (1)-295 | (Ig) | (1a) | (2k) | absent | (4cc) |
| (1)-296 | (Ig) | (1f) | (2k) | absent | (4cc) |
| (1)-297 | (Ig) | (1a) | (2k) | absent | (4lll) |
| (1)-298 | (Ig) | (1f) | (2k) | absent | (4lll) |
| (1)-299 | (Ig) | (1a) | (2k) | absent | (4qqq) |
| (1)-300 | (Ig) | (1f) | (2k) | absent | (4qqq) |
| (1)-301 | (Ig) | (1a) | (2z) | absent | (4a) |
| (1)-302 | (Ig) | (1f) | (2z) | absent | (4a) |
| (1)-303 | (Ig) | (1a) | (2z) | absent | (4o) |
| (1)-304 | (Ig) | (1f) | (2z) | absent | (4o) |
| (1)-305 | (Ig) | (1a) | (2z) | absent | (4cc) |
| (1)-306 | (Ig) | (1f) | (2z) | absent | (4cc) |
| (1)-307 | (Ig) | (1a) | (2z) | absent | (4lll) |
| (1)-308 | (Ig) | (1f) | (2z) | absent | (4lll) |
| (1)-309 | (Ig) | (1a) | (2z) | absent | (4qqq) |
| (1)-310 | (Ig) | (1f) | (2z) | absent | (4qqq) |
| (1)-311 | (Ig) | (1a) | (2aa) | absent | (4a) |
| (1)-312 | (Ig) | (1f) | (2aa) | absent | (4a) |
| (1)-313 | (Ig) | (1a) | (2aa) | absent | (4o) |
| (1)-314 | (Ig) | (1f) | (2aa) | absent | (4o) |
| (1)-315 | (Ig) | (1a) | (2aa) | absent | (4cc) |
| (1)-316 | (Ig) | (1f) | (2aa) | absent | (4cc) |
| (1)-317 | (Ig) | (1a) | (2aa) | absent | (4lll) |
| (1)-318 | (Ig) | (1f) | (2aa) | absent | (4lll) |
| (1)-319 | (Ig) | (1a) | (2aa) | absent | (4qqq) |
| (1)-320 | (Ig) | (1f) | (2aa) | absent | (4qqq) |

The invention further comprises subgenera of formula (I) in which structural formula (I), p and $R^2$, and Z are independently selected from the groups (Ii) et seq., (1a) et seq., (2a) et seq., and (3a) et seq. defined hereinbelow (e.g., wherein the compound is of structural formula (I) as defined in any of the above embodiments:

Structural Formula (I) is One of Formulae (Ii)-(Ip):

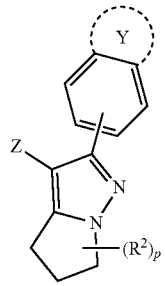
(Ii)

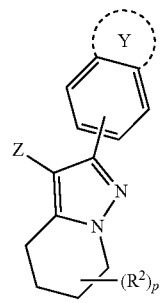
(Ij)

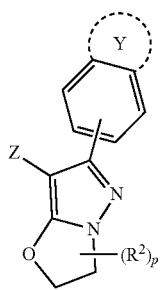
(Ik)

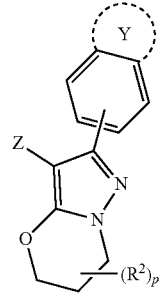
(Il)

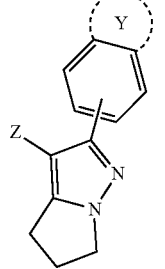
(Im)

-continued

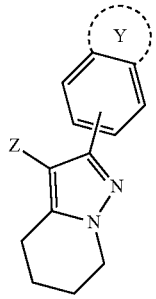
(In)

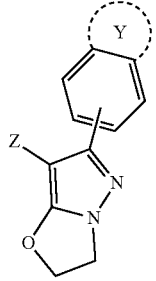
(Io)

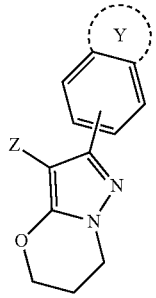
(Ip)

Y is Selected from One of the Following Groups (5a)-(5e):

(5a) Y is an optionally substituted 5- to 9-membered Hca group.

(5b) Y is an optionally substituted 5- to 6-membered Hca group.

(5c) Y is unsubstituted 5- to 9-membered Hca group.

(5d) Y is unsubstituted 5- to 6-membered Hca group.

(5e) Y is

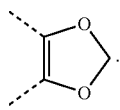

Particular embodiments of this aspect of the invention comprise compounds of any one of the formulae (I) and (Ii)-(Ip), each as defined in each of the following rows (or a pharmaceutically acceptable salt, prodrug, or N-oxide thereof, or a solvate or hydrate thereof), wherein each entry is a group number as defined above, and a dash "-" indicates that the variable is as defined in any one of embodiments $I_1$-$I_5$ or defined according to any one of the applicable variable definitions (Ii)-(Ip), (3a)-(3o), and (4a)-(4sss):

| (I) | R² | Z | Y |
|---|---|---|---|
| (1)-321 | (I) | (3a) | (4a) | (5b) |
| (1)-322 | (I) | (3a) | (4a) | (5e) |
| (1)-323 | (I) | (3a) | (4o) | (5b) |
| (1)-324 | (I) | (3a) | (4o) | (5e) |
| (1)-325 | (I) | (3a) | (4cc) | (5b) |
| (1)-326 | (I) | (3a) | (4cc) | (5e) |
| (1)-327 | (I) | (3a) | (4lll) | (5b) |
| (1)-328 | (I) | (3a) | (4lll) | (5e) |
| (1)-329 | (I) | (3a) | (4qqq) | (5b) |
| (1)-330 | (I) | (3a) | (4qqq) | (5e) |
| (1)-331 | (Ii) | (3a) | (4a) | (5b) |
| (1)-332 | (Ii) | (3a) | (4a) | (5e) |
| (1)-333 | (Ii) | (3a) | (4o) | (5b) |
| (1)-334 | (Ii) | (3a) | (4o) | (5e) |
| (1)-335 | (Ii) | (3a) | (4cc) | (5b) |
| (1)-336 | (Ii) | (3a) | (4cc) | (5e) |
| (1)-337 | (Ii) | (3a) | (4lll) | (5b) |
| (1)-338 | (Ii) | (3a) | (4lll) | (5e) |
| (1)-339 | (Ii) | (3a) | (4qqq) | (5b) |
| (1)-340 | (Ii) | (3a) | (4qqq) | (5e) |
| (1)-341 | (Im) | absent | (4a) | (5b) |
| (1)-342 | (Im) | absent | (4a) | (5e) |
| (1)-343 | (Im) | absent | (4o) | (5b) |
| (1)-344 | (Im) | absent | (4o) | (5e) |
| (1)-345 | (Im) | absent | (4cc) | (5b) |
| (1)-346 | (Im) | absent | (4cc) | (5e) |
| (1)-347 | (Im) | absent | (4lll) | (5b) |
| (1)-348 | (Im) | absent | (4lll) | (5e) |
| (1)-349 | (Im) | absent | (4qqq) | (5b) |
| (1)-350 | (Im) | absent | (4qqq) | (5e) |
| (1)-351 | (Io) | absent | (4a) | (5b) |
| (1)-352 | (Io) | absent | (4a) | (5e) |
| (1)-353 | (Io) | absent | (4o) | (5b) |
| (1)-354 | (Io) | absent | (4o) | (5e) |
| (1)-355 | (Io) | absent | (4cc) | (5b) |
| (1)-356 | (Io) | absent | (4cc) | (5e) |
| (1)-357 | (Io) | absent | (4lll) | (5b) |
| (1)-358 | (Io) | absent | (4lll) | (5e) |
| (1)-359 | (Io) | absent | (4qqq) | (5b) |
| (1)-360 | (Io) | absent | (4qqq) | (5e) |

In some embodiments, the compound of formula (I) is one of the following compounds (or a pharmaceutically acceptable salt, prodrug, or N-oxide thereof, or a solvate or hydrate thereof):

| No. | Structure | Name |
|---|---|---|
| 1 | 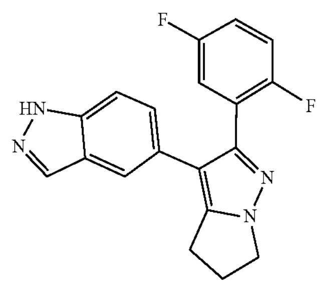 [SMILES: Fc1ccc(F)c(-c2nn3c(c2-c2ccc4[nH]ncc4c2)CCC3)c1] | 5-(2-(2,5-difluorophenyl)-5,6-dihydro-4H-pyrrolo[1,2-b]pyrazol-3-yl)-1H-indazole |
| 2 | 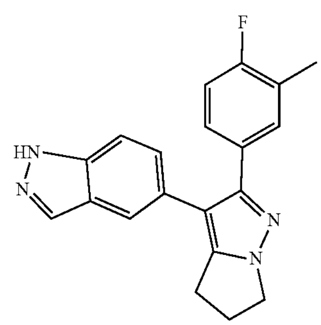 [SMILES: Cc1cc(-c2nn3c(c2-c2ccc4[nH]ncc4c2)CCC3)ccc1F] | 5-(2-(4-Fluoro-3-methylphenyl)-5,6-dihydro-4H-pyrrolo[1,2-b]pyrazol-3-yl)-1H-indazole |
| 3 | 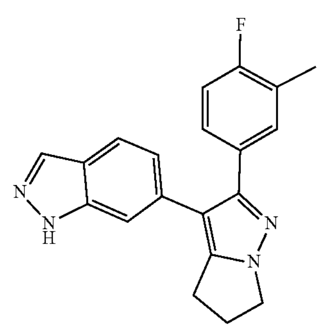 [SMILES: Cc1cc(-c2nn3c(c2-c2ccc4cn[nH]c4c2)CCC3)ccc1F] | 6-(2-(4-Fluoro-3-methylphenyl)-5,6-dihydro-4H-pyrrolo[1,2-b]pyrazol-3-yl)-1H-indazole |

| No. | Structure | Name |
|---|---|---|
| 4 | 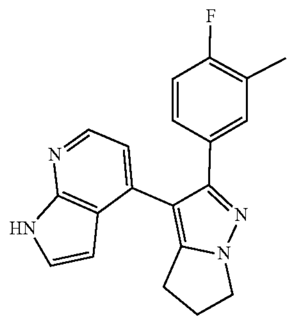 [SMILES: Cc1cc(-c2nn3c(c2-c2ccnc4[nH]ccc24)CCC3)ccc1F] | 4-(2-(4-Fluoro-3-methylphenyl)-5,6-dihydro-4H-pyrrolo[1,2-b]pyrazol-3-yl)-1H-pyrrolo[2,3-b]pyridine |
| 5 | 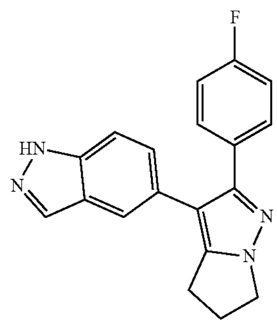 [SMILES: Fc1ccc(-c2nn3c(c2-c2ccc4[nH]ncc4c2)CCC3)cc1] | 5-(2-(4-Fluorophenyl)-5,6-dihydro-4H-pyrrolo[1,2-b]pyrazol-3-yl)-1H-indazole |
| 6 | 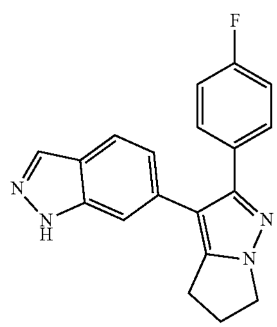 [SMILES: Fc1ccc(-c2nn3c(c2-c2ccc4cn[nH]c4c2)CCC3)cc1] | 6-(2-(4-Fluorophenyl)-5,6-dihydro-4H-pyrrolo[1,2-b]pyrazol-3-yl)-1H-indazole |
| 7 | 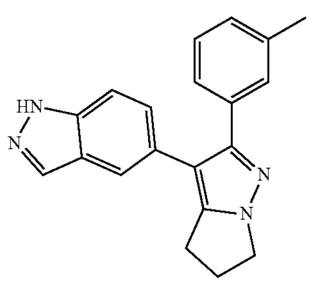 [SMILES: Cc1cccc(-c2nn3c(c2-c2ccc4[nH]ncc4c2)CCC3)c1] | 5-(2-(m-Tolyl)-5,6-dihydro-4H-pyrrolo[1,2-b]pyrazol-3-yl)-1H-indazole |
| 8 | 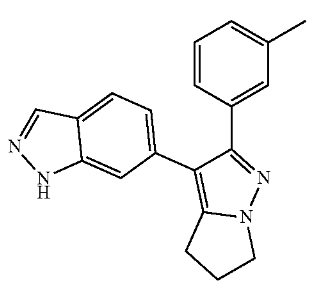 [SMILES: Cc1cccc(-c2nn3c(c2-c2ccc4cn[nH]c4c2)CCC3)c1] | 6-(2-(m-Tolyl)-5,6-dihydro-4H-pyrrolo[1,2-b]pyrazol-3-yl)-1H-indazole |

| No. | Structure | Name |
|---|---|---|
| 9 | 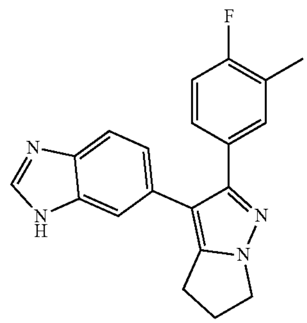 [SMILES: Cc1cc(-c2nn3c(c2-c2ccc4nc[nH]c4c2)CCC3)ccc1F] | 6-(2-(4-Fluoro-3-methylphenyl)-5,6-dihydro-4H-pyrrolo[1,2-b]pyrazol-3-yl)-1H-benzo[d]imidazole |
| 10 | 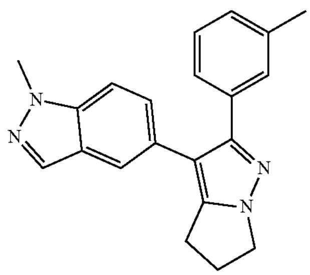 [SMILES: Cc1cccc(-c2nn3c(c2-c2ccc4c(cnn4C)c2)CCC3)c1] | 1-Methyl-5-(2-(m-tolyl)-5,6-dihydro-4H-pyrrolo[1,2-b]pyrazol-3-yl)-1H-indazole |
| 11 | 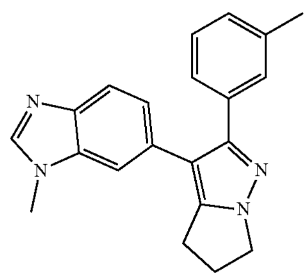 [SMILES: Cc1cccc(-c2nn3c(c2-c2ccc4ncn(C)c4c2)CCC3)c1] | 1-Methyl-6-(2-(m-tolyl)-5,6-dihydro-4H-pyrrolo[1,2-b]pyrazol-3-yl)-1H-benzo[d]imidazole |
| 12 | 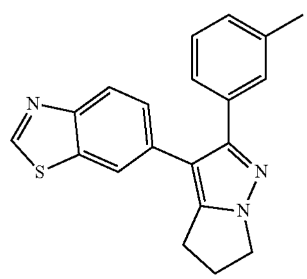 [SMILES: Cc1cccc(-c2nn3c(c2-c2ccc4ncsc4c2)CCC3)c1] | 6-(2-(m-Tolyl)-5,6-dihydro-4H-pyrrolo[1,2-b]pyrazol-3-yl)benzo[d]thiazole |
| 13 | 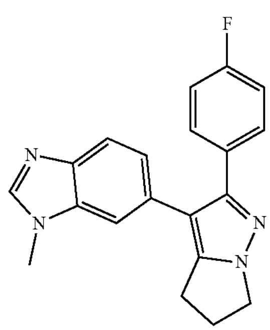 [SMILES: Cn1cnc2ccc(-c3c(-c4ccc(F)cc4)nn4c3CCC4)cc21] | 6-(2-(4-Fluorophenyl)-5,6-dihydro-4H-pyrrolo[1,2-b]pyrazol-3-yl)-1-methyl-1H-benzo[d]imidazole |

-continued

| No. | Structure | Name |
|---|---|---|
| 14 | 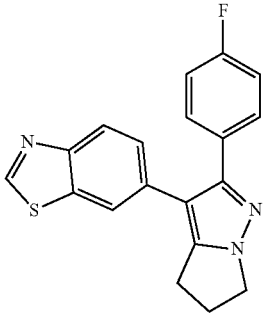 [SMILES: Fc1ccc(-c2nn3c(c2-c2ccc4ncsc4c2)CCC3)cc1] | 6-(2-(4-Fluorophenyl)-5,6-dihydro-4H-pyrrolo[1,2-b]pyrazol-3-yl)benzo[d]thiazole |
| 15 | 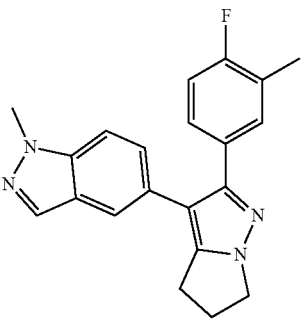 [SMILES: Cc1cc(-c2nn3c(c2-c2ccc4c(cnn4C)c2)CCC3)ccc1F] | 5-(2-(4-Fluoro-3-methylphenyl)-5,6-dihydro-4H-pyrrolo[1,2-b]pyrazol-3-yl)-1-methyl-1H-indazole |
| 16 | 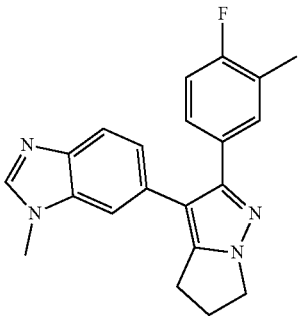 [SMILES: Cc1cc(-c2nn3c(c2-c2ccc4ncn(C)c4c2)CCC3)ccc1F] | 6-(2-(4-Fluoro-3-methylphenyl)-5,6-dihydro-4H-pyrrolo[1,2-b]pyrazol-3-yl)-1-methyl-1H-benzo[d]imidazole |
| 17 | 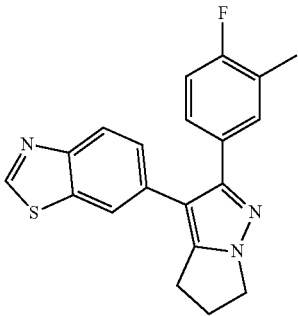 [SMILES: Cc1cc(-c2nn3c(c2-c2ccc4ncsc4c2)CCC3)ccc1F] | 6-(2-(4-Fluoro-3-methylphenyl)-5,6-dihydro-4H-pyrrolo[1,2-b]pyrazol-3-yl)benzo[d]thiazole |
| 18 | 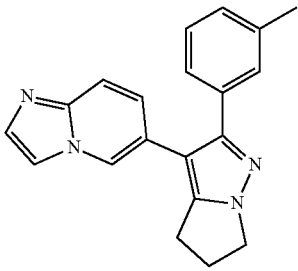 [SMILES: Cc1cccc(-c2nn3c(c2-c2ccc4nccn4c2)CCC3)c1] | 6-(2-(m-Tolyl)-5,6-dihydro-4H-pyrrolo[1,2-b]pyrazol-3-yl)imidazo[1,2-a]pyridine |

-continued
| No. | Structure | Name |
|---|---|---|
| 19 | 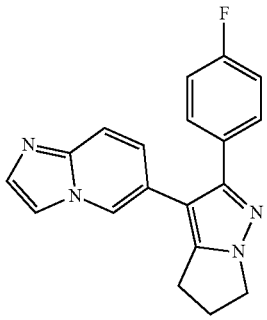 | 6-(2-(4-Fluorophenyl)-5,6-dihydro-4H-pyrrolo[1,2-b]pyrazol-3-yl)imidazo[1,2-a]pyridine |
| 20 | 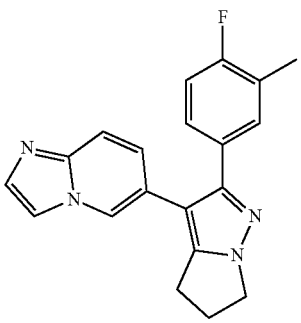 [SMILES: Cc1cc(-c2nn3c(c2-c2ccc4nccn4c2)CCC3)ccc1F] | 6-(2-(4-Fluoro-3-methylphenyl)-5,6-dihydro-4H-pyrrolo[1,2-b]pyrazol-3-yl)imidazo[1,2-a]pyridine |
| 21 | 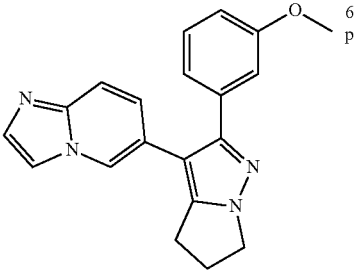 | 6-(2-(3-Methoxyphenyl)-5,6-dihydro-4H-pyrrolo[1,2-b]pyrazol-3-yl)imidazo[1,2-a]pyridine |
| 22 | 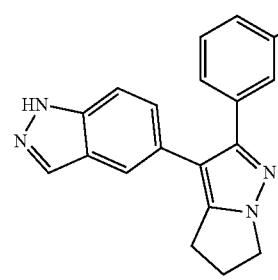 | 5-(2-(3-Chlorophenyl)-5,6-dihydro-4H-pyrrolo[1,2-b]pyrazol-3-yl)-1H-indazole |
| 23 | 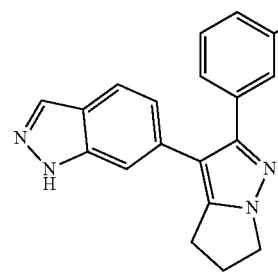 | 6-(2-(3-Chlorophenyl)-5,6-dihydro-4H-pyrrolo[1,2-b]pyrazol-3-yl)-1H-indazole |

-continued
| No. | Structure | Name |
|---|---|---|
| 24 | 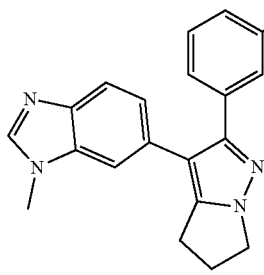 | 6-(2-(3-Chlorophenyl)-5,6-dihydro-4H-pyrrolo[1,2-b]pyrazol-3-yl)-1-methyl-1H-benzo[d]imidazole |
| 25 | 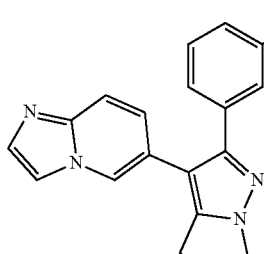 | 6-(2-(3-Chlorophenyl)-5,6-dihydro-4H-pyrrolo[1,2-b]pyrazol-3-yl)imidazo[1,2-a]pyridine |
| 26 | 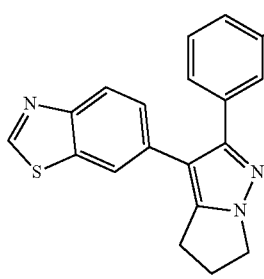 | 6-(2-(3-Chlorophenyl)-5,6-dihydro-4H-pyrrolo[1,2-b]pyrazol-3-yl)benzo[d]thiazole |
| 27 | 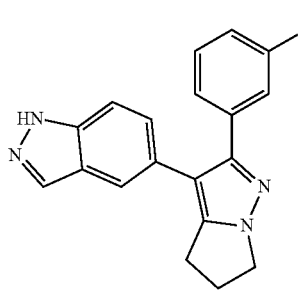 | 5-(2-(3-Methoxyphenyl)-5,6-dihydro-4H-pyrrolo[1,2-b]pyrazol-3-yl)-1H-indazole |
| 28 | 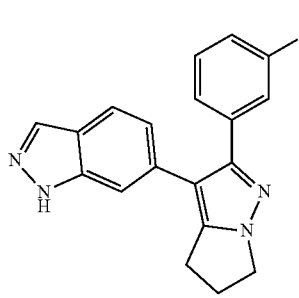 | 6-(2-(3-Methoxyphenyl)-5,6-dihydro-4H-pyrrolo[1,2-b]pyrazol-3-yl)-1H-indazole |

-continued

| No. | Structure | Name |
|---|---|---|
| 29 | 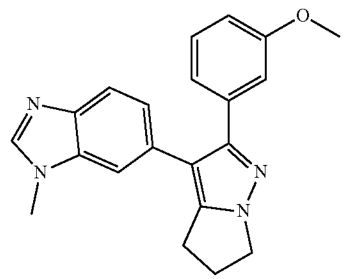 [SMILES: COc1cccc(-c2nn3c(c2-c2ccc4ncn(C)c4c2)CCC3)c1] | 6-(2-(3-Methoxyphenyl)-5,6-dihydro-4H-pyrrolo[1,2-b]pyrazol-3-yl)-1-methyl-1H-benzo[d]imidazole |
| 30 | 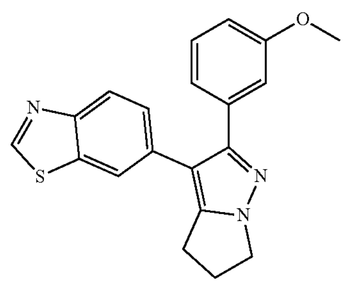 [SMILES: COc1cccc(-c2nn3c(c2-c2ccc4ncsc4c2)CCC3)c1] | 6-(2-(3-Methoxyphenyl)-5,6-dihydro-4H-pyrrolo[1,2-b]pyrazol-3-yl)benzo[d]thiazole |
| 31 | 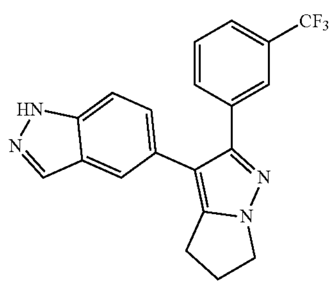 [SMILES: FC(F)(F)c1cccc(-c2nn3c(c2-c2ccc4[nH]ncc4c2)CCC3)c1] | 5-(2-(3-Trifluoromethylphenyl)-5,6-dihydro-4H-pyrrolo[1,2-b]pyrazol-3-yl)-1H-indazole |
| 32 | 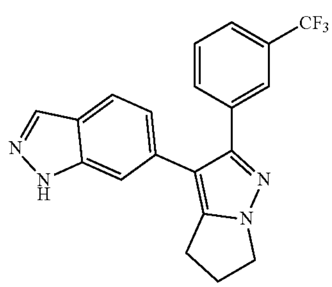 [SMILES: FC(F)(F)c1cccc(-c2nn3c(c2-c2ccc4cn[nH]c4c2)CCC3)c1] | 6-(2-(3-Trifluoromethylphenyl)-5,6-dihydro-4H-pyrrolo[1,2-b]pyrazol-3-yl)-1H-indazole |
| 33 | 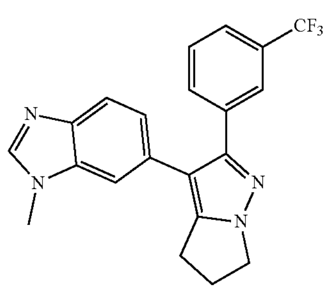 [SMILES: Cn1cnc2ccc(-c3c(-c4cccc(C(F)(F)F)c4)nn4c3CCC4)cc21] | 1-Methyl-6-(2-(3-trifluoromethylphenyl)-5,6-dihydro-4H-pyrrolo[1,2-b]pyrazol-3-yl)-1H-benzo[d]imidazole |

-continued

| No. | Structure | Name |
|---|---|---|
| 34 | 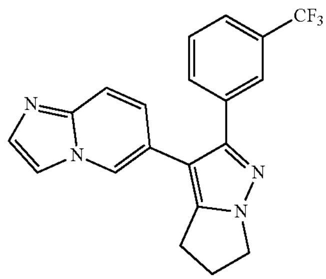 [SMILES: FC(F)(F)c1cccc(-c2nn3c(c2-c2ccc4nccn4c2)CCC3)c1] | 6-(2-(3-Trifluoromethylphenyl)-5,6-dihydro-4H-pyrrolo[1,2-b]pyrazol-3-yl)imidazo[1,2-a]pyridine |
| 35 | 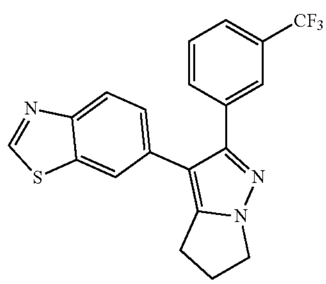 [SMILES: FC(F)(F)c1cccc(-c2nn3c(c2-c2ccc4ncsc4c2)CCC3)c1] | 6-(2-(3-Trifluoromethylphenyl)-5,6-dihydro-4H-pyrrolo[1,2-b]pyrazol-3-yl)benzo[d]thiazole |
| 36 | 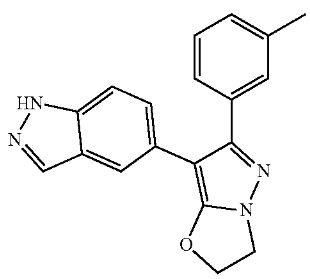 [SMILES: Cc1cccc(-c2nn3c(c2-c2ccc4[nH]ncc4c2)OCC3)c1] | 7-(1H-Indazol-5-yl)-6-(m-tolyl)-2,3-dihydropyrazolo[5,1-b]oxazole |
| 37 | 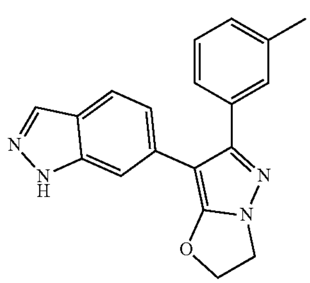 [SMILES: Cc1cccc(-c2nn3c(c2-c2ccc4cn[nH]c4c2)OCC3)c1] | 7-(1H-Indazol-6-yl)-6-(m-tolyl)-2,3-dihydropyrazolo[5,1-b]oxazole |
| 38 | 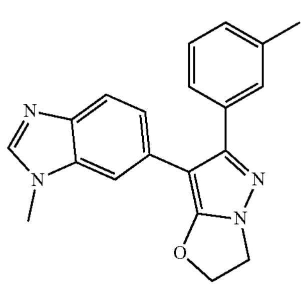 [SMILES: Cc1cccc(-c2nn3c(c2-c2ccc4ncn(C)c4c2)OCC3)c1] | 7-(1-Methyl-1H-benzo[d]imidazol-6-yl)-6-(m-tolyl)-2,3-dihydropyrazolo[5,1-b]oxazole |

-continued

| No. | Structure | Name |
|---|---|---|
| 39 | 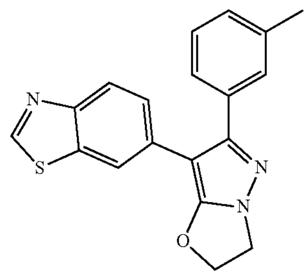 [SMILES: Cc1cccc(-c2nn3c(c2-c2ccc4ncsc4c2)OCC3)c1] | 7-(Benzo[d]thiazol-6-yl)-6-(m-tolyl)-2,3-dihydropyrazolo[5,1-b]oxazole |
| 40 | 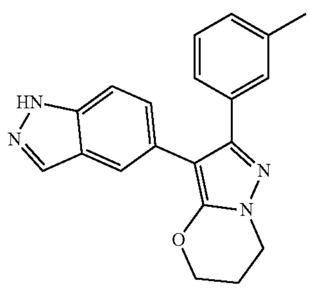 [SMILES: Cc1cccc(-c2nn3c(c2-c2ccc4[nH]ncc4c2)OCCC3)c1] | 3-(1H-Indazol-5-yl)-2-(m-tolyl)-6,7-dihydro-5H-pyrazolo[5,1-b][1,3]oxazine |
| 41 | 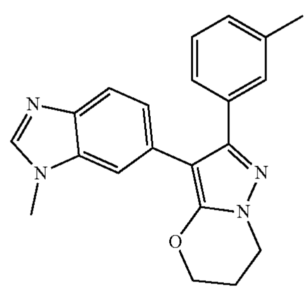 [SMILES: Cc1cccc(-c2nn3c(c2-c2ccc4ncn(C)c4c2)OCCC3)c1] | 3-(1-Methyl-1H-benzo[d]imidazol-6-yl)-2-(m-tolyl)-6,7-dihydro-5H-pyrazolo[5,1-b][1,3]oxazine |
| 42 | 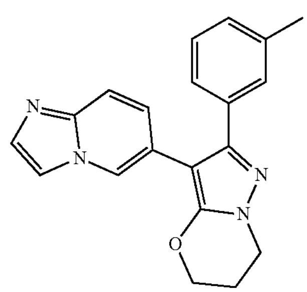 [SMILES: Cc1cccc(-c2nn3c(c2-c2ccc4nccn4c2)OCCC3)c1] | 3-(Imidazo[1,2-a]pyridin-6-yl)-2-(m-tolyl)-6,7-dihydro-5H-pyrazolo[5,1-b][1,3]oxazine |
| 43 | 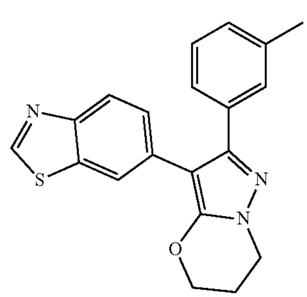 [SMILES: Cc1cccc(-c2nn3c(c2-c2ccc4ncsc4c2)OCCC3)c1] | 3-(benzo[d]thiazol-6-yl)-2-(m-tolyl)-6,7-dihydro-5H-pyrazolo[5,1-b][1,3]oxazine |

-continued

| No. | Structure | Name |
|---|---|---|
| 44 | 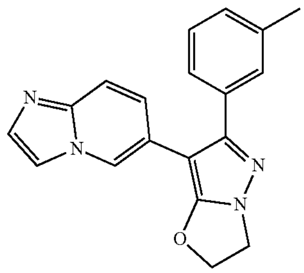 [SMILES: Cc1cccc(-c2nn3c(c2-c2ccc4nccn4c2)OCC3)c1] | 7-(imidazo[1,2-a]pyridin-6-yl)-6-(m-tolyl)-2,3-dihydropyrazolo[5,1-b]oxazole |
| 45 | 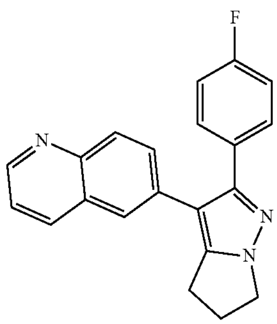 [SMILES: Fc1ccc(-c2nn3c(c2-c2ccc4ncccc4c2)CCC3)cc1] | 6-(2-(4-Fluorophenyl)-5,6-dihydro-4H-pyrrolo[1,2-b]pyrazol-3-yl)quinoline |
| 46 | 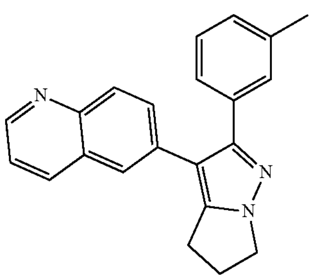 [SMILES: Cc1cccc(-c2nn3c(c2-c2ccc4ncccc4c2)CCC3)c1] | 6-(2-(m-Tolyl)-5,6-dihydro-4H-pyrrolo[1,2-b]pyrazol-3-yl)quinoline |
| 47 | 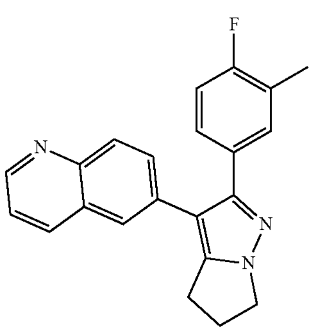 [SMILES: Cc1cc(-c2nn3c(c2-c2ccc4ncccc4c2)CCC3)ccc1F] | 6-(2-(4-Fluoro-3-methylphenyl)-5,6-dihydro-4H-pyrrolo[1,2-b]pyrazol-3-yl)quinoline |
| 48 | 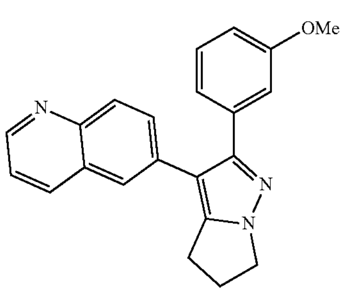 [SMILES: COc1cccc(-c2nn3c(c2-c2ccc4ncccc4c2)CCC3)c1] | 6-(2-(3-Methoxyphenyl)-5,6-dihydro-4H-pyrrolo[1,2-b]pyrazol-3-yl)quinoline |

-continued

| No. | Structure | Name |
|---|---|---|
| 49 | 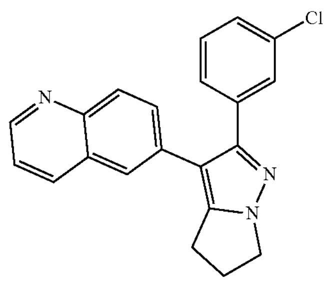 | 6-(2-(3-Chlorophenyl)-5,6-dihydro-4H-pyrrolo[1,2-b]pyrazol-3-yl)quinoline |
| 50 | 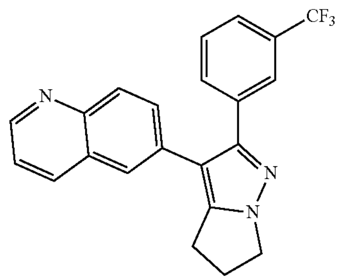 [SMILES: FC(F)(F)c1cccc(-c2nn3c(c2-c2ccc4ncccc4c2)CCC3)c1] | 6-(2-(3-Trifluoromethylphenyl)-5,6-dihydro-4H-pyrrolo[1,2-b]pyrazol-3-yl)quinoline |
| 51 | 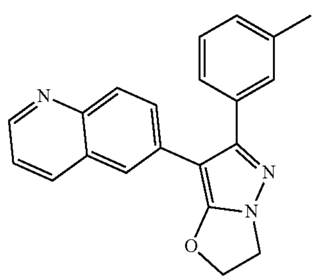 [SMILES: Cc1cccc(-c2nn3c(c2-c2ccc4ncccc4c2)OCC3)c1] | 7-(Quinolin-6-yl)-6-(m-tolyl)-2,3-dihydropyrazolo[5,1-b]oxazole |
| 52 | 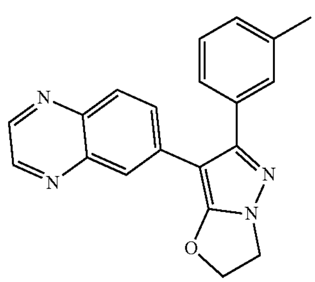 [SMILES: Cc1cccc(-c2nn3c(c2-c2ccc4nccnc4c2)OCC3)c1] | 7-(Quinoxalin-6-yl)-6-(m-tolyl)-2,3-dihydropyrazolo[5,1-b]oxazole |
| 53 | 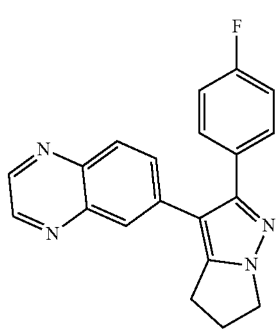 [SMILES: Fc1ccc(-c2nn3c(c2-c2ccc4nccnc4c2)CCC3)cc1] | 6-(2-(4-Fluorophenyl)-5,6-dihydro-4H-pyrrolo[1,2-b]pyrazol-3-yl)quinoxaline |

-continued

| No. | Structure | Name |
|---|---|---|
| 54 | 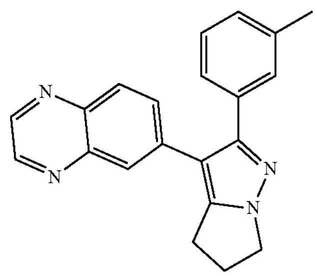 [SMILES: Cc1cccc(-c2nn3c(c2-c2ccc4nccnc4c2)CCC3)c1] | 6-(2-(m-Tolyl)-5,6-dihydro-4H-pyrrolo[1,2-b]pyrazol-3-yl)quinoxaline |
| 55 | 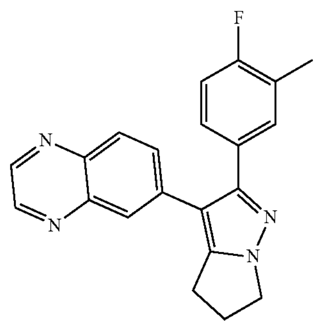 [SMILES: Cc1cc(-c2nn3c(c2-c2ccc4nccnc4c2)CCC3)ccc1F] | 6-(2-(4-Fluoro-3-methylphenyl)-5,6-dihydro-4H-pyrrolo[1,2-b]pyrazol-3-yl)quinoxaline |
| 56 | 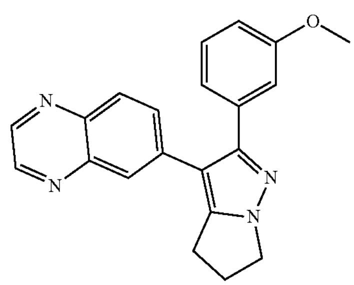 [SMILES: COc1cccc(-c2nn3c(c2-c2ccc4nccnc4c2)CCC3)c1] | 6-(2-(3-Methoxyphenyl)-5,6-dihydro-4H-pyrrolo[1,2-b]pyrazol-3-yl)quinoxaline |
| 57 | 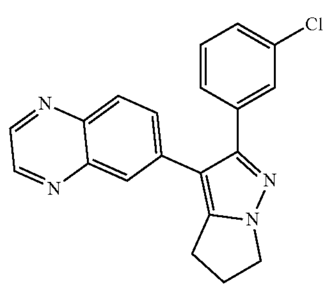 [SMILES: Clc1cccc(-c2nn3c(c2-c2ccc4nccnc4c2)CCC3)c1] | 6-(2-(3-Chlorophenyl)-5,6-dihydro-4H-pyrrolo[1,2-b]pyrazol-3-yl)quinoxaline |
| 58 | 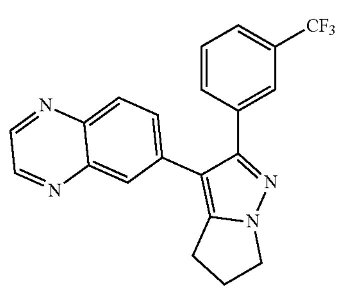 [SMILES: FC(F)(F)c1cccc(-c2nn3c(c2-c2ccc4nccnc4c2)CCC3)c1] | 6-(2-(3-Trifluoromethylphenyl)-5,6-dihydro-4H-pyrrolo[1,2-b]pyrazol-3-yl)quinoxaline |

-continued

| No. | Structure | Name |
|---|---|---|
| 59 | 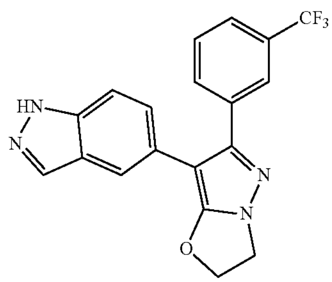 | 7-(1H-Indazol-5-yl)-6-(3-trifluoromethylphenyl)-2,3-dihydropyrazolo[5,1-b]oxazole |
| 60 | 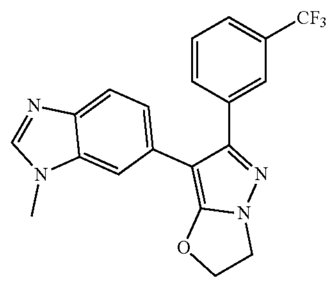 [SMILES: Cn1cnc2ccc(-c3c(-c4cccc(C(F)(F)F)c4)nn4c3OCC4)cc21] | 7-(1-Methyl-1H-benzo[d]imidazol-6-yl)-6-(3-trifluoromethylphenyl)-2,3-dihydropyrazolo[5,1-b]oxazole |
| 61 | 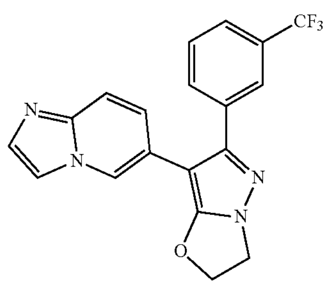 [SMILES: FC(F)(F)c1cccc(-c2nn3c(c2-c2ccc4nccn4c2)OCC3)c1] | 7-(Imidazo[1,2-a]pyridin-6-yl)-6-(3-trifluoromethylphenyl)-2,3-dihydropyrazolo[5,1-b]oxazole |
| 62 | 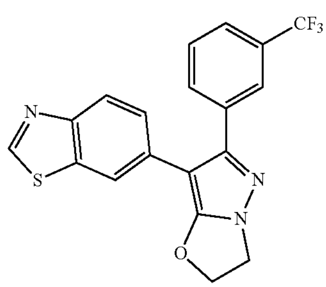 [SMILES: FC(F)(F)c1cccc(-c2nn3c(c2-c2ccc4ncsc4c2)OCC3)c1] | 7-(Benzo[d]thiazol-6-yl)-6-(3-trifluoromethylphenyl)-2,3-dihydropyrazolo[5,1-b]oxazole |
| 63 | 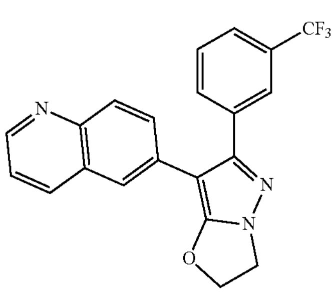 [SMILES: FC(F)(F)c1cccc(-c2nn3c(c2-c2ccc4ncccc4c2)OCC3)c1] | 7-(Quinolin-6-yl)-6-(3-trifluoromethylphenyl)-2,3-dihydropyrazolo[5,1-b]oxazole |

-continued

| No. | Structure | Name |
|---|---|---|
| 64 | 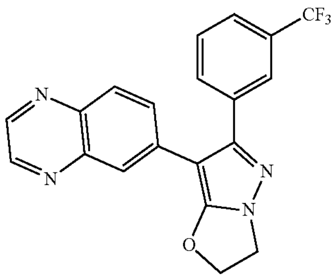 [SMILES: FC(F)(F)c1cccc(-c2nn3c(c2-c2ccc4nccnc4c2)OCC3)c1] | 7-(Quinoxalin-6-yl)-6-(3-trifluoromethylphenyl)-2,3-dihydropyrazolo[5,1-b]oxazole |
| 65 | 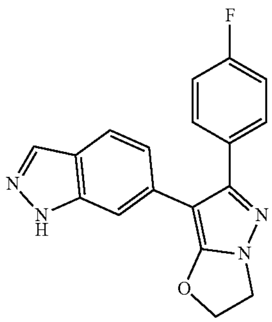 [SMILES: Fc1ccc(-c2nn3c(c2-c2ccc4cn[nH]c4c2)OCC3)cc1] | 6-(4-Fluorophenyl)-7-(1H-indazol-6-yl)-2,3-dihydropyrazolo[5,1-b]oxazole |
| 66 | 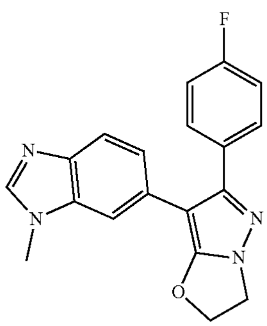 [SMILES: Cn1cnc2ccc(-c3c(-c4ccc(F)cc4)nn4c3OCC4)cc21] | 6-(4-Fluorophenyl)-7-(1-methyl-1H-benzo[d]imidazol-6-yl)-2,3-dihydropyrazolo[5,1-b]oxazole |
| 67 | 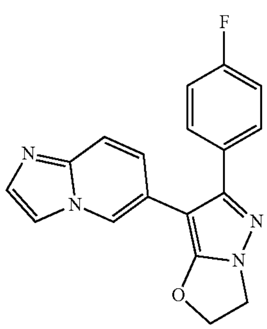 [SMILES: Fc1ccc(-c2nn3c(c2-c2ccc4nccn4c2)OCC3)cc1] | 6-(4-Fluorophenyl)-7-(imidazo[1,2-a]pyridin-6-yl)-2,3-dihydropyrazolo[5,1-b]oxazole |
| 68 | 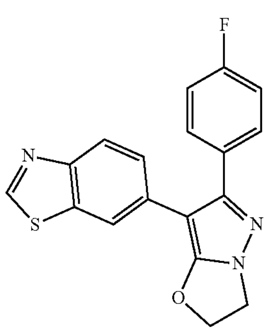 [SMILES: Fc1ccc(-c2nn3c(c2-c2ccc4ncsc4c2)OCC3)cc1] | 7-(Benzo[d]thiazol-6-yl)-6-(4-fluorophenyl)-2,3-dihydropyrazolo[5,1-b]oxazole |

-continued

| No. | Structure | Name |
|---|---|---|
| 69 | 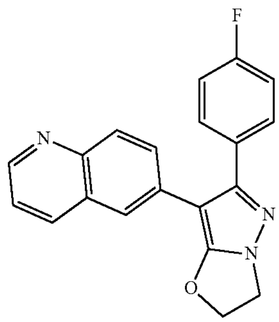 [SMILES: Fc1ccc(-c2nn3c(c2-c2ccc4ncccc4c2)OCC3)cc1] | 6-(4-Fluorophenyl)-7-(quinolin-6-yl)-2,3-dihydropyrazolo[5,1-b]oxazole |
| 70 | 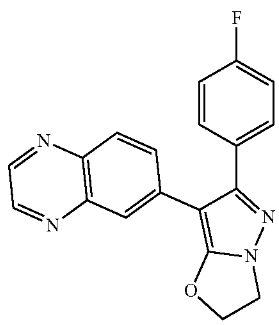 [SMILES: Fc1ccc(-c2nn3c(c2-c2ccc4nccnc4c2)OCC3)cc1] | 6-(4-Fluorophenyl)-7-(quinoxalin-6-yl)-2,3-dihydropyrazolo[5,1-b]oxazole |
| 71 | 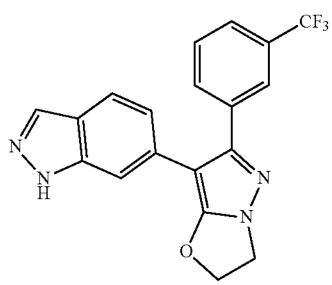 [SMILES: FC(F)(F)c1cccc(-c2nn3c(c2-c2ccc4cn[nH]c4c2)OCC3)c1] | 7-(1H-Indazol-6-yl)-6-(3-trifluoromethylphenyl)-2,3-dihydropyrazolo[5,1-b]oxazole |
| 72 | 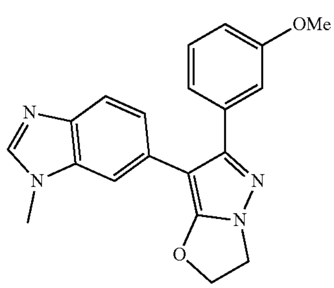 [SMILES: COc1cccc(-c2nn3c(c2-c2ccc4ncn(C)c4c2)OCC3)c1] | 6-(3-Methoxyphenyl)-7-(1-methyl-1H-benzo[d]imidazol-6-yl)-2,3-dihydropyrazolo[5,1-b]oxazole |
| 73 | 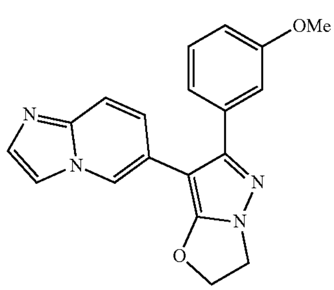 [SMILES: COc1cccc(-c2nn3c(c2-c2ccc4nccn4c2)OCC3)c1] | 7-(Imidazo[1,2-a]pyridin-6-yl)-6-(3-methoxyphenyl)-2,3-dihydropyrazolo[5,1-b]oxazole |

-continued
| No. | Structure | Name |
|---|---|---|
| 74 | 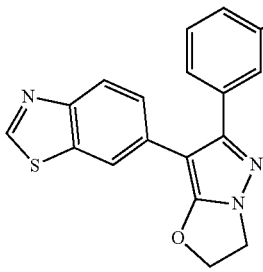 | 7-(Benzo[d]thiazol-6-yl)-6-(3-methoxyphenyl)-2,3-dihydropyrazolo[5,1-b]oxazole |
| 75 | 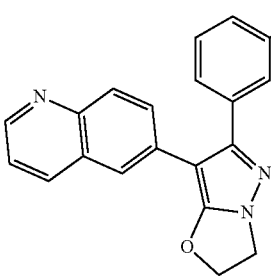 | 6-(3-Methoxyphenyl)-7-(quinolin-6-yl)-2,3-dihydropyrazolo[5,1-b]oxazole |
| 76 | 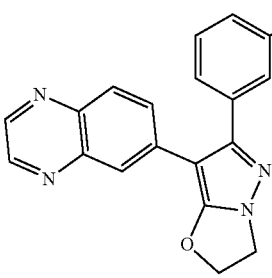 | 6-(3-Methoxyphenyl)-7-(quinoxalin-6-yl)-2,3-dihydropyrazolo[5,1-b]oxazole |
| 77 | 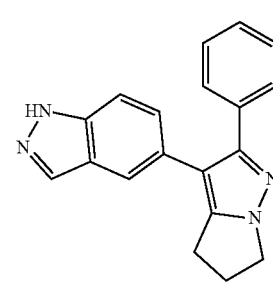 | 5-(2-(3-Fluorophenyl)-5,6-dihydro-4H-pyrrolo[1,2-b]pyrazol-3-yl)-1H-indazole |
| 78 | 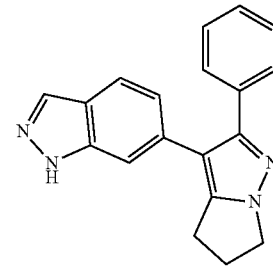 | 6-(2-(3-Fluorophenyl)-5,6-dihydro-4H-pyrrolo[1,2-b]pyrazol-3-yl)-1H-indazole |

-continued
| No. | Structure | Name |
|---|---|---|
| 79 | 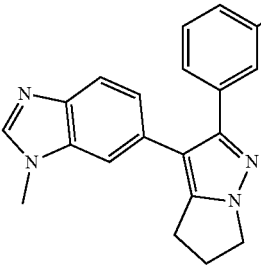 | 6-(2-(3-Fluorophenyl)-5,6-dihydro-4H-pyrrolo[1,2-b]pyrazol-3-yl)-1-methyl-1H-benzo[d]imidazole |
| 80 | 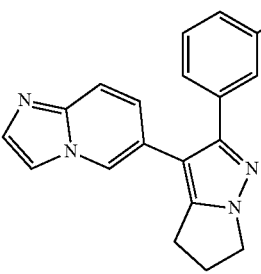 | 6-(2-(3-Fluorophenyl)-5,6-dihydro-4H-pyrrolo[1,2-b]pyrazol-3-yl)imidazo[1,2-a]pyridine |
| 81 | 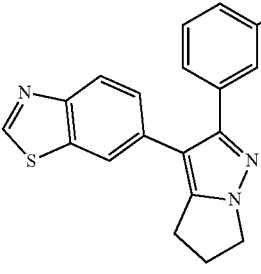 | 6-(2-(3-Fluorophenyl)-5,6-dihydro-4H-pyrrolo[1,2-b]pyrazol-3-yl)benzo[d]thiazole |
| 82 | 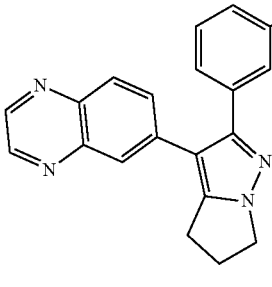 | 6-(2-(3-Fluorophenyl)-5,6-dihydro-4H-pyrrolo[1,2-b]pyrazol-3-yl)quinoxaline |
| 83 | 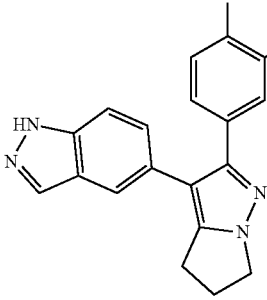 | 5-(2-(3,4-Difluorophenyl)-5,6-dihydro-4H-pyrrolo[1,2-b]pyrazol-3-yl)-1H-indazole |

| No. | Structure | Name |
|---|---|---|
| 84 | 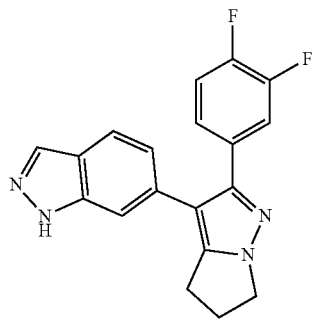 [SMILES: Fc1ccc(-c2nn3c(c2-c2ccc4cn[nH]c4c2)CCC3)cc1F] | 6-(2-(3,4-Difluorophenyl)-5,6-dihydro-4H-pyrrolo[1,2-b]pyrazol-3-yl)-1H-indazole |
| 85 | 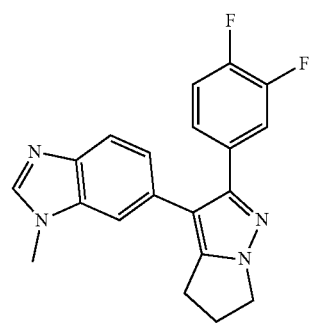 [SMILES: Cn1cnc2ccc(-c3c(-c4ccc(F)c(F)c4)nn4c3CCC4)cc21] | 6-(2-(3,4-Difluorophenyl)-5,6-dihydro-4H-pyrrolo[1,2-b]pyrazol-3-yl)-1-methyl-1H-benzo[d]imidazole |
| 86 | 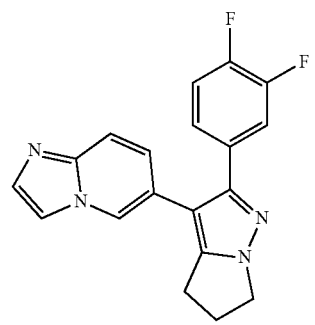 [SMILES: Fc1ccc(-c2nn3c(c2-c2ccc4nccn4c2)CCC3)cc1F] | 6-(2-(3,4-Difluorophenyl)-5,6-dihydro-4H-pyrrolo[1,2-b]pyrazol-3-yl)imidazo[1,2-a]pyridine |
| 87 | 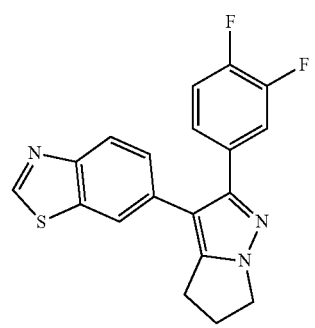 [SMILES: Fc1ccc(-c2nn3c(c2-c2ccc4ncsc4c2)CCC3)cc1F] | 6-(2-(3,4-Difluorophenyl)-5,6-dihydro-4H-pyrrolo[1,2-b]pyrazol-3-yl)benzo[d]thiazole |

-continued

| No. | Structure | Name |
|---|---|---|
| 88 | 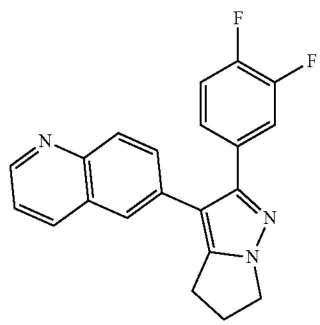 [SMILES: Fc1ccc(-c2nn3c(c2-c2ccc4ncccc4c2)CCC3)cc1F] | 6-(2-(3,4-Difluorophenyl)-5,6-dihydro-4H-pyrrolo[1,2-b]pyrazol-3-yl)quinoline |
| 89 | 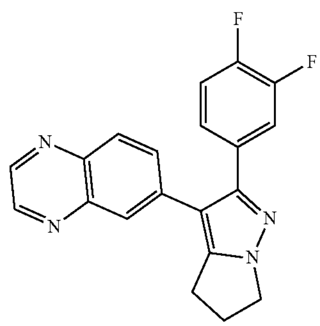 [SMILES: Fc1ccc(-c2nn3c(c2-c2ccc4nccnc4c2)CCC3)cc1F] | 6-(2-(3,4-Difluorophenyl)-5,6-dihydro-4H-pyrrolo[1,2-b]pyrazol-3-yl)quinoxaline |
| 90 | 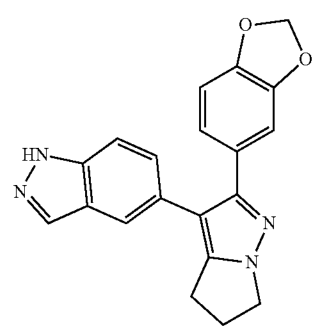 [SMILES: c1cc2c(cc1-c1nn3c(c1-c1ccc4[nH]ncc4c1)CCC3)OCO2] | 5-(2-(Benzo[d][1,3]dioxol-5-yl)-5,6-dihydro-4H-pyrrolo[1,2-b]pyrazol-3-yl)-1H-indazole |
| 91 | 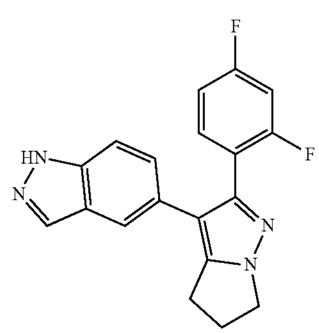 [SMILES: Fc1ccc(-c2nn3c(c2-c2ccc4[nH]ncc4c2)CCC3)c(F)c1] | 5-(2-(2,4-Difluorophenyl)-5,6-dihydro-4H-pyrrolo[1,2-b]pyrazol-3-yl)-1H-indazole |

-continued
| No. | Structure | Name |
|---|---|---|
| 92 | 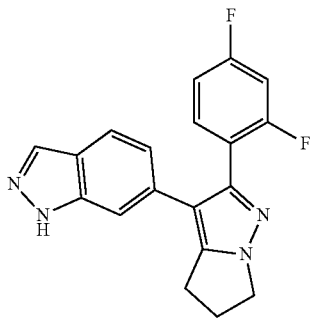 [SMILES: Fc1ccc(-c2nn3c(c2-c2ccc4cn[nH]c4c2)CCC3)c(F)c1] | 6-(2-(2,4-Difluorophenyl)-5,6-dihydro-4H-pyrrolo[1,2-b]pyrazol-3-yl)-1-methyl-1H-benzo[d]imidazole |
| 93 | 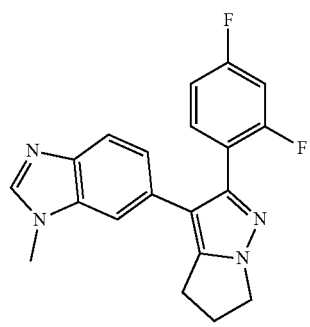 [SMILES: Cn1cnc2ccc(-c3c(-c4ccc(F)cc4F)nn4c3CCC4)cc21] | 6-(2-(2,4-Difluorophenyl)-5,6-dihydro-4H-pyrrolo[1,2-b]pyrazol-3-yl)-1-methyl-1H-benzo[d]imidazole |
| 94 | 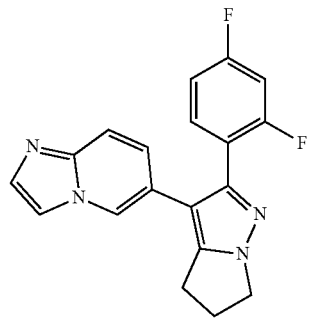 [SMILES: Fc1ccc(-c2nn3c(c2-c2ccc4nccn4c2)CCC3)c(F)c1] | 6-(2-(2,4-Difluorophenyl)-5,6-dihydro-4H-pyrrolo[1,2-b]pyrazol-3-yl)imidazo[1,2-a]pyridine |
| 95 | 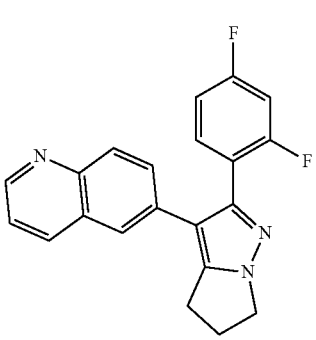 | 6-(2-(2,4-Difluorophenyl)-5,6-dihydro-4H-pyrrolo[1,2-b]pyrazol-3-yl)quinoline |

-continued

| No. | Structure | Name |
|---|---|---|
| 96 | 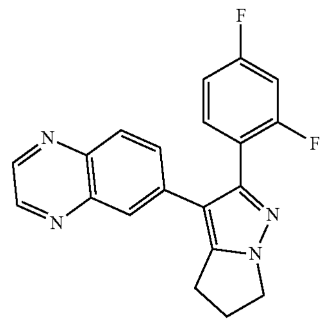 [SMILES: Fc1ccc(-c2nn3c(c2-c2ccc4ncccc4c2)CCC3)c(F)c1] | 6-(2-(2,4-Difluorophenyl)-5,6-dihydro-4H-pyrrolo[1,2-b]pyrazol-3-yl)quinoxaline |
| 97 | 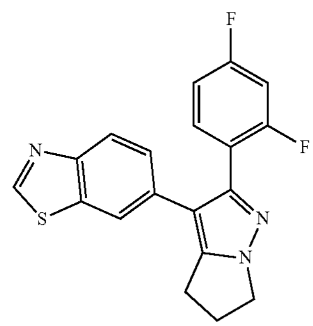 [SMILES: Fc1ccc(-c2nn3c(c2-c2ccc4ncsc4c2)CCC3)c(F)c1] | 6-(2-(2,4-Difluorophenyl)-5,6-dihydro-4H-pyrrolo[1,2-b]pyrazol-3-yl)benzo[d]thiazole |
| 98 | 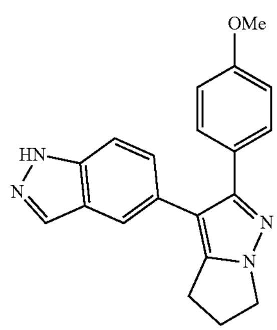 [SMILES: COc1ccc(-c2nn3c(c2-c2ccc4[nH]ncc4c2)CCC3)cc1] | 5-(2-(4-Methoxyphenyl)-5,6-dihydro-4H-pyrrolo[1,2-b]pyrazol-3-yl)-1H-indazole |
| 99 | 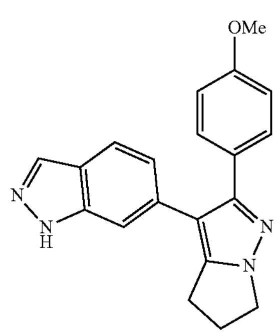 [SMILES: COc1ccc(-c2nn3c(c2-c2ccc4cn[nH]c4c2)CCC3)cc1] | 6-(2-(4-Methoxyphenyl)-5,6-dihydro-4H-pyrrolo[1,2-b]pyrazol-3-yl)-1H-indazole |

-continued
| No. | Structure | Name |
|---|---|---|
| 100 | 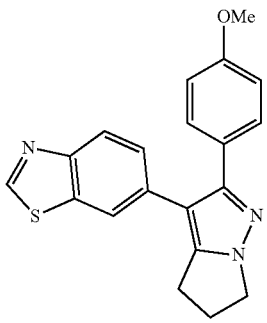 [SMILES: COc1ccc(-c2nn3c(c2-c2ccc4ncsc4c2)CCC3)cc1] | 6-(2-(4-Methoxyphenyl)-5,6-dihydro-4H-pyrrolo[1,2-b]pyrazol-3-yl)benzo[d]thiazole |
| 101 | 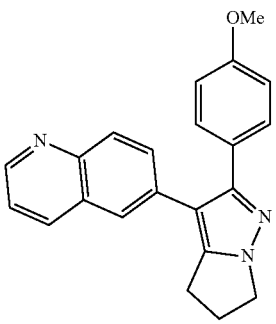 [SMILES: COc1ccc(-c2nn3c(c2-c2ccc4ncccc4c2)CCC3)cc1] | 6-(2-(4-Methoxyphenyl)-5,6-dihydro-4H-pyrrolo[1,2-b]pyrazol-3-yl)quinoline |
| 102 | 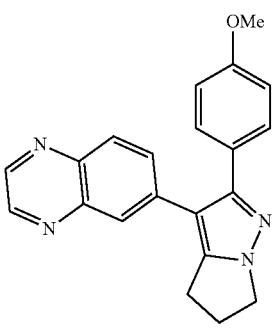 [SMILES: COc1ccc(-c2nn3c(c2-c2ccc4nccnc4c2)CCC3)cc1] | 6-(2-(4-Methoxyphenyl)-5,6-dihydro-4H-pyrrolo[1,2-b]pyrazol-3-yl)quinoxaline |
| 103 | 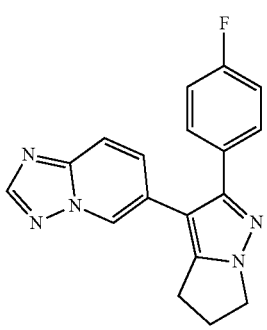 [SMILES: Fc1ccc(-c2nn3c(c2-c2ccc4ncnn4c2)CCC3)cc1] | 6-(2-(4-Fluorophenyl)-5,6-dihydro-4H-pyrrolo[1,2-b]pyrazol-3-yl)-[1,2,4]triazolo[1,5-a]pyridine |
| 104 | 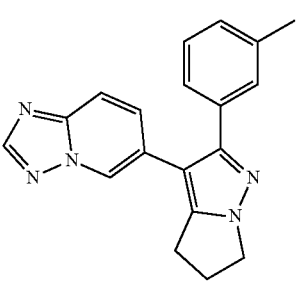 [SMILES: Cc1cccc(-c2nn3c(c2-c2ccc4ncnn4c2)CCC3)c1] | 6-(2-(m-Tolyl)-5,6-dihydro-4H-pyrrolo[1,2-b]pyrazol-3-yl)-[1,2,4]triazolo[1,5-a]pyridine |

-continued

| No. | Structure | Name |
|---|---|---|
| 105 | 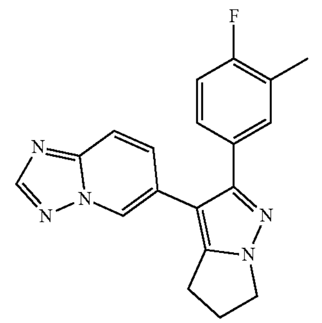 [SMILES: Cc1cc(-c2nn3c(c2-c2ccc4ncnn4c2)CCC3)ccc1F] | 6-(2-(4-Fluoro-3-methylphenyl)-5,6-dihydro-4H-pyrrolo[1,2-b]pyrazol-3-yl)-[1,2,4]triazolo[1,5-a]pyridine |
| 106 | 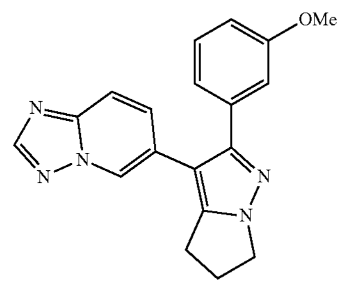 [SMILES: COc1cccc(-c2nn3c(c2-c2ccc4ncnn4c2)CCC3)c1] | 6-(2-(3-Methoxyphenyl)-5,6-dihydro-4H-pyrrolo[1,2-b]pyrazol-3-yl)-[1,2,4]triazolo[1,5-a]pyridine |
| 107 | 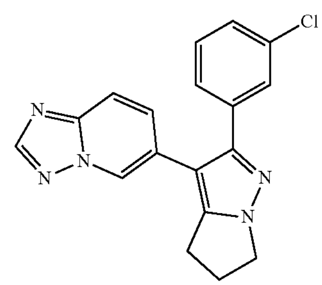 [SMILES: Clc1cccc(-c2nn3c(c2-c2ccc4ncnn4c2)CCC3)c1] | 6-(2-(3-Chlorophenyl)-5,6-dihydro-4H-pyrrolo[1,2-b]pyrazol-3-yl)-[1,2,4]triazolo[1,5-a]pyridine |
| 108 | 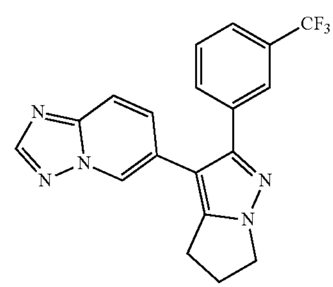 [SMILES: FC(F)(F)c1cccc(-c2nn3c(c2-c2ccc4ncnn4c2)CCC3)c1] | 6-(2-(3-Trifluoromethylphenyl)-5,6-dihydro-4H-pyrrolo[1,2-b]pyrazol-3-yl)-[1,2,4]triazolo[1,5-a]pyridine |
| 109 | 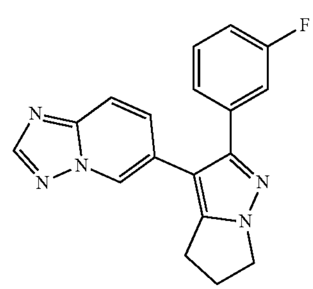 [SMILES: Fc1cccc(-c2nn3c(c2-c2ccc4ncnn4c2)CCC3)c1] | 6-(2-(3-Fluorophenyl)-5,6-dihydro-4H-pyrrolo[1,2-b]pyrazol-3-yl)-[1,2,4]triazolo[1,5-a]pyridine |

-continued

| No. | Structure | Name |
|---|---|---|
| 110 | 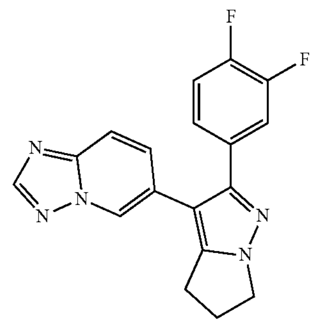 [SMILES: Fc1ccc(-c2nn3c(c2-c2ccc4ncnn4c2)CCC3)cc1F] | 6-(2-(3,4-Difluorophenyl)-5,6-dihydro-4H-pyrrolo[1,2-b]pyrazol-3-yl)-[1,2,4]triazolo[1,5-a]pyridine |
| 111 | 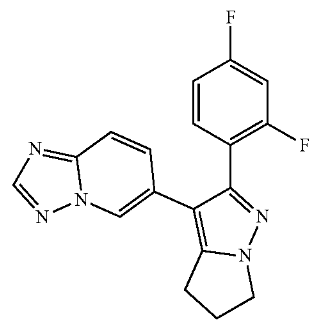 [SMILES: Fc1ccc(-c2nn3c(c2-c2ccc4ncnn4c2)CCC3)c(F)c1] | 6-(2-(2,4-Difluorophenyl)-5,6-dihydro-4H-pyrrolo[1,2-b]pyrazol-3-yl)-[1,2,4]triazolo[1,5-a]pyridine |
| 112 | 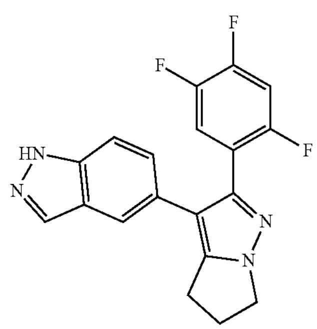 | 5-(2-(2,4,5-Trifluorophenyl)-5,6-dihydro-4H-pyrrolo[1,2-b]pyrazol-3-yl)-1H-indazole |
| 113 | 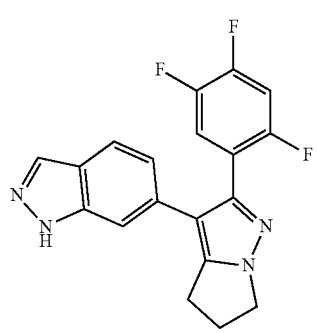 [SMILES: Fc1cc(F)c(-c2nn3c(c2-c2ccc4cn[nH]c4c2)CCC3)cc1F] | 6-(2-(2,4,5-Trifluorophenyl)-5,6-dihydro-4H-pyrrolo[1,2-b]pyrazol-3-yl)-1H-indazole |

-continued

| No. | Structure | Name |
|---|---|---|
| 114 | 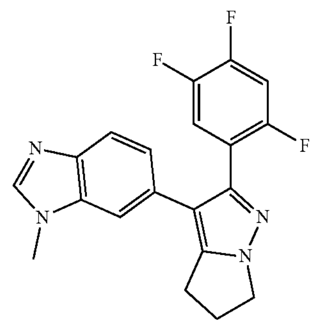 [SMILES: Cn1cnc2ccc(-c3c(-c4cc(F)c(F)cc4F)nn4c3CCC4)cc21] | 1-Methyl-6-(2-(2,4,5-trifluorophenyl)-5,6-dihydro-4H-pyrrolo[1,2-b]pyrazol-3-yl)-1H-benzo[d]imidazole |
| 115 | 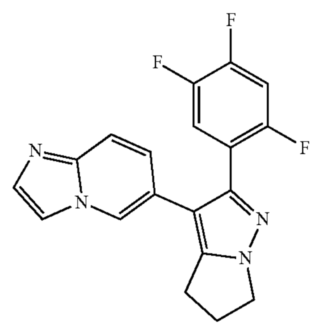 | 6-(2-(2,4,5-Trifluorophenyl)-5,6-dihydro-4H-pyrrolo[1,2-b]pyrazol-3-yl)imidazo[1,2-a]pyridine |
| 116 | 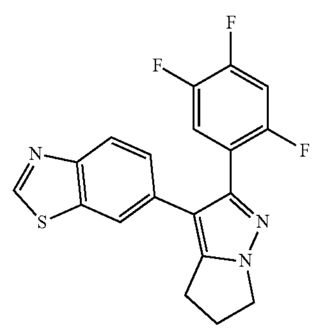 [SMILES: Fc1cc(F)c(-c2nn3c(c2-c2ccc4ncsc4c2)CCC3)cc1F] | 6-(2-(2,4,5-Trifluorophenyl)-5,6-dihydro-4H-pyrrolo[1,2-b]pyrazol-3-yl)benzo[d]thiazole |
| 117 | 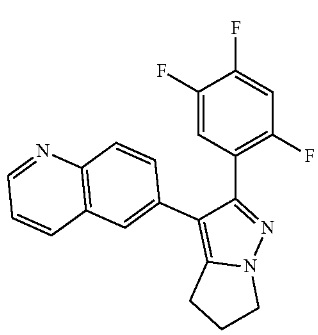 | 6-(2-(2,4,5-Trifluorophenyl)-5,6-dihydro-4H-pyrrolo[1,2-b]pyrazol-3-yl)quinoline |

-continued

| No. | Structure | Name |
|---|---|---|
| 118 | 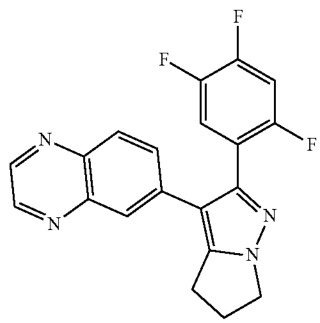 [SMILES: Fc1cc(F)c(-c2nn3c(c2-c2ccc4nccnc4c2)CCC3)cc1F] | 6-(2-(2,4,5-Trifluorophenyl)-5,6-dihydro-4H-pyrrolo[1,2-b]pyrazol-3-yl)quinoxaline |
| 119 | 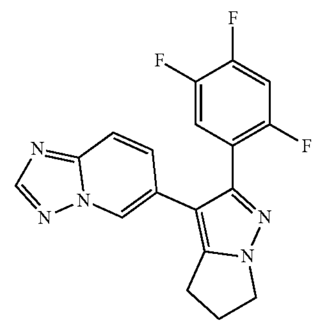 [SMILES: Fc1cc(F)c(-c2nn3c(c2-c2ccc4ncnn4c2)CCC3)cc1F] | 6-(2-(2,4,5-Trifluorophenyl)-5,6-dihydro-4H-pyrrolo[1,2-b]pyrazol-3-yl)-[1,2,4]triazolo[1,5-a]pyridine |
| 120 | 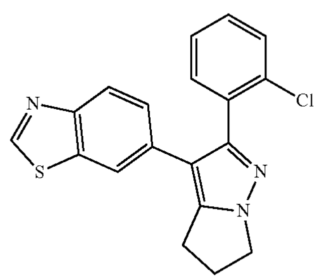 [SMILES: Clc1ccccc1-c1nn2c(c1-c1ccc3ncsc3c1)CCC2] | 6-(2-(2-Chlorophenyl)-5,6-dihydro-4H-pyrrolo[1,2-b]pyrazol-3-yl)benzo[d]thiazole |
| 121 | 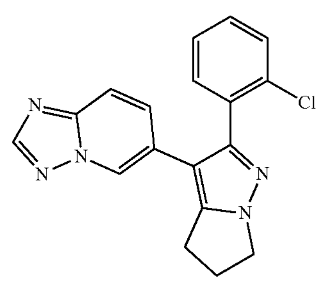 [SMILES: Clc1ccccc1-c1nn2c(c1-c1ccc3ncnn3c1)CCC2] | 6-(2-(2-Chlorophenyl)-5,6-dihydro-4H-pyrrolo[1,2-b]pyrazol-3-yl)-[1,2,4]triazolo[1,5-a]pyridine |
| 122 | 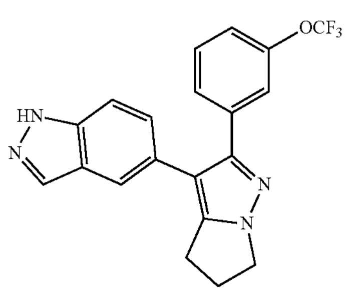 [SMILES: FC(F)(F)Oc1cccc(-c2nn3c(c2-c2ccc4[nH]ncc4c2)CCC3)c1] | 5-(2-(3-Trifluoromethoxyphenyl)-5,6-dihydro-4H-pyrrolo[1,2-b]pyrazol-3-yl)-1H-indazole |

-continued

| No. | Structure | Name |
|---|---|---|
| 123 | 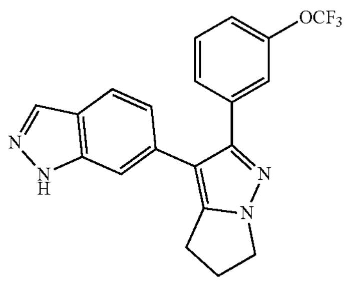 [SMILES: FC(F)(F)Oc1cccc(-c2nn3c(c2-c2ccc4cn[nH]c4c2)CCC3)c1] | 6-(2-(3-Trifluoromethoxyphenyl)-5,6-dihydro-4H-pyrrolo[1,2-b]pyrazol-3-yl)-1H-indazole |
| 124 | 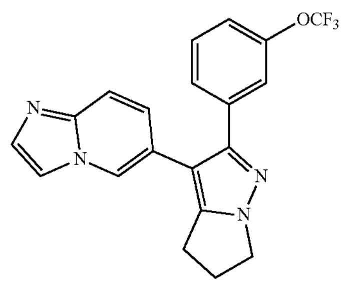 [SMILES: FC(F)(F)Oc1cccc(-c2nn3c(c2-c2ccc4nccn4c2)CCC3)c1] | 6-(2-(3-Trifluoromethoxyphenyl)-5,6-dihydro-4H-pyrrolo[1,2-b]pyrazol-3-yl)imidazo[1,2-a]pyridine |
| 125 | 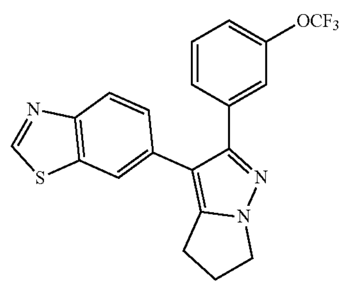 [SMILES: FC(F)(F)Oc1cccc(-c2nn3c(c2-c2ccc4ncsc4c2)CCC3)c1] | 6-(2-(3-Trifluoromethoxyphenyl)-5,6-dihydro-4H-pyrrolo[1,2-b]pyrazol-3-yl)benzo[d]thiazole |
| 126 | 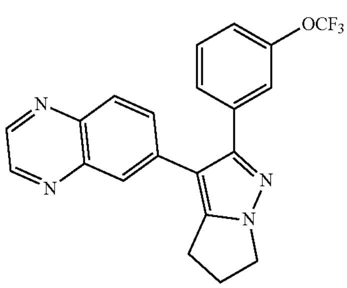 [SMILES: FC(F)(F)Oc1cccc(-c2nn3c(c2-c2ccc4nccnc4c2)CCC3)c1] | 6-(2-(3-Trifluoromethoxyphenyl)-5,6-dihydro-4H-pyrrolo[1,2-b]pyrazol-3-yl)quinoxaline |
| 127 | 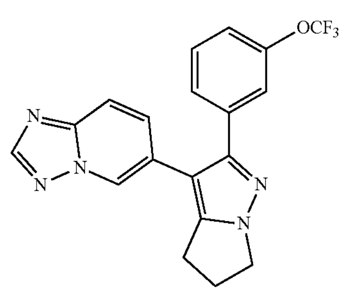 [SMILES: FC(F)(F)Oc1cccc(-c2nn3c(c2-c2ccc4ncnn4c2)CCC3)c1] | 6-(2-(3-Trifluoromethoxyphenyl)-5,6-dihydro-4H-pyrrolo[1,2-b]pyrazol-3-yl)-[1,2,4]triazolo[1,5-a]pyridine |

-continued

| No. | Structure | Name |
|---|---|---|
| 128 | 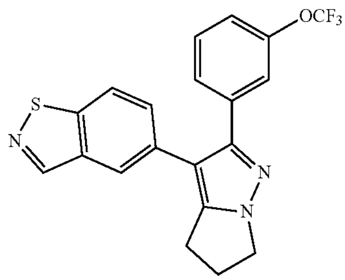 [SMILES: FC(F)(F)Oc1cccc(-c2nn3c(c2-c2ccc4sncc4c2)CCC3)c1] | 5-(2-(3-Trifluoromethoxyphenyl)-5,6-dihydro-4H-pyrrolo[1,2-b]pyrazol-3-yl)benzo[d]isothiazole |
| 129 | 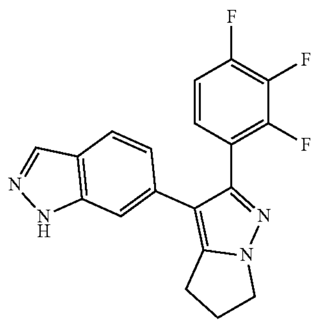 [SMILES: Fc1ccc(-c2nn3c(c2-c2ccc4cn[nH]c4c2)CCC3)c(F)c1F] | 6-(2-(2,3,4-Trifluorophenyl)-5,6-dihydro-4H-pyrrolo[1,2-b]pyrazol-3-yl)-1H-indazole |
| 130 | 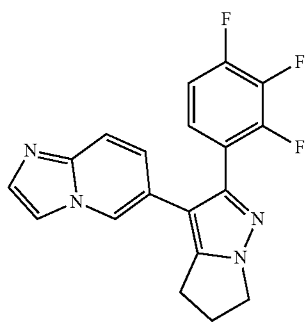 [SMILES: Fc1ccc(-c2nn3c(c2-c2ccc4nccn4c2)CCC3)c(F)c1F] | 6-(2-(2,3,4-Trifluorophenyl)-5,6-dihydro-4H-pyrrolo[1,2-b]pyrazol-3-yl)imidazo[1,2-a]pyridine |
| 131 | 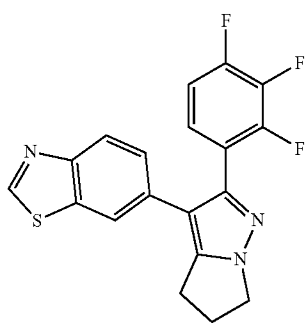 [SMILES: Fc1ccc(-c2nn3c(c2-c2ccc4ncsc4c2)CCC3)c(F)c1F] | 6-(2-(2,3,4-Trifluorophenyl)-5,6-dihydro-4H-pyrrolo[1,2-b]pyrazol-3-yl)benzo[d]thiazole |
| 132 | 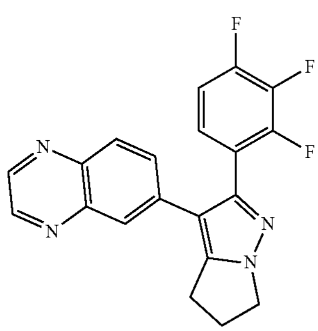 | 6-(2-(2,3,4-Trifluorophenyl)-5,6-dihydro-4H-pyrrolo[1,2-b]pyrazol-3-yl)quinoxaline |

-continued

| No. | Structure | Name |
|---|---|---|
| 133 | 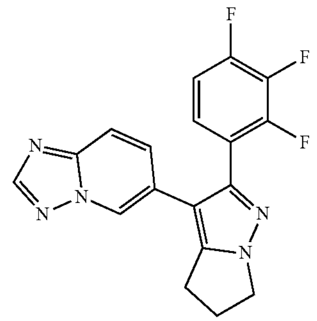 | 6-(2-(2,3,4-Trifluorophenyl)-5,6-dihydro-4H-pyrrolo[1,2-b]pyrazol-3-yl)-[1,2,4]triazolo[1,5-a]pyridine |
| 134 | 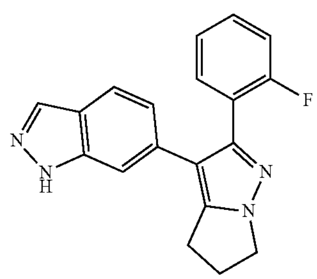 [SMILES: Fc1ccccc1-c1nn2c(c1-c1ccc3cn[nH]c3c1)CCC2] | 6-(2-(2-Fluorophenyl)-5,6-dihydro-4H-pyrrolo[1,2-b]pyrazol-3-yl)-1H-indazole |
| 135 | 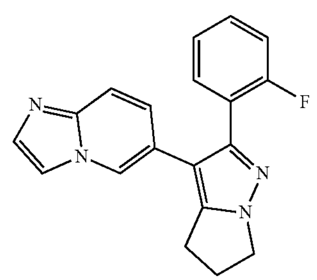 [SMILES: Fc1ccccc1-c1nn2c(c1-c1ccc3nccn3c1)CCC2] | 6-(2-(2-Fluorophenyl)-5,6-dihydro-4H-pyrrolo[1,2-b]pyrazol-3-yl)imidazo[1,2-a]pyridine |
| 136 | 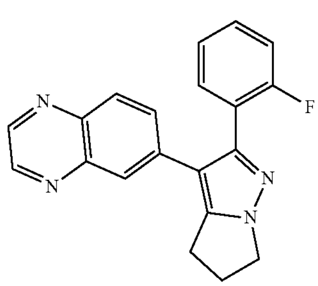 [SMILES: Fc1ccccc1-c1nn2c(c1-c1ccc3nccnc3c1)CCC2] | 6-(2-(2-Fluorophenyl)-5,6-dihydro-4H-pyrrolo[1,2-b]pyrazol-3-yl)quinoxaline |
| 137 | 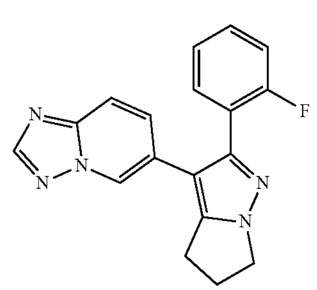 [SMILES: Fc1ccccc1-c1nn2c(c1-c1ccc3ncnn3c1)CCC2] | 6-(2-(2-Fluorophenyl)-5,6-dihydro-4H-pyrrolo[1,2-b]pyrazol-3-yl)-[1,2,4]triazolo[1,5-a]pyridine |

| No. | Structure | Name |
|---|---|---|
| 138 | 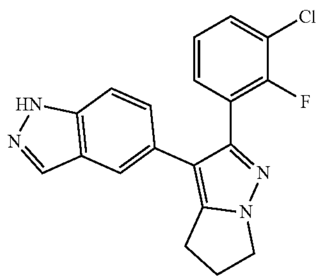 [SMILES: Fc1c(Cl)cccc1-c1nn2c(c1-c1ccc3[nH]ncc3c1)CCC2] | 5-(2-(3-Chloro-2-fluorophenyl)-5,6-dihydro-4H-pyrrolo[1,2-b]pyrazol-3-yl)-1H-indazole |
| 139 | 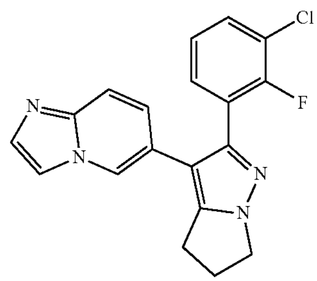 [SMILES: Fc1c(Cl)cccc1-c1nn2c(c1-c1ccc3nccn3c1)CCC2] | 6-(2-(3-Chloro-2-fluorophenyl)-5,6-dihydro-4H-pyrrolo[1,2-b]pyrazol-3-yl)imidazo[1,2-a]pyridine |
| 140 | 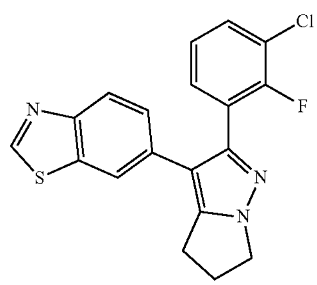 [SMILES: Fc1c(Cl)cccc1-c1nn2c(c1-c1ccc3ncsc3c1)CCC2] | 6-(2-(3-Chloro-2-fluorophenyl)-5,6-dihydro-4H-pyrrolo[1,2-b]pyrazol-3-yl)benzo[d]thiazole |
| 141 | 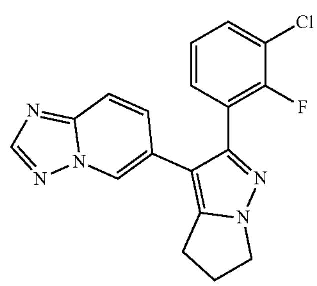 [SMILES: Fc1c(Cl)cccc1-c1nn2c(c1-c1ccc3ncnn3c1)CCC2] | 6-(2-(3-Chloro-2-fluorophenyl)-5,6-dihydro-4H-pyrrolo[1,2-b]pyrazol-3-yl)-[1,2,4]triazolo[1,5-a]pyridine |
| 142 | 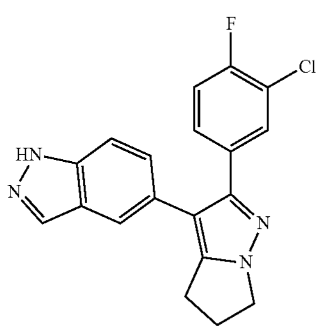 [SMILES: Fc1ccc(-c2nn3c(c2-c2ccc4[nH]ncc4c2)CCC3)cc1Cl] | 5-(2-(3-Chloro-4-fluorophenyl)-5,6-dihydro-4H-pyrrolo[1,2-b]pyrazol-3-yl)-1H-indazole |

-continued

| No. | Structure | Name |
|---|---|---|
| 143 | 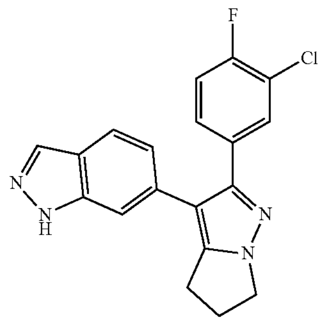 [SMILES: Fc1ccc(-c2nn3c(c2-c2ccc4cn[nH]c4c2)CCC3)cc1Cl] | 6-(2-(3-Chloro-4-fluorophenyl)-5,6-dihydro-4H-pyrrolo[1,2-b]pyrazol-3-yl)-1H-indazole |
| 144 | 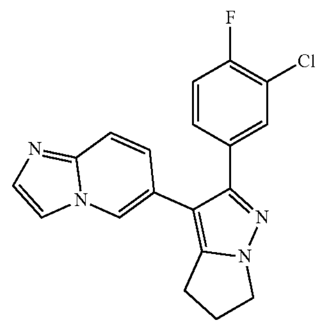 [SMILES: Fc1ccc(-c2nn3c(c2-c2ccc4nccn4c2)CCC3)cc1Cl] | 6-(2-(3-Chloro-4-fluorophenyl)-5,6-dihydro-4H-pyrrolo[1,2-b]pyrazol-3-yl)imidazo[1,2-a]pyridine |
| 145 | 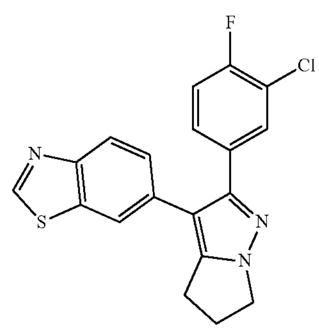 [SMILES: Fc1ccc(-c2nn3c(c2-c2ccc4ncsc4c2)CCC3)cc1Cl] | 6-(2-(3-Chloro-4-fluorophenyl)-5,6-dihydro-4H-pyrrolo[1,2-b]pyrazol-3-yl)benzo[d]thiazole |
| 146 | 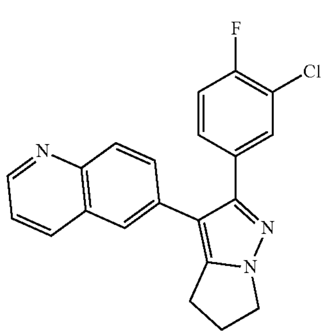 [SMILES: Fc1ccc(-c2nn3c(c2-c2ccc4ncccc4c2)CCC3)cc1Cl] | 6-(2-(3-Chloro-4-fluorophenyl)-5,6-dihydro-4H-pyrrolo[1,2-b]pyrazol-3-yl)quinoline |

-continued

| No. | Structure | Name |
|---|---|---|
| 147 | 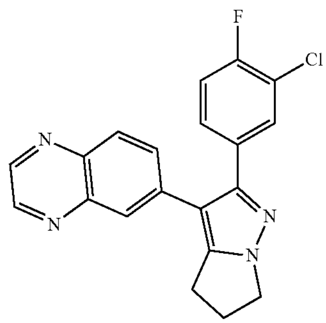 [SMILES: Fc1ccc(-c2nn3c(c2-c2ccc4nccnc4c2)CCC3)cc1Cl] | 6-(2-(3-Chloro-4-fluorophenyl)-5,6-dihydro-4H-pyrrolo[1,2-b]pyrazol-3-yl)quinoxaline |
| 148 | 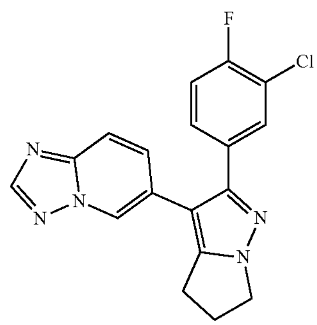 [SMILES: Fc1ccc(-c2nn3c(c2-c2ccc4ncnn4c2)CCC3)cc1Cl] | 6-(2-(3-Chloro-4-fluorophenyl)-5,6-dihydro-4H-pyrrolo[1,2-b]pyrazol-3-yl)-[1,2,4]triazolo[1,5-a]pyridine |
| 149 | 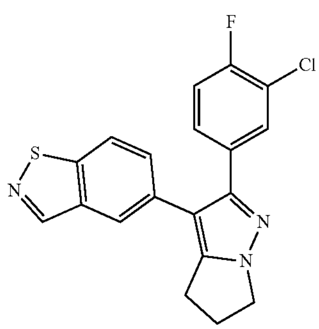 [SMILES: Fc1ccc(-c2nn3c(c2-c2ccc4sncc4c2)CCC3)cc1Cl] | 5-(2-(3-Chloro-4-fluorophenyl)-5,6-dihydro-4H-pyrrolo[1,2-b]pyrazol-3-yl)benzo[d]isothiazole |
| 150 | 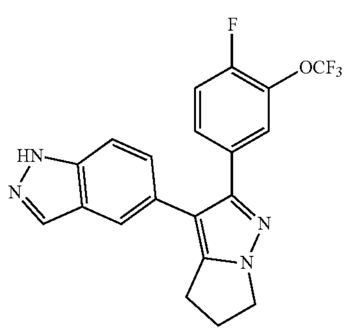 [SMILES: Fc1ccc(-c2nn3c(c2-c2ccc4[nH]ncc4c2)CCC3)cc1OC(F)(F)F] | 5-(2-(4-Fluoro-3-trifluoromethoxyphenyl)-5,6-dihydro-4H-pyrrolo[1,2-b]pyrazol-3-yl)-1H-indazole |

-continued

| No. | Structure | Name |
|---|---|---|
| 151 | 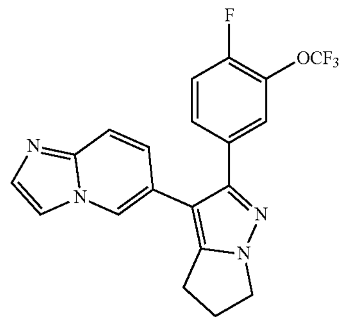 [SMILES: Fc1ccc(-c2nn3c(c2-c2ccc4nccn4c2)CCC3)cc1OC(F)(F)F] | 6-(2-(4-Fluoro-3-trifluoromethoxyphenyl)-5,6-dihydro-4H-pyrrolo[1,2-b]pyrazol-3-yl)imidazo[1,2-a]pyridine |
| 152 | 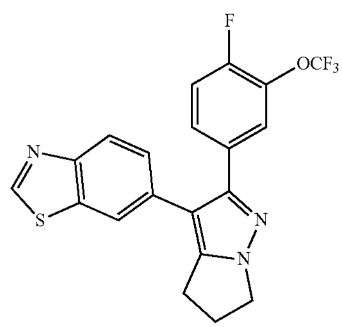 [SMILES: Fc1ccc(-c2nn3c(c2-c2ccc4ncsc4c2)CCC3)cc1OC(F)(F)F] | 6-(2-(4-Fluoro-3-trifluoromethoxyphenyl)-5,6-dihydro-4H-pyrrolo[1,2-b]pyrazol-3-yl)benzo[d]thiazole |
| 153 | 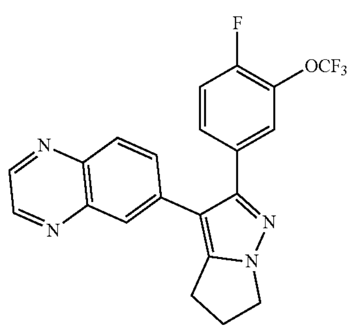 [SMILES: Fc1ccc(-c2nn3c(c2-c2ccc4nccnc4c2)CCC3)cc1OC(F)(F)F] | 6-(2-(4-Fluoro-3-trifluoromethoxyphenyl)-5,6-dihydro-4H-pyrrolo[1,2-b]pyrazol-3-yl)quinoxaline |
| 154 | 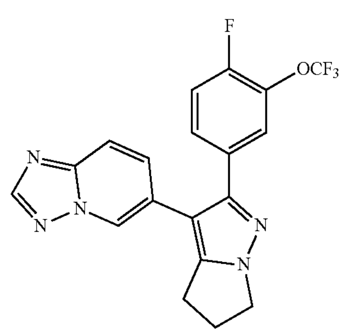 [SMILES: Fc1ccc(-c2nn3c(c2-c2ccc4ncnn4c2)CCC3)cc1OC(F)(F)F] | 6-(2-(4-Fluoro-3-trifluoromethoxyphenyl)-5,6-dihydro-4H-pyrrolo[1,2-b]pyrazol-3-yl)-[1,2,4]triazolo[1,5-a]pyridine |

-continued

| No. | Structure | Name |
|---|---|---|
| 155 | 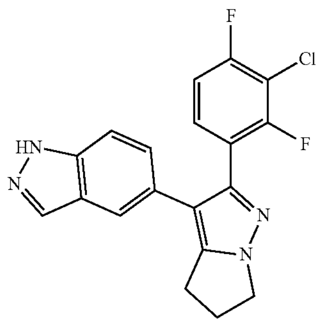 [SMILES: Fc1ccc(-c2nn3c(c2-c2ccc4[nH]ncc4c2)CCC3)c(F)c1Cl] | 5-(2-(3-Chloro-2,4-difluorophenyl)-5,6-dihydro-4H-pyrrolo[1,2-b]pyrazol-3-yl)-1H-indazole |
| 156 | 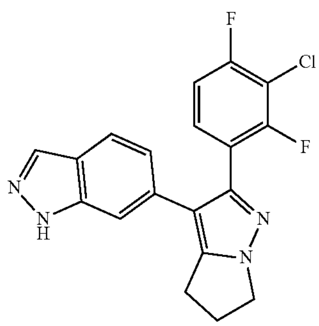 [SMILES: Fc1ccc(-c2nn3c(c2-c2ccc4cn[nH]c4c2)CCC3)c(F)c1Cl] | 6-(2-(3-Chloro-2,4-difluorophenyl)-5,6-dihydro-4H-pyrrolo[1,2-b]pyrrazol-3-yl)-1H-indazole |
| 157 | 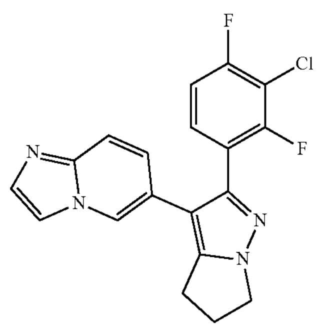 [SMILES: Fc1ccc(-c2nn3c(c2-c2ccc4nccn4c2)CCC3)c(F)c1Cl] | 6-(2-(3-Chloro-2,4-difluorophenyl)-5,6-dihydro-4H-pyrrolo[1,2-b]pyrazol-3-yl)imidazo[1,2-a]pyridine |
| 158 | 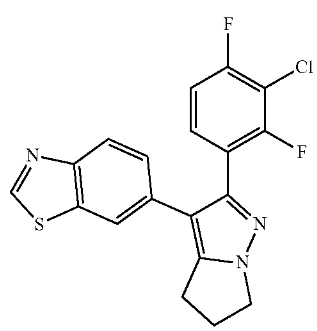 [SMILES: Fc1ccc(-c2nn3c(c2-c2ccc4ncsc4c2)CCC3)c(F)c1Cl] | 6-(2-(3-Chloro-2,4-difluorophenyl)-5,6-dihydro-4H-pyrrolo[1,2-b]pyrazol-3-yl)benzo[d]thiazole |

-continued

| No. | Structure | Name |
|---|---|---|
| 159 | 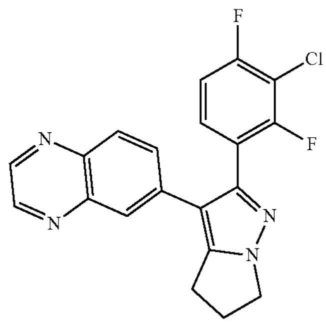 [SMILES: Fc1ccc(-c2nn3c(c2-c2ccc4nccnc4c2)CCC3)c(F)c1Cl] | 6-(2-(3-Chloro-2,4-difluorophenyl)-5,6-dihydro-4H-pyrrolo[1,2-b]pyrazol-3-yl)quinoxaline |
| 160 | 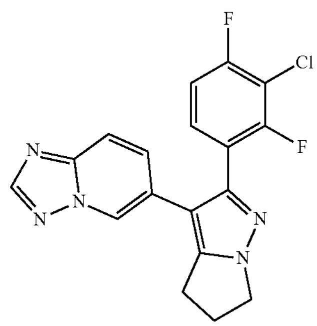 [SMILES: Fc1ccc(-c2nn3c(c2-c2ccc4ncnn4c2)CCC3)c(F)c1Cl] | 6-(2-(3-Chloro-2,4-difluorophenyl)-5,6-dihydro-4H-pyrrolo[1,2-b]pyrazol-3-yl)-[1,2,4]triazolo[1,5-a]pyridine |
| 161 | 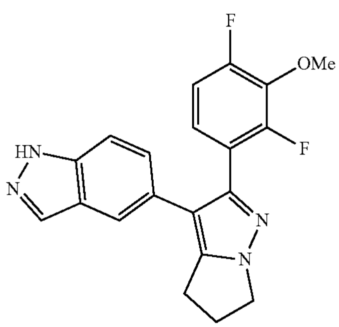 [SMILES: COc1c(F)ccc(-c2nn3c(c2-c2ccc4[nH]ncc4c2)CCC3)c1F] | 5-(2-(2,4-Difluoro-3-methoxyphenyl)-5,6-dihydro-4H-pyrrolo[1,2-b]pyrazol-3-yl)-1H-indazole |
| 162 | 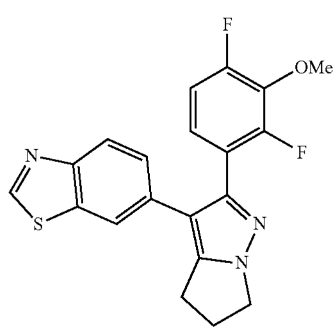 [SMILES: COc1c(F)ccc(-c2nn3c(c2-c2ccc4ncsc4c2)CCC3)c1F] | 6-(2-(2,4-Difluoro-3-methoxyphenyl)-5,6-dihydro-4H-pyrrolo[1,2-b]pyrazol-3-yl)benzo[d]thiazole |

| No. | Structure | Name |
|---|---|---|
| 163 | 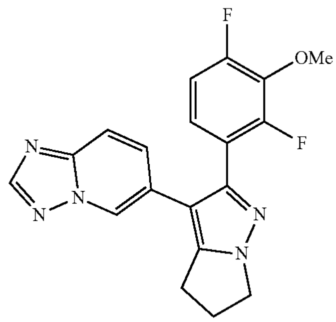 [SMILES: COc1c(F)ccc(-c2nn3c(c2-c2ccc4ncnn4c2)CCC3)c1F] | 6-(2-(2,4-Difluoro-3-methoxyphenyl)-5,6-dihydro-4H-pyrrolo[1,2-b]pyrazol-3-yl)-[1,2,4]triazolo[1,5-a]pyridine |
| 164 | 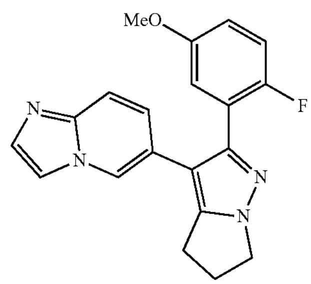 [SMILES: COc1ccc(F)c(-c2nn3c(c2-c2ccc4nccn4c2)CCC3)c1] | 6-(2-(2-Fluoro-5-methoxyphenyl)-5,6-dihydro-4H-pyrrolo[1,2-b]pyrazol-3-yl)imidazo[1,2-a]pyridine |
| 165 | 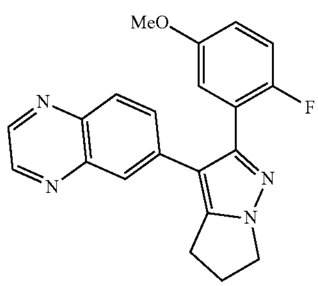 [SMILES: COc1ccc(F)c(-c2nn3c(c2-c2ccc4nccnc4c2)CCC3)c1] | 6-(2-(2-Fluoro-5-methoxyphenyl)-5,6-dihydro-4H-pyrrolo[1,2-b]pyrazol-3-yl)quinoxaline |
| 166 | 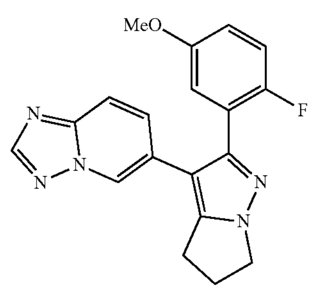 [SMILES: COc1ccc(F)c(-c2nn3c(c2-c2ccc4ncnn4c2)CCC3)c1] | 6-(2-(2-Fluoro-3-methoxyphenyl)-5,6-dihydro-4H-pyrrolo[1,2-b]pyrazol-3-yl)-[1,2,4]triazolo[1,5-a]pyridine |
| 167 | 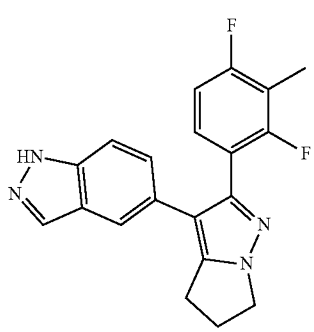 [SMILES: Cc1c(F)ccc(-c2nn3c(c2-c2ccc4[nH]ncc4c2)CCC3)c1F] | 5-(2-(2,4-Difluoro-3-methylphenyl)-5,6-dihydro-4H-pyrrolo[1,2-b]pyrazol-3-yl)-1H-indazole |

| No. | Structure | Name |
|---|---|---|
| 168 | 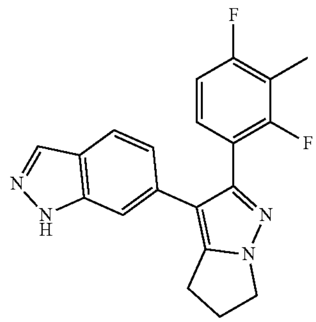 [SMILES: Cc1c(F)ccc(-c2nn3c(c2-c2ccc4cn[nH]c4c2)CCC3)c1F] | 6-(2-(2,4-Difluoro-3-methylphenyl)-5,6-dihydro-4H-pyrrolo[1,2-b]pyrazol-3-yl)-1H-indazole |
| 169 | 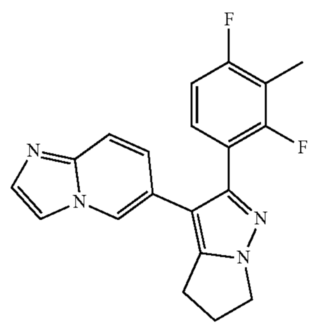 [SMILES: Cc1c(F)ccc(-c2nn3c(c2-c2ccc4nccn4c2)CCC3)c1F] | 6-(2-(2,4-Difluoro-3-methylphenyl)-5,6-dihydro-4H-pyrrolo[1,2-b]pyrazol-3-yl)imidazo[1,2-a]pyridine |
| 170 | 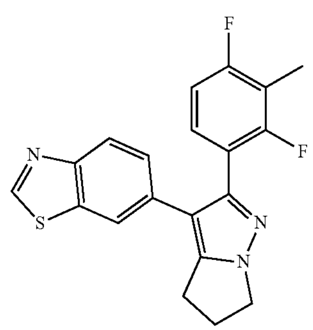 [SMILES: Cc1c(F)ccc(-c2nn3c(c2-c2ccc4ncsc4c2)CCC3)c1F] | 6-(2-(2,4-Difluoro-3-methylphenyl)-5,6-dihydro-4H-pyrrolo[1,2-b]pyrazol-3-yl)benzo[d]thiazole |
| 171 | 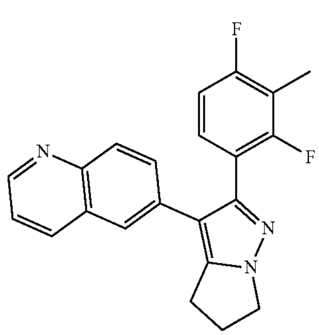 [SMILES: Cc1c(F)ccc(-c2nn3c(c2-c2ccc4ncccc4c2)CCC3)c1F] | 6-(2-(2,4-Difluoro-3-methylphenyl)-5,6-dihydro-4H-pyrrolo[1,2-b]pyrazol-3-yl)quinoline |

| No. | Structure | Name |
| --- | --- | --- |
| 172 | 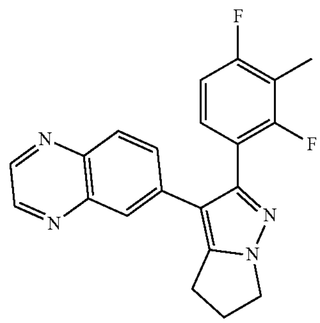 [SMILES: Cc1c(F)ccc(-c2nn3c(c2-c2ccc4nccnc4c2)CCC3)c1F] | 6-(2-(2,4-Difluoro-3-methylphenyl)-5,6-dihydro-4H-pyrrolo[1,2-b]pyrazol-3-yl)quinoxaline |
| 173 | 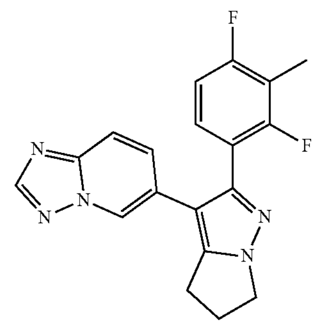 [SMILES: Cc1c(F)ccc(-c2nn3c(c2-c2ccc4ncnn4c2)CCC3)c1F] | 6-(2-(2,4-Difluoro-3-methylphenyl)-5,6-dihydro-4H-pyrrolo[1,2-b]pyrazol-3-yl)-[1,2,4]triazolo[1,5-a]pyridine |
| 174 | 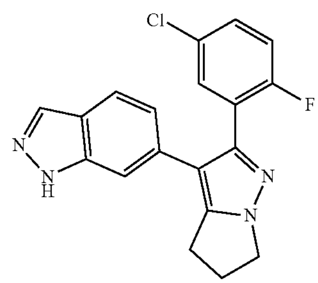 | 6-(2-(5-Chloro-2-fluorophenyl)-5,6-dihydro-4H-pyrrolo[1,2-b]pyrazol-3-yl)-1H-indazole |
| 175 | 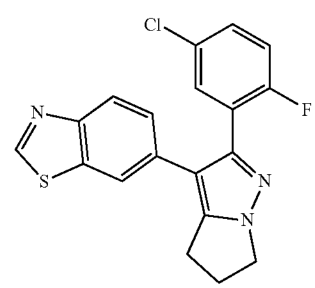 | 6-(2-(5-Chloro-2-fluorophenyl)-5,6-dihydro-4H-pyrrolo[1,2-b]pyrazol-3-yl)benzo[d]thiazole |
| 176 | 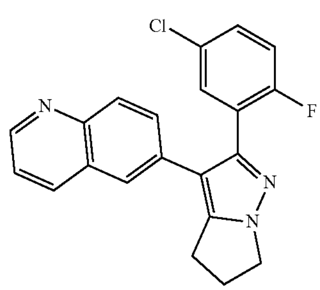 [SMILES: Fc1ccc(Cl)cc1-c1nn2c(c1-c1ccc3ncccc3c1)CCC2] | 6-(2-(5-Chloro-2-fluorophenyl)-5,6-dihydro-4H-pyrrolo[1,2-b]pyrazol-3-yl)quinoline |

-continued

| No. | Structure | Name |
|---|---|---|
| 177 | 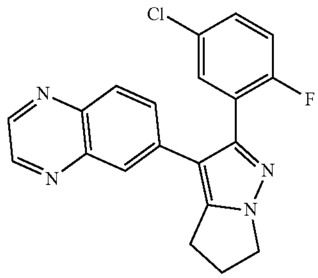 | 6-(2-(5-Chloro-2-fluorophenyl)-5,6-dihydro-4H-pyrrolo[1,2-b]pyrazol-3-yl)quinoxaline |
| 178 | 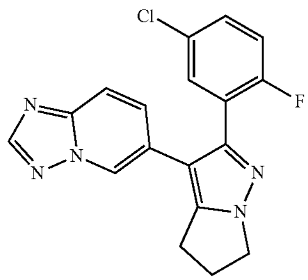 | 6-(2-(5-Chloro-2-fluorophenyl)-5,6-dihydro-4H-pyrrolo[1,2-b]pyrazol-3-yl)-[1,2,4]triazolo[1,5-a]pyridine |
| 179 | 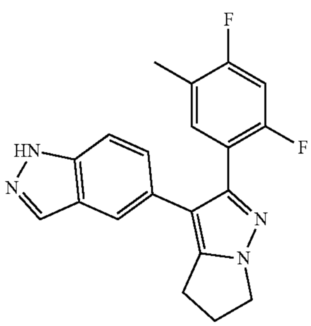 [SMILES: Cc1cc(-c2nn3c(c2-c2ccc4[nH]ncc4c2)CCC3)c(F)cc1F] | 5-(2-(2,4-Difluoro-5-methylphenyl)-5,6-dihydro-4H-pyrrolo[1,2-b]pyrazol-3-yl)-1H-indazole |
| 180 | 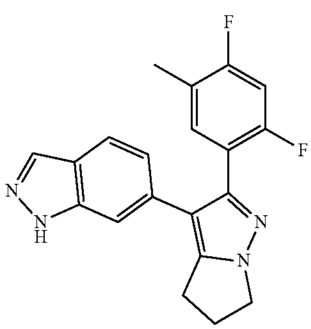 [SMILES: Cc1cc(-c2nn3c(c2-c2ccc4cn[nH]c4c2)CCC3)c(F)cc1F] | 6-(2-(2,4-Difluoro-5-methylphenyl)-5,6-dihydro-4H-pyrrolo[1,2-b]pyrazol-3-yl)-1H-indazole |
| 181 | 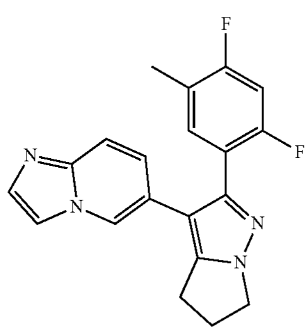 [SMILES: Cc1cc(-c2nn3c(c2-c2ccc4nccn4c2)CCC3)c(F)cc1F] | 6-(2-(2,4-Difluoro-5-methylphenyl)-5,6-dihydro-4H-pyrrolo[1,2-b]pyrazol-3-yl)imidazo[1,2-a]pyridine |

-continued

| No. | Structure | Name |
| --- | --- | --- |
| 182 | 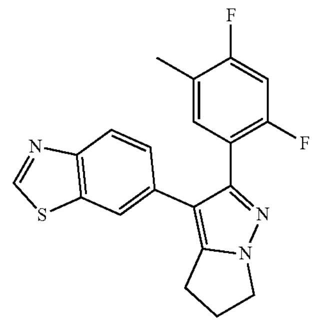 [SMILES: Cc1cc(-c2nn3c(c2-c2ccc4ncsc4c2)CCC3)c(F)cc1F] | 6-(2-(2,4-Difluoro-5-methylphenyl)-5,6-dihydro-4H-pyrrolo[1,2-b]pyrazol-3-yl)benzo[d]thiazole |
| 183 | 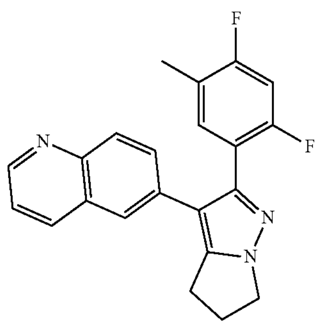 [SMILES: Cc1cc(-c2nn3c(c2-c2ccc4ncccc4c2)CCC3)c(F)cc1F] | 6-(2-(2,4-Difluoro-5-methylphenyl)-5,6-dihydro-4H-pyrrolo[1,2-b]pyrazol-3-yl)quinoline |
| 184 | 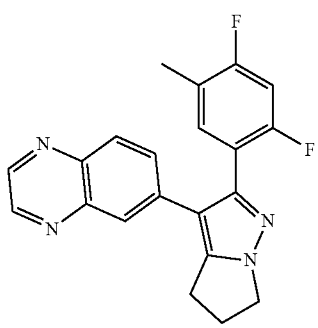 [SMILES: Cc1cc(-c2nn3c(c2-c2ccc4nccnc4c2)CCC3)c(F)cc1F] | 6-(2-(2,4-Difluoro-5-methylphenyl)-5,6-dihydro-4H-pyrrolo[1,2-b]pyrazol-3-yl)quinoxaline |
| 185 | 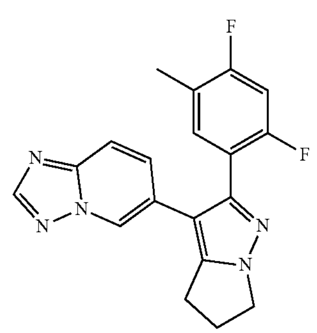 [SMILES: Cc1cc(-c2nn3c(c2-c2ccc4ncnn4c2)CCC3)c(F)cc1F] | 6-(2-(2,4-Difluoro-5-methylphenyl)-5,6-dihydro-4H-pyrrolo[1,2-b]pyrazol-3-yl)-[1,2,4]triazolo[1,5-a]pyridine |

-continued
| No. | Structure | Name |
|---|---|---|
| 186 | 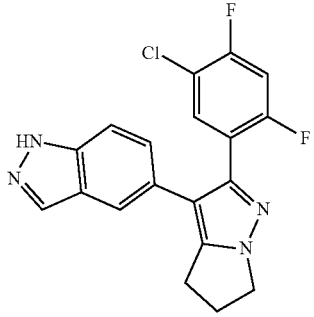 [SMILES: Fc1cc(F)c(-c2nn3c(c2-c2ccc4[nH]ncc4c2)CCC3)cc1Cl] | 5-(2-(5-Chloro-2,4-difluorophenyl)-5,6-dihydro-4H-pyrrolo[1,2-b]pyrazol-3-yl)-1H-indazole |
| 187 | 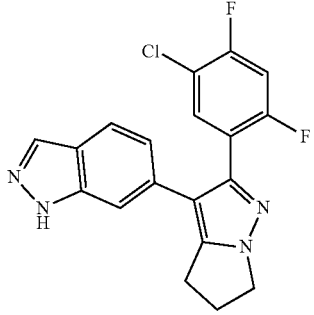 [SMILES: Fc1cc(F)c(-c2nn3c(c2-c2ccc4cn[nH]c4c2)CCC3)cc1Cl] | 6-(2-(5-Chloro-2,4-difluorophenyl)-5,6-dihydro-4H-pyrrolo[1,2-b]pyrazol-3-yl)-1H-indazole |
| 188 | 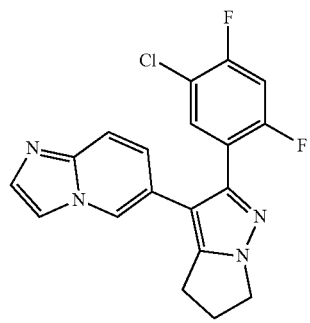 [SMILES: Fc1cc(F)c(-c2nn3c(c2-c2ccc4nccn4c2)CCC3)cc1Cl] | 6-(2-(5-Chloro-2,4-difluorophenyl)-5,6-dihydro-4H-pyrrolo[1,2-b]pyrazol-3-yl)imidazo[1,2-a]pyridine |
| 189 | 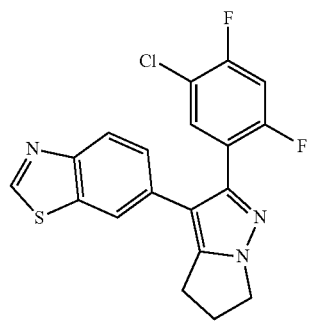 [SMILES: Fc1cc(F)c(-c2nn3c(c2-c2ccc4ncsc4c2)CCC3)cc1Cl] | 6-(2-(5-Chloro-2,4-difluorophenyl)-5,6-dihydro-4H-pyrrolo[1,2-b]pyrazol-3-yl)benzo[d]thiazole |

-continued

| No. | Structure | Name |
|---|---|---|
| 190 | 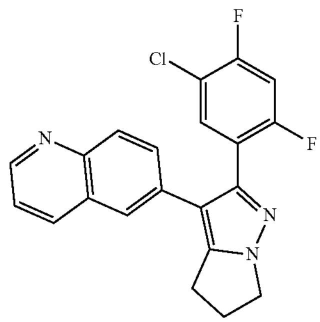 [SMILES: Fc1cc(F)c(-c2nn3c(c2-c2ccc4ncccc4c2)CCC3)cc1Cl] | 6-(2-(5-Chloro-2,4-difluorophenyl)-5,6-dihydro-4H-pyrrolo[1,2-b]pyrazol-3-yl)quinoline |
| 191 | 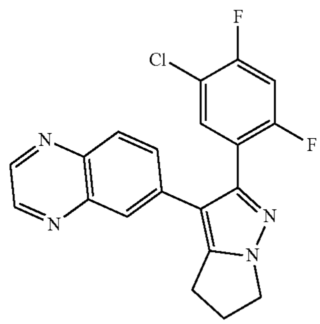 [SMILES: Fc1cc(F)c(-c2nn3c(c2-c2ccc4nccnc4c2)CCC3)cc1Cl] | 6-(2-(5-Chloro-2,4-difluorophenyl)-5,6-dihydro-4H-pyrrolo[1,2-b]pyrazol-3-yl)quinoxaline |
| 192 | 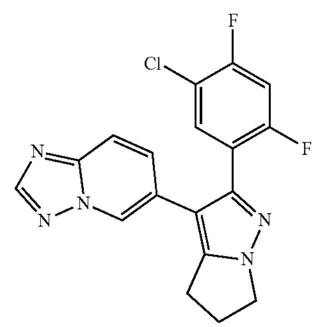 [SMILES: Fc1cc(F)c(-c2nn3c(c2-c2ccc4ncnn4c2)CCC3)cc1Cl] | 6-(2-(5-Chloro-2,4-difluorophenyl)-5,6-dihydro-4H-pyrrolo[1,2-b]pyrazol-3-yl)-[1,2,4]triazolo[1,5-a]pyridine |
| 193 | 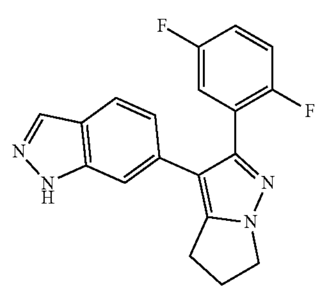 [SMILES: Fc1ccc(F)c(-c2nn3c(c2-c2ccc4cn[nH]c4c2)CCC3)c1] | 6-(2-(2,5-Difluorophenyl)-5,6-dihydro-4H-pyrrolo[1,2-b]pyrazol-3-yl)-1H-indazole |
| 194 | 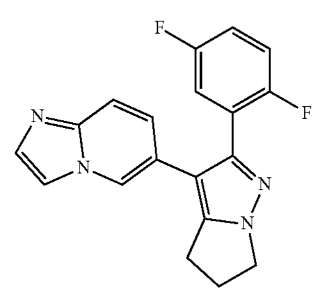 [SMILES: Fc1ccc(F)c(-c2nn3c(c2-c2ccc4nccn4c2)CCC3)c1] | 6-(2-(2,5-Difluorophenyl)-5,6-dihydro-4H-pyrrolo[1,2-b]pyrazol-3-yl)imidazo[1,2-a]pyridine |

-continued
| No. | Structure | Name |
|---|---|---|
| 195 | 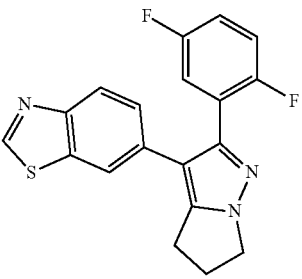 [SMILES: Fc1ccc(F)c(-c2nn3c(c2-c2ccc4ncsc4c2)CCC3)c1] | 6-(2-(2,5-Difluorophenyl)-5,6-dihydro-4H-pyrrolo[1,2-b]pyrazol-3-yl)benzo[d]thiazole |
| 196 | 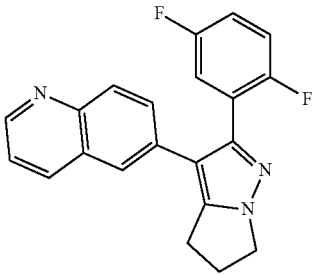 [SMILES: Fc1ccc(F)c(-c2nn3c(c2-c2ccc4ncccc4c2)CCC3)c1] | 6-(2-(2,5-Difluorophenyl)-5,6-dihydro-4H-pyrrolo[1,2-b]pyrazol-3-yl)quinoline |
| 197 | 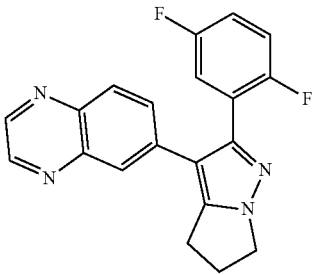 [SMILES: Fc1ccc(F)c(-c2nn3c(c2-c2ccc4nccnc4c2)CCC3)c1] | 6-(2-(2,5-Difluorophenyl)-5,6-dihydro-4H-pyrrolo[1,2-b]pyrazol-3-yl)quinoxaline |
| 198 | 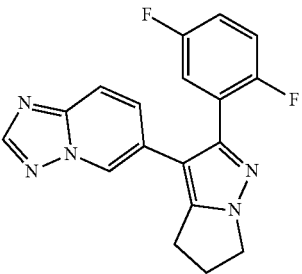 [SMILES: Fc1ccc(F)c(-c2nn3c(c2-c2ccc4ncnn4c2)CCC3)c1] | 6-(2-(2,5-Difluorophenyl)-5,6-dihydro-4H-pyrrolo[1,2-b]pyrazol-3-yl)-[1,2,4]triazol[1,5-a]pyridine |
| 199 | 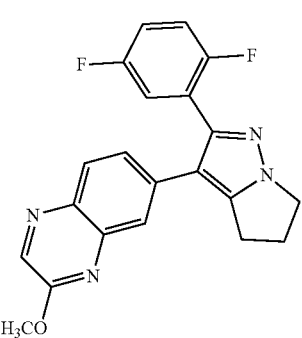 [SMILES: COc1cnc2ccc(-c3c(-c4cc(F)ccc4F)nn4c3CCC4)cc2n1] | 7-(2-(2,5-difluorophenyl)-5,6-dihydro-4H-pyrrolo[1,2-b]pyrazol-3-yl)-2-methoxyquinoxaline |

| No. | Structure | Name |
|---|---|---|
| 200 | 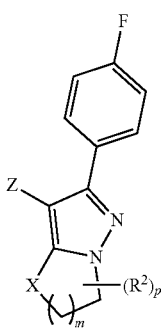 | 7-(2-(2,5-difluorophenyl)-5,6-dihydro-4H-pyrrolo[1,2-b]pyrazol-3-yl)-2-(2-methoxyethoxy)quinoxaline |
| 201 | 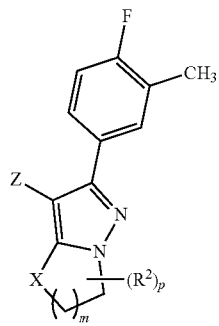 | 6-(2-(2-fluorophenyl)-5,6-dihydro-4H-pyrrolo[1,2-b]pyrazol-3-yl)benzo[d]thiazole |
In embodiment II$_1$ of this aspect, the invention comprises compounds of any one of embodiments I$_1$-I$_5$ having the structure of any one of formulae (IIa)-(IIq):
(IIa)
(IIb)
(IIc)
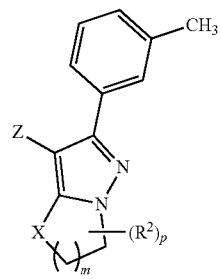
(IId)
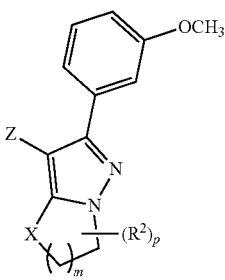

-continued
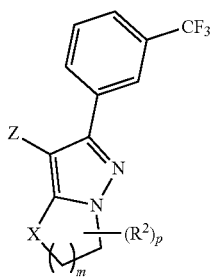 (IIe)
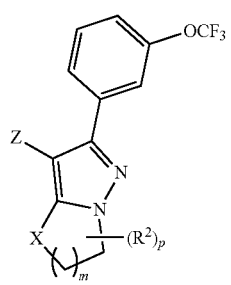 (IIf)
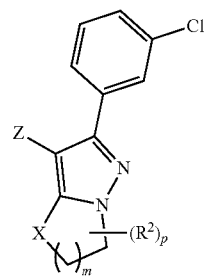 (IIg)
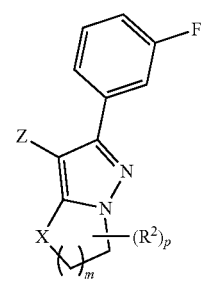 (IIh)
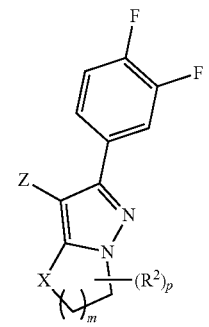 (IIi)
-continued
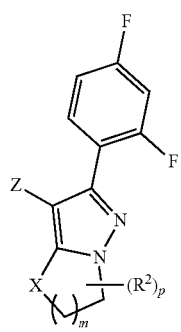 (IIj)
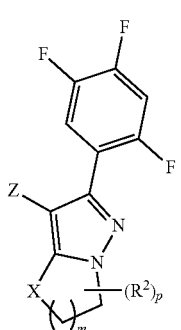 (IIk)
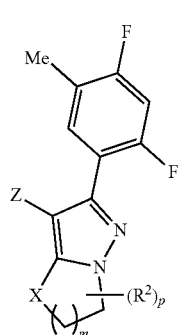 (IIl)
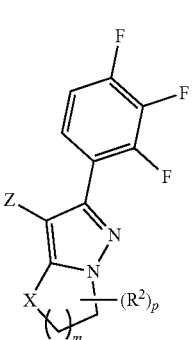 (IIm)
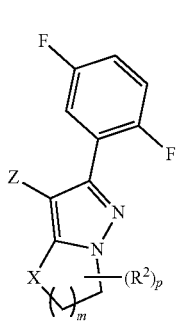 (IIn)

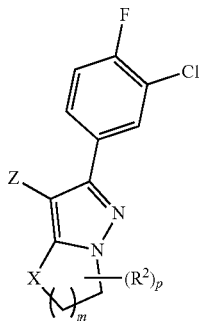

(IIo)

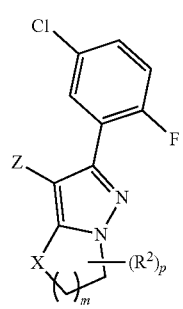

(IIp)

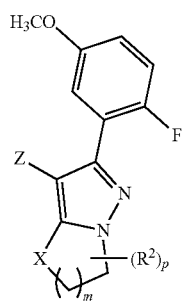

(IIq)

wherein X, Z, m, n, p, $R^1$ and $R^2$ are as described in any one of the above embodiments.

Particular embodiments of this aspect of the invention comprise compounds of any one of the formulae (IIa)-(IIq), each as defined in each of the following rows (or a pharmaceutically acceptable salt, prodrug, or N-oxide thereof, or a solvate or hydrate thereof), wherein each entry is a group number as defined above (e.g., (3m) refers to $R^2$ independently being $C_1$-$C_3$alkyl), and a dash "-" indicates that the variable is as defined in any one of embodiments $I_1$-$I_5$ or defined according to any one of the applicable variable definitions (IIa)-(IIq), (3a)-(3o), and (4a)-(4sss). Thus, in particular embodiment compounds of any one of formulae (IIa)-(IIq) is wherein:

|  | $R^2$ | Z | m | X |
|---|---|---|---|---|
| (2)-1 | absent | (4a) | 1 | $CH_2$ |
| (2)-2 | absent | (4a) | 2 | $CH_2$ |
| (2)-3 | absent | (4o) | 1 | O |
| (2)-4 | absent | (4o) | 2 | O |
| (2)-5 | absent | (4cc) | 1 | $CH_2$ |
| (2)-6 | absent | (4cc) | 2 | $CH_2$ |
| (2)-7 | absent | (4ff) | 1 | O |
| (2)-8 | absent | (4ff) | 2 | O |
| (2)-9 | absent | (4lll) | 1 | $CH_2$ |
| (2)-10 | absent | (4lll) | 2 | $CH_2$ |
| (2)-11 | absent | (4qqq) | 1 | O |
| (2)-12 | absent | (4qqq) | 2 | O |
| (2)-13 | absent | (4rrr) | 1 | $CH_2$ |
| (2)-14 | absent | (4rrr) | 2 | $CH_2$ |
| (2)-15 | absent | (4a) | 1 | O |
| (2)-16 | absent | (4a) | 2 | O |
| (2)-17 | absent | (4o) | 1 | $CH_2$ |
| (2)-18 | absent | (4o) | 2 | $CH_2$ |
| (2)-19 | absent | (4cc) | 1 | O |
| (2)-20 | absent | (4cc) | 2 | O |
| (2)-21 | absent | (4ff) | 1 | $CH_2$ |
| (2)-22 | absent | (4ff) | 2 | $CH_2$ |
| (2)-23 | absent | (4lll) | 1 | O |
| (2)-24 | absent | (4lll) | 2 | O |
| (2)-25 | absent | (4qqq) | 1 | $CH_2$ |
| (2)-26 | absent | (4qqq) | 2 | $CH_2$ |
| (2)-27 | absent | (4rrr) | 1 | O |
| (2)-28 | absent | (4rrr) | 2 | O |
| (2)-29 | (3a) | (4a) | 1 | $CH_2$ |
| (2)-30 | (3a) | (4a) | 2 | $CH_2$ |
| (2)-31 | (3a) | (4o) | 1 | O |
| (2)-32 | (3a) | (4o) | 2 | O |
| (2)-33 | (3a) | (4cc) | 1 | $CH_2$ |
| (2)-34 | (3a) | (4cc) | 2 | $CH_2$ |
| (2)-35 | (3a) | (4ff) | 1 | O |
| (2)-36 | (3a) | (4ff) | 2 | O |
| (2)-37 | (3a) | (4lll) | 1 | $CH_2$ |
| (2)-38 | (3a) | (4lll) | 2 | $CH_2$ |
| (2)-39 | (3a) | (4qqq) | 1 | O |
| (2)-40 | (3a) | (4qqq) | 2 | O |
| (2)-41 | (3a) | (4rrr) | 1 | $CH_2$ |
| (2)-42 | (3a) | (4rrr) | 2 | $CH_2$ |
| (2)-43 | (3a) | (4a) | 1 | O |
| (2)-44 | (3a) | (4a) | 2 | O |
| (2)-45 | (3a) | (4o) | 1 | $CH_2$ |
| (2)-46 | (3a) | (4o) | 2 | $CH_2$ |
| (2)-47 | (3a) | (4cc) | 1 | O |
| (2)-48 | (3a) | (4cc) | 2 | O |
| (2)-49 | (3a) | (4ff) | 1 | $CH_2$ |
| (2)-50 | (3a) | (4ff) | 2 | $CH_2$ |
| (2)-51 | (3a) | (4lll) | 1 | O |
| (2)-52 | (3a) | (4lll) | 2 | O |
| (2)-53 | (3a) | (4qqq) | 1 | $CH_2$ |
| (2)-54 | (3a) | (4qqq) | 2 | $CH_2$ |
| (2)-55 | (3a) | (4rrr) | 1 | O |
| (2)-56 | (3a) | (4rrr) | 2 | O |
| (2)-57 | (3n) | (4a) | 1 | $CH_2$ |
| (2)-58 | (3n) | (4a) | 2 | $CH_2$ |
| (2)-59 | (3n) | (4o) | 1 | O |
| (2)-60 | (3n) | (4o) | 2 | O |
| (2)-61 | (3n) | (4cc) | 1 | $CH_2$ |
| (2)-62 | (3n) | (4cc) | 2 | $CH_2$ |
| (2)-63 | (3n) | (4ff) | 1 | O |
| (2)-64 | (3n) | (4ff) | 2 | O |
| (2)-65 | (3n) | (4lll) | 1 | $CH_2$ |
| (2)-66 | (3n) | (4lll) | 2 | $CH_2$ |
| (2)-67 | (3n) | (4qqq) | 1 | O |
| (2)-68 | (3n) | (4qqq) | 2 | O |
| (2)-69 | (3n) | (4rrr) | 1 | $CH_2$ |
| (2)-70 | (3n) | (4rrr) | 2 | $CH_2$ |
| (2)-71 | (3n) | (4a) | 1 | O |
| (2)-72 | (3n) | (4a) | 2 | O |
| (2)-73 | (3n) | (4o) | 1 | $CH_2$ |
| (2)-74 | (3n) | (4o) | 2 | $CH_2$ |
| (2)-75 | (3n) | (4cc) | 1 | O |
| (2)-76 | (3n) | (4cc) | 2 | O |
| (2)-77 | (3n) | (4ff) | 1 | $CH_2$ |
| (2)-78 | (3n) | (4ff) | 2 | $CH_2$ |
| (2)-79 | (3n) | (4lll) | 1 | O |
| (2)-80 | (3n) | (4lll) | 2 | O |
| (2)-81 | (3n) | (4qqq) | 1 | $CH_2$ |
| (2)-82 | (3n) | (4qqq) | 2 | $CH_2$ |
| (2)-83 | (3n) | (4rrr) | 1 | O |
| (2)-84 | (3n) | (4rrr) | 2 | O |

In some embodiments, the compound of formula (I) is one of the following compounds (or a pharmaceutically acceptable salt, prodrug, or N-oxide thereof, or a solvate or hydrate thereof): 7, 8, 24, 33, 34, 38, 104, 114, 122, 124, 127, 165, 175, 177, 178, 185, 188, and 192.

In another aspect, the present invention comprises pharmaceutical compositions comprising a compound according to any one of the preceding aspects of the invention or any embodiment thereof, together with a pharmaceutically acceptable excipient, diluent, or carrier.

In another aspect, the invention comprises the use of a compound described by any one of the preceding aspects of the invention or any embodiment thereof, for the preparation of a medicament for the treatment of medical diseases or conditions that benefit from the inhibition of cytokine signaling. Medical conditions contemplated in this aspect include all diseases and conditions described herein.

The compounds of the disclosure described above are useful as kinase inhibitors and/or inhibitors of cytokine signaling. Exemplary kinases inhibited by the presently disclosed compounds include, without limitation, ACVR1; ACVR1B (ALK-4); ACVR1C; ACVR2A; ACVR2B; ACVRL1; BMPR1A; BMPR1B; BMPR2; TGFBR1 (ALK-5), PI3K and MAP4K4 (HGK). Exemplary cytokines, the signaling of which is inhibited by the present compounds include, without limitation, TGF-β superfamily, including Activin, Nodal, TGF-β1, and GDF-8. In one aspect the present compounds are selective for one or more kinase and/or cytokine signaling pathway. For example, exemplary compounds inhibit TGF-β1 signaling, GDF-8 signaling, or both. In one aspect the present compounds inhibit GDF-8 signaling preferentially to TGF-β1 signaling, such that GDF8 signaling is inhibited at least about 1.5-fold more potently or from about 1.1-fold to about 25-fold more potently. In one embodiment certain compounds inhibit GDF8 signaling at least about 5-fold more potently, such as from about 8-fold to about 50-fold, or at least about 10-fold more potently, such as from about 15-fold to about 300-fold more potently.

In particular, the present compounds can be use to treat disorders, such as pulmonary hypertension, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, atherosclerosis, peritoneal and sub-dermal adhesion, kidney fibrosis, lung fibrosis, including idiopathic pulmonary fibrosis, and liver fibrosis, hepatitis B, hepatitis C, alcohol-induced hepatitis, cancer, haemochromatosis, primary biliary cirrhosis, restenosis, retroperitoneal fibrosis, mesenteric fibrosis, endometriosis, keloids, cancer, abnormal bone function, inflammatory disorders, scarring and photoaging of the skin.

Particular proliferative diseases that can be treated with the present compounds include those selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, melanoma, psoriasis, prostate hyperplasia, a neoplasia, a neoplasia of epithelial character, leukemias and lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

The compounds described herein also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, $^{18}$F etc. Thus, the disclosed compounds may be enriched in one or more of these isotopes relative to the natural abundance of such isotope. As is known to those of skill in the art, such isotopically enriched compounds are useful for a variety of purposes. For example, substitution with heavier isotopes such as deuterium ($^2$H) may afford certain therapeutic advantages that result from greater metabolic stability. Substitution with positron emitting isotopes, such as 18F can be useful in Positron Emission Tomography (PET) studies. By way of example, deuterium ($^2$H) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

In another aspect, the invention comprises combination therapies for the treatment of cancer, including both pre-malignant and malignant neoplasms. In this aspect, the invention comprises a method of treating cancer comprising administering to a subject a compound disclosed herein in conjunction with a therapeutic treatment of cancer. In some embodiments of the invention, the compounds disclosed herein are used in combination of standard of care anti-proliferative treatments of cancer. The amount of a compound disclosed herein for use in the combination therapy is an amount sufficient to inhibit signaling by members of the TGF-β superfamily, such as Nodal and Activin, which promote the survival and/or differentiation of cancer stem cells and thereby enhance the efficacy of the therapeutic treatment. Treatment with the present compounds thus blocks the ability of cancer stem cells to recapitulate a tumor destroyed by treatment with standard of care. Efficacy of treatment can be determined by any art recognized method generally employed for the particular cancer being treated and includes, for example, retardation, inhibition, or regression of tumor growth.

Reference to "combination therapy" and treatment with a compound disclosed herein "in conjunction with" another therapeutic treatment means that the compound and other therapeutic treatment can be administered simultaneously or sequentially such that the resultant treatment is more efficacious than either treatment alone.

One embodiment of treating cancer in a subject comprises administering to a subject in need thereof an amount described above of a compound disclosed herein in combination with the administration of a therapeutically effective amount of one or more chemotherapeutic agents, wherein the one or more chemotherapeutic agents is selected from the group consisting of antimetabolites, alkylating agents, coordination compounds, platinum complexes, DNA cross-linking compounds, inhibitors of transcription enzymes, tyrosine kinase inhibitors, protein kinase inhibitors, topoisomerase inhibitors, DNA minor-groove binding compounds, vinca alkyloids, taxanes, antitumor antibiotics, hormones, aromatase inhibitors, enzymes, growth factor receptors antibodies, cytokines, cell surface markers antibodies, HDAC inhibitors, HSP 90 inhibitors, BCL-2 inhibitors, B-raf inhibitors, MEK inhibitors, mTOR inhibitors, proteasome inhibitors and monoclonal antibodies.

Among the BCL-2 inhibitors useful in the invention is ABT-199.

Another embodiment of methods for treating a subject comprises administering to the subject an amount (as described above) of a compound disclosed herein in combination with the administration of a therapeutically effective amount of one or more chemotherapeutic agents, the one or more chemotherapeutic agents being independently selected from the group consisting of mechlorothamine, cyclophosphamide, ifosfamide, melphalan, chlorambucil, ethyleneimines, methylmelamines, procarbazine, dacarbazine, temozolomide, busulfan, carmustine, lomustine, methotrexate, fluorouracil, capecitabine, cytarabine, gemcitabine, cytosine arabinoside, mecaptopurine, fludarabine, cladribine, thioguanine, azathioprine, vinblastine, vincristine, paclitaxel, docetaxel, colchicine, actinomycin D, daunorubicin, bleomycin, L-asparaginase, cisplatin, carboplatin, oxaliplatin, prednisone, dexamethasone, amino glutethimide, formestane, anastrozole, hydroxyprogesterone caproate, medroxyprogesterone, tamoxifen, amsacrine, mitoxantrone, topotecan, irinotecan, camptothecin, afatinib, axitinib, bosutinib, bortezomib, carfilzomib, cabozantinib, cediranib, crizotinib, dasatinib, dabrafenib, evorolimus, ibrutinib, LDK378, LGX818, MEK162, regorafenib, ruxolitinib, selumetinib, sorafenib, trametinib, vemurafenib, erlotinib, gefitinib, imatinib, lapatinib, lestaurtinib, nilotinib, palbociclib, pazopanib, pomatinib, semaxanib, sirolimus, sunitinib, temsirolimus, vatalanib, vandetanib, anti Her2 antibodies, interferon-α, interferon-γ, interleukin 2, GM CSF, anti CTLA 4 antibodies, rituximab, anti CD33 antibodies, MGCD0103, vorinostat, 17-AAG, thalidomide, lenalidomide, rapamycin, CCI-779, doxorubicine, gemcitabine, melphalan, NPI052, gemtuzumab, alemtuzumab, cetuximab, ibritumomab tiuxaetan, tositumomab, iodine-131 tositumomab, trastuzumab, ado-trastuzumab emtansine, obinutuzumab, bevacizumab, rituximab, and anti-TRAIL death receptor antibodies.

Among the CTLA 4 antibodies that can be used in the present invention is ipilimumab, marketed as YERVOY® by Bristol-Myers Squibb.

Other chemotherapeutic agents for combination with the presently disclosed TGF-β signaling inhibitors include checkpoint pathway inhibitors, e.g., PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed TGF-β signaling inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The following table displays exemplary cancers treatable in the combination therapies of the invention and the therapeutic drug and/or other treatment for use with the compounds disclosed herein:

| Cancer | Drug or Treatment |
|---|---|
| Glioma | lomustine, temozolide and/or radiation |
| hepatocellular carcinoma | sorafenib, regorafenib |
| myelodysplastic syndromes | decitabine or azacytidine |
| pancreatic cancer | Gemcitabine |
| ovarian cancer, such as epithelial ovarian carcinoma | carboplatin, cisplatin, doxorubicin, gemcitabine, paclitaxel |
| breast cancer | Trastuzumab |
| basal and squamous skin carcinomas | 5-fluorouracil, imiquimod, photodynamic therapy (e.g. with 5-aminolevulinic acid), |
| head and neck carcinoma | bleomycin, cisplatin, cetuximab, docetaxel, fluorouracil, methotrexate |
| triple negative breast cancer | Paclitaxel |
| Prostate | abiraterone, enzalutamide |

In another aspect, the invention comprises a method of determining and measuring the ability of the compounds disclosed herein to inhibit signaling by members of the TGF-β superfamily, such as Nodal and Activin, in order to identify cancers and, more specifically, tumors. In one embodiment, neoplasms susceptible to such combination therapy can be identified by testing for Nodal and Activin signaling activity using techniques known to those skilled in the art, including, for example, assays described in Lonardo, E. et al. (2011) Cell Stem Cell 9, 433-446 (which is hereby incorporated by reference in its entirety). Optionally in this embodiment, where the tested compound is found to inhibit signaling of a member of the TGF-β superfamily, such as Nodal and Activin, in the tested neoplasm, the compound is subsequently used in a combination therapy for treatment of the neoplasm, as described herein.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B-, wherein a is 0 or 1. In such instances, when a is 0 the moiety is B- and when a is 1 the moiety is A-B-.

As used herein, the term "alkyl" includes alkyl, alkenyl and alkynyl groups of a designed number of carbon atoms, such as 1 to 6 carbons (i.e., inclusive of 1 and 6), 1 to 6 carbons, 1 to 3 carbons, or 1, 2, 3, 4, 5 or 6. The term "$C_m$-$C_n$alkyl" means an alkyl group having from m to n carbon atoms (i.e., inclusive of m and n). The term "$C_m$-$C_n$alkyl" means an alkyl group having from m to n carbon atoms. For example, "$C_1$-$C_6$alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$alkyl"), the group is simply a single covalent bond if it is a divalent radical or is a hydrogen atom if it is a monovalent radical. For example, the moiety "—($C_0$-$C_6$alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 6 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" or "Ar" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" or "Het" refers to an aromatic ring system containing at least one heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic ring, for example, cycloalkyl or heterocycloalkyl rings, wherein the cycloalkyl (Cak) and heterocycloalkyl (Hca) rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" or "Hca" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorphinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" or "Cak" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "substituted," when used to modify a specified group or radical, means that one or more hydrogen atoms of the specified group or radical are each, independently of one another, replaced with the same or different substituent groups as defined below, unless specified otherwise.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxoglutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}F$. Similarly, compounds may be enriched in the heavy isotopes of hydrogen: deuterium and tritium; and similarly can be enriched in a radioactive isotope of carbon, such as $^{13}C$. Such isotopic variant compounds undergo different metabolic pathways and can be useful, for example, in studying the ubiquitination pathway and its role in disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" an enzyme with a compound includes the administration of a compound described herein to an individual or patient, such as a human, as well as, for example, introducing a compound into a sample containing a cellular or purified preparation containing the enzyme.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed or otherwise susceptible to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease (including a symptom thereof); for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof; or (ii) eliciting the referenced biological effect (e.g., modulation or inhibition of GDF-8 or TGF-β1).

Manifestation of amelioration of a disease condition by inhibiting GDF-8 or TGF-131 may require the concomitant or sequential administration of additional therapeutic agents, such as antineoplastic agents in the case of cancer, or antiretroviral agents in the case of viral diseases. For example, administration of GDF-8 and TGF-β1 inhibitors for the treatment of cancer does not always produce a direct antitumor effect when used as a single agent. However, when combined with chemotherapeutic drugs (antineoplastic) the antitumor effect observed is higher than the sum of effects of each agent alone. In one embodiment the present compounds are used as immunomodulators to increase an immune response or to abrogate a tumor's ability to evade the immune response. In one embodiment of a method for using the present compounds, one or more inhibitor of TGF-β receptor superfamily signaling is used in combination with an immunooncology treatment.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical Formulations and Dosage Forms

The compounds of the disclosure can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to any one of structural formulae.

In the pharmaceutical compositions disclosed herein, one or more compounds of the disclosure may be present in association with one or more pharmaceutically acceptable carriers, diluents or excipients, and, if desired, other active ingredients. The pharmaceutical compositions containing compounds of the disclosure may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of the disclosure can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of the disclosure can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-3, or analogous synthetic schemes.

One of skill in the art can adapt the reaction sequences of Schemes 1 and 2 to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

Compounds suitable for use in the presently disclosed pharmaceutical compositions include compounds of Table 1, above. These compounds can be made according to the general schemes described above, for example using a procedure similar to that described below in the Examples.

The following examples are intended to further illustrate certain embodiments and are not intended to limit the scope of the presently disclosed compounds.

EXAMPLES

Example 1: Synthesis and Characterization

Scheme 1
General Scheme for the Preparation of 1-aminopyrrolidin-2-one precursor

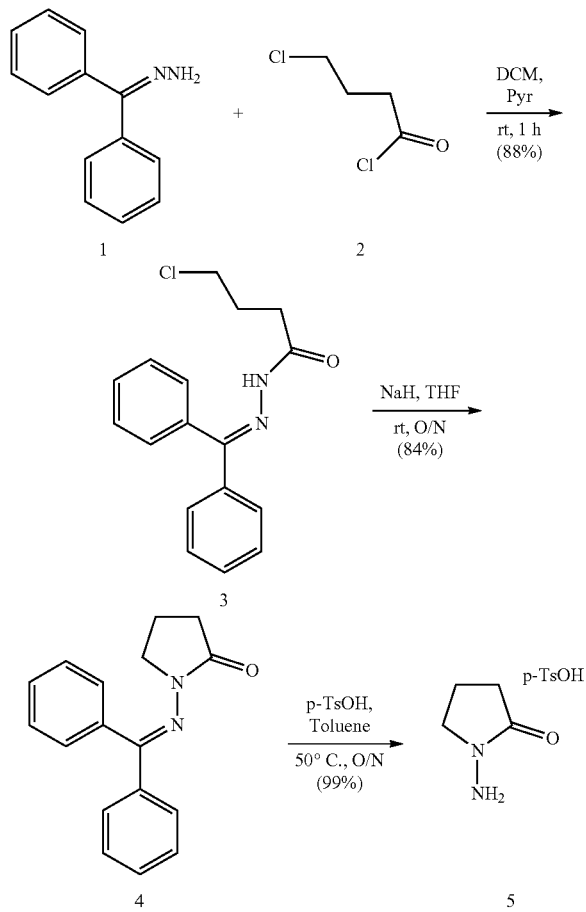

Synthesis of 1-aminopyrrolidin-2-one p-toluenesulfonic acid was carried out following two publications: 1) Taylor, E. C. et al. JACS 1981, 103(26), 7743; and 2) Mundla, S. V. PCT WO2007/018818.

Step 1 To a solution of benzophenone hydrazone (35 g, 178.3 mmol) and pyridine (14.4 mL, 14.1 g, 178.3 mmol) in dichloromethane (200 mL), 4-chlorobutyryl chloride (20 mL, 25.1 g, 178.3 mmol) was added dropwise to allow the reaction to reflux gently. When the addition was complete, the reaction mixture was heated at 50° C. in an oil bath for 15 min., cooled down to room temperature and extracted with water (2×100 mL), and brine (1×100 mL), dried (MgSO4), filtered and concentrated to give a white residue. Trituration with 2-propanol (2×) provided 4-chloro-N-(diphenylmethylene)butanehydrazide (3) as a white solid, wt. 47.1 g (88%). $^1$H NMR (CDCl$_3$, 300 MHz) δ 8.40 (s, 1H), 7.63-7.54 (m, 5H), 7.43-7.34 (m, 3H), 7.30-7.25 (m, 2H), 3.74 (t, J=6.4 Hz, 2H), 3.09 (t, J=7.2 Hz, 2H), 2.27 (p, J=7.0 Hz, 2H). MS m/e: 370 (M+H)±. MS m/e: 301 (M+H)±.

Step 2 To a solution of 4-chloro-N-(diphenylmethylene) butanehydrazide (47.1 g, 156.5 mmol) in THF (500 mL), sodium hydride (60% wt., 6.8 g, 170 mmol) was added in small portions. A significant amount of H$_2$ gas evolved and a precipitate was formed in less than 10 min. The resulting reaction mixture was allowed to stir at room temperature under N2 atmosphere. To the yellow creamy solution, saturated ammonium chloride solution (300 mL) was added and the organic layer separated. The aqueous layer was then washed with ethyl acetate (2×100 mL), and the organic layers were combined, dried (MGsO$_4$), filtered and concentrated. The resulting white solid was triturated with 2-propanol and hexanes to give a number of lots of 1-((diphenylmethylene)amino)pyrrolidin-2-one (4) with similar purity, wt. 34.9 g (84%). $^1$H NMR (CDCl$_3$, 300 MHz) δ 7.64-7.55 (m, 2H), 7.46-7.37 (m, 4H), 7.37-7.27 (m, 4H), 3.32 (t, J=7.0 Hz, 2H), 2.34 (t, J=8.0 Hz, 2H), 1.93 (p, J=7.4 Hz, 2H). MS m/e: 265 (M+H)±.

Step 3 To a solution of 1-((diphenylmethylene)amino) pyrrolidin-2-one (4, 34.9 g, 132.0 mmol) in toluene (500 mL) and water (2.4 mL, 132.8 mmol) warmed up to 45° C., p-toluenesulfonic acid was added (27.6 g, 145.1 mmol). The reaction mixture was then allowed to stir at 45° C. overnight and cooled down to room temperature. The resulting solid was filtered and re-suspended in toluene, stirred for 2 h., filtered, washed with toluene and dried overnight under vacuum to give 1-aminopyrrolidin-2-one 4-toluenesulfonic acid (5) as a white solid, wt. 35.9 g (quantitative). $^1$H NMR (DMSO-d$_6$, 300 MHz) δ 7.50 (d, J=8.0 Hz, 2H), 7.14 (d, J=8.4 Hz, 2H), 3.52 (t, J=6.9 Hz, 2H), 2.37 (t, J=7.7 Hz, 2H), 2.33 (s, 3H), 2.07 (p, J=7.3 Hz, 2H). MS mile: 101 (M+H)±.

Scheme 2
General Scheme for the Preparation of 1-aminopyrrolidin-2-one precursor

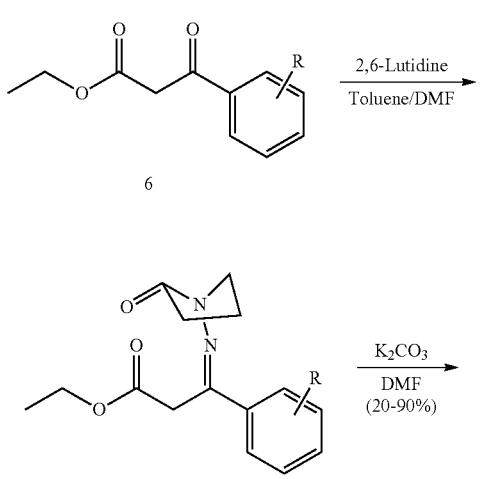

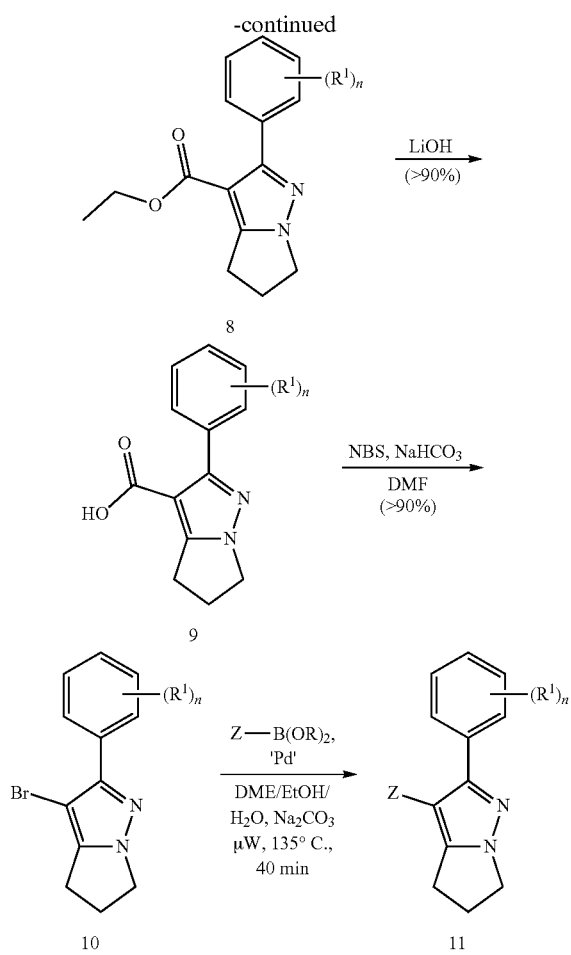

Step 1: A solution of ethyl 3-(2,5-difluorophenyl)-3-oxopropanoate (2.94 g, 12.9 mmol, prepared in 91% yield as described by Clay, R. J. et al. Synthesis 1993, 3, 290), 1-aminopyrrolidin-2-one 4-toluenesulfonic acid (4.2 g, 15.4 mmol), 2,6-lutidine (3.9 mL, 3.6 g, 33.5 mmol) in a mixture of toluene (130 mL) and N,N-dimethylformamide (40 mL) was heated at 135° C. using Dean-Stark apparatus for 5 h. Since trace amounts of starting materials were detected after 5 h., the reaction mixture was cooled down to 50° C. and potassium carbonate (3.74 g, 27 mmol) was added. The resulting reaction mixture was then allowed to stir at 135° C. overnight, cooled down to room temperature, concentrated and ethyl acetate (100 mL) and saturated ammonium chloride (100 mL) were added. The organic layer was separated and the aqueous layer was extracted with ethyl acetate (3×50 mL), and the combined organic layer was dried (MgSO4), filtered and concentrated. Column chromatography (DCM for 10 min followed by 50% ethyl acetate in dichloromethane) provided ethyl 2-(2,5-difluorophenyl)-5,6-dihydro-4H-pyrrolo[1,2-b]pyrazole-3-carboxylate (8) as a yellow solid, wt. 1.56 g (41%). $^1$H NMR (CDCl$_3$, 300 MHz) δ 7.24-7.16 (m, 1H), 7.09-7.02 (m, 2H), 4.23 (t, J=7.3 Hz, 2H), 4.19 (q, J=7.0 Hz, 2H), 3.17 (t, J=7.3 Hz, 2H), 2.68 (p, J=7.4 Hz, 2H), 1.20 (t, J=7.1 Hz, 3H). MS m/e: 293 (M+H)±.

Step 2: To a solution of ethyl 2-(2,5-difluorophenyl)-5,6-dihydro-4H-pyrrolo[1,2-b]pyrazole-3-carboxylate (8, 1.56 g, 5.3 mmol) in a mixture of THF/EtOH (2:1, 15 mL), a solution of LiOH.H$_2$O (1.21 g, 26.7 mmol) in H$_2$O (5 mL) was added. The resulting reaction mixture was allowed to stir at 85° C. for 6 h., and at room temperature overnight. The organic solvents were evaporated, water was added (20 mL) and the basic aqueous layer was acidified to pH 5 using concentrated HCl. The resulting white solid was filtered, washed and air dried overnight to provide 2-(2,5-difluorophenyl)-5,6-dihydro-4H-pyrrolo[1,2-b]pyrazole-3-carboxylic acid (9) as a white solid, wt. 1.32 g (94%). $^1$H NMR (DMSO-d$_6$, 300 MHz) δ 12.14 (s, 1H), 7.35-7.26 (m, 3H), 4.21 (t, J=7.3 Hz, 2H), 3.08 (t, J=7.4 Hz, 2H), 2.62 (p, J=7.3 Hz, 2H). MS m/e: 265 (M+H)±.

Step 3: To a solution of 2-(2,5-difluorophenyl)-5,6-dihydro-4H-pyrrolo[1,2-b]pyrazole-3-carboxylic acid (9, 1.32 g, 5.0 mmol), sodium bicarbonate (1.26 g, 15 mmol) in DMF (20 mL), N-bromosuccinimide (0.98 g, 5.5 mmol) was added. The resulting reaction mixture was allowed to stir at room temperature until all starting material is consumed (usually takes 1-2 h.), and then transferred dropwise to a flask containing water (100 mL) to give the product 3-bromo-2-(2,5-difluorophenyl)-5,6-dihydro-4H-pyrrolo[1,2-b]pyrazole 10 as a white solid, wt. 1.44 g (96%). $^1$H NMR (DMSO-d$_6$, 300 MHz) δ 7.50-7.26 (m, 3H), 4.24 (t, J=7.3 Hz, 2H), 2.92 (t, J=7.2 Hz, 2H), 2.62 (p, J=7.3 Hz, 2H). MS m/e: 299 (M+H)±.

Step 4: A degassed solution of 3-bromo-2-(2,5-difluorophenyl)-5,6-dihydro-4H-pyrrolo[1,2-b]pyrazole (10, 35 mg, 0.12 mmol), 5-(4,4,5,5-tetramethyl-1,3,2-dioxaborolan-2-yl)-1H-indazole (34 mg, 0.14 mmol),), tetrakis(triphenylphosphine)palladium(0) (30 mg. 26 μmol) and aqueous Na$_2$CO$_3$ (2 M, 0.2 mL, 0.4 mmol) in a mixture of DME/EtOH/H$_2$O (7:3:2, 1.0 mL) was irradiated in the microwave at 135° C. for 35 min. The reaction mixture was then dried (MgSO$_4$), filtered and concentrated under reduced pressure to give a black residue which was purified by HPLC to provide 5-(2-(2,5-difluorophenyl)-5,6-dihydro-4H-pyrrolo[1,2-b]pyrazol-3-yl)-1H-indazole (Compound 1). $^1$H NMR (DMSO-d$_6$, 300 MHz) δ 13.04 (br s, 1H), 8.01 (s, 1H), 7.53 (dd, J=1.6, 0.8 Hz, 1H), 7.47 (dt, J=8.6, 0.9 Hz, 1H), 7.33-7.21 (m, 3H), 7.14 (dd, J=8.6, 1.6 Hz, 1H), 4.24 (t, J=7.2 Hz, 2H), 3.09 (t, J=7.2 Hz, 2H), 2.67 (p, J=7.2 Hz, 2H). MS m/e: 337 (M+H)±. MS m/e: 337 (M+H)±.

Compound 2: 5-(2-(4-Fluoro-3-methylphenyl)-5,6-dihydro-4H-pyrrolo[1,2-b]pyrazol-3-yl)-1H-indazole. $^1$H NMR (CD$_3$OD, 300 MHz) δ 8.01 (d, J=1.1 Hz, 1H), 7.64 (dd, J=1.6, 0.9 Hz, 1H), 7.49 (dt, J=8.7, 1.0 Hz, 1H), 7.33 (dd, J=7.3, 2.1 Hz, 1H), 7.24 (dd, J=8.7, 1.6 Hz, 1H), 7.21-7.15 (m, 1H), 6.95 (dd, J=9.7, 8.5 Hz, 1H), 4.25 (t, J=7.2 Hz, 2H), 3.07 (t, J=7.3 Hz, 2H), 2.73 (p, J=7.2 Hz, 2H), 2.20 (d, J=1.8 Hz, 3H). MS m/e: 333 (M+H)±.

Compound 3: 6-(2-(4-Fluoro-3-methylphenyl)-5,6-dihydro-4H-pyrrolo[1,2-b]pyrazol-3-yl)-1H-indazole. MS m/e: 333 (M+H)+.

Compound 4: 4-(2-(4-Fluoro-3-methylphenyl)-5,6-dihydro-4H-pyrrolo[1,2-b]pyrazol-3-yl)-1H-pyrrolo[2,3-b]pyridine. $^1$H NMR (CD$_3$OD, 300 MHz) δ 8.27 (d, J=6.0 Hz, 1H), 7.51 (d, J=3.5 Hz, 1H), 7.33 (d, J=6.7 Hz, 1H), 7.28 (d, J=6.1 Hz, 1H), 7.15 (ddd, J=7.8, 5.0, 2.3 Hz, 1H), 6.95 (t, J=9.1 Hz, 1H), 6.35 (d, J=3.8 Hz, 1H), 4.33 (t, J=7.3 Hz, 2H), 3.12 (t, J=7.3 Hz, 2H), 2.77 (p, J=7.3 Hz, 2H), 2.20 (d, J=1.5 Hz, 3H). MS m/e: 333 (M+H)±.

Compound 5: 5-(2-(4-Fluorophenyl)-5,6-dihydro-4H-pyrrolo[1,2-b]pyrazol-3-yl)-1H-indazole. $^1$H NMR (CD$_3$OD, 300 MHz) δ 8.00 (d, J=1.0 Hz, 1H), 7.64 (dd, J=1.6, 0.9 Hz, 1H), 7.49 (dt, J=8.7, 1.0 Hz, 1H), 7.46-7.40 (m, 2H), 7.23 (dd, J=8.7, 1.6 Hz, 1H), 7.08-7.00 (m, 2H), 4.25 (t, J=7.3 Hz, 2H), 3.06 (t, J=7.3 Hz, 2H), 2.72 (p, J=7.3 Hz, 2H). MS m/e: 319 (M+H)±.

Compound 6: 6-(2-(4-Fluorophenyl)-5,6-dihydro-4H-pyrrolo[1,2-b]pyrazol-3-yl)-1H-indazole. $^1$H NMR (CD$_3$OD, 300 MHz) δ 8.02 (d, J=1.0 Hz, 1H), 7.72 (dd, J=8.4, 0.9 Hz, 1H), 7.54-7.42 (m, 1H), 7.35 (d, J=1.3 Hz, 1H), 7.15-7.23 (m, 3H), 4.27 (t, J=7.2 Hz, 2H), 3.11 (t, J=7.3 Hz, 2H), 2.75 (p, J=7.2 Hz, 2H). MS m/e: 319 (M+H)±.

Compound 7: 5-(2-(m-Tolyl)-5,6-dihydro-4H-pyrrolo[1,2-b]pyrazol-3-yl)-1H-indazole. $^1$H NMR (CD$_3$OD, 300 MHz) δ 8.00 (s, 1H), 7.64 (s, 1H), 7.47 (d, J=8.5 Hz, 1H), 7.30 (s, 1H), 7.25 (d, J=8.5 Hz, 1H), 7.21-7.08 (m, 3H), 4.25 (t, J=7.3 Hz, 2H), 3.08 (t, J=7.3 Hz, 2H), 2.73 (p, J=7.2 Hz, 2H), 2.28 (s, 3H). MS m/e: 315 (M+H)±.

Compound 8: 6-(2-(m-Tolyl)-5,6-dihydro-4H-pyrrolo[1,2-b]pyrazol-3-yl)-1H-indazole. $^1$H NMR (CD$_3$OD, 300 MHz) δ 8.02 (d, J=1.1 Hz, 1H), 7.70 (dd, J=8.4, 0.9 Hz, 1H), 7.36 (s, 1H), 7.31 (d, J=2.0 Hz, 1H), 7.22-7.12 (m, 3H), 7.06 (dd, J=8.4, 1.4 Hz, 1H), 4.26 (t, J=7.3 Hz, 2H), 3.11 (d, J=7.2 Hz, 2H), 2.74 (p, J=7.3 Hz, 2H), 2.29 (s, 3H). MS m/e: 315 (M+H)±.

Compound 9: 6-(2-(4-Fluoro-3-methylphenyl)-5,6-dihydro-4H-pyrrolo[1,2-b]pyrazol-3-yl)-1H-benzo[d]imidazole. $^1$H NMR (CD$_3$OD, 300 MHz) δ 9.30 (s, 1H), 7.80 (d, J=8.5 Hz, 1H), 7.61 (s, 1H), 7.53 (d, J=8.5 Hz, 1H), 7.34 (d, J=7.3 Hz, 1H), 7.20 (d, J=6.9 Hz, 1H), 7.00 (m, J=8.9 Hz, 1H), 4.27 (t, J=7.2 Hz, 2H), 3.13 (t, J=7.3 Hz, 2H), 2.76 (p, J=7.3 Hz, 2H), 2.23 (s, 3H). MS m/e: 333 (M+H)$^+$.

Compound 10: 1-Methyl-5-(2-(m-tolyl)-5,6-dihydro-4H-pyrrolo[1,2-b]pyrazol-3-yl)-1H-indazole. $^1$H NMR (CD$_3$OD, 300 MHz) δ 7.94 (s, 1H), 7.62 (s, 1H), 7.47 (d, J=8.5 Hz, 1H), 7.32-7.23 (m, 2H), 7.18-7.10 (m, 3H), 4.25 (t, J=7.2 Hz, 2H), 4.07 (s, 3H), 3.07 (t, J=7.6 Hz, 2H), 2.73 (p, J=7.2 Hz, 2H), 2.27 (s, 3H). MS m/e: 329 (M+H)±.

Compound 11: 1-Methyl-6-(2-(m-tolyl)-5,6-dihydro-4H-pyrrolo[1,2-b]pyrazol-3-yl)-1H-benzo[d]imidazole. $^1$H NMR (CD$_3$OD, 300 MHz) δ 9.34 (d, J=0.7 Hz, 1H), 7.76 (dd, J=8.5, 0.6 Hz, 1H), 7.73 (dd, J=1.5, 0.6 Hz, 1H), 7.50 (dd, J=8.6, 1.5 Hz, 1H), 7.32-7.28 (m, 1H), 7.22-7.13 (m, 3H), 4.28 (t, J=7.2 Hz, 2H), 4.06 (d, J=0.6 Hz, 3H), 3.15 (t, J=7.3 Hz, 2H), 2.77 (p, J=7.3 Hz, 2H), 2.30 (s, 3H). MS m/e: 329 (M+H)±.

Compound 12: 6-(2-(m-Tolyl)-5,6-dihydro-4H-pyrrolo[1,2-b]pyrazol-3-yl)benzo[d]thiazole. $^1$H NMR (CD$_3$OD, 300 MHz) δ 9.20 (s, 1H), 7.97 (d, J=8.5 Hz, 1H), 7.90 (d, J=1.6 Hz, 1H), 7.40 (dd, J=8.5, 1.8 Hz, 1H), 7.29 (s, 1H), 7.23-7.15 (m, 3H), 4.25 (t, J=7.1 Hz, 2H), 3.10 (t, J=7.3 Hz, 2H), 2.73 (p, J=7.4 Hz, 2H), 2.29 (s, 3H). MS m/e: 332 (M+H)±.

Compound 13: 6-(2-(4-Fluorophenyl)-5,6-dihydro-4H-pyrrolo[1,2-b]pyrazol-3-yl)-1-methyl-1H-benzo[d]imidazole. $^1$H NMR (CD$_3$OD, 300 MHz) δ 9.27 (s, 1H), 7.78 (d, J=8.8 Hz, 1H), 7.73 (s, 1H), 7.50-7.40 (m, 3H), 7.08 (t, J=8.8 Hz, 2H), 4.29 (t, J=7.3 Hz, 2H), 4.06 (s, 3H), 3.13 (t, J=7.3 Hz, 2H), 2.77 (p, J=7.4 Hz, 2H). MS m/e: 333 (M+H)±.

Compound 14: 6-(2-(4-Fluorophenyl)-5,6-dihydro-4H-pyrrolo[1,2-b]pyrazol-3-yl)benzo[d]thiazole. MS m/e: 336 (M+H)$^+$.

Compound 15: 5-(2-(4-Fluoro-3-methylphenyl)-5,6-dihydro-4H-pyrrolo[1,2-b]pyrazol-3-yl)-1-methyl-1H-indazole. $^1$H NMR (CD$_3$OD, 300 MHz) δ 7.96 (s, 1H), 7.62 (s, 1H), 7.49 (d, J=8.8 Hz, 1H), 7.33 (dd, J=7.6, 1.5 Hz, 1H), 7.27 (dd, J=8.5, 1.5 Hz, 1H), 7.21-7.16 (m, 1H), 6.94 (t, J=9.1 Hz, 1H), 4.25 (t, J=7.2 Hz, 2H), 4.08 (s, 3H), 3.06 (t, J=7.6 Hz, 2H), 2.73 (p, J=7.2 Hz, 2H), 2.20 (d, J=1.8 Hz, 3H). MS m/e: 347 (M+H)±.

Compound 16: 5-(2-(4-Fluoro-3-methylphenyl)-5,6-dihydro-4H-pyrrolo[1,2-b]pyrazol-3-yl)-1-methyl-1H-benzo[d]imidazole. $^1$H NMR (CD$_3$OD, 300 MHz) δ 9.27 (s, 1H), 7.76 (d, J=8.49 Hz, 1H), 7.73 (d, J=0.6 Hz, 1H), 7.47 (dd, J=8.5, 1.6 Hz, 1H), 7.34 (dd, J=7.6, 2.2 Hz, 1H), 7.19 (ddd, J=7.7, 5.0, 2.3 Hz, 1H), 6.98 (t, J=9.1 Hz, 1H), 4.28 (t, J=7.3 Hz, 2H), 4.07 (s, 3H), 3.14 (t, J=7.3 Hz, 2H), 2.76 (p, J=7.4 Hz, 2H), 2.23 (d, J=1.8 Hz, 3H). MS m/e: 347 (M+H)±.

Compound 17: 6-(2-(4-Fluoro-3-methylphenyl)-5,6-dihydro-4H-pyrrolo[1,2-b]pyrazol-3-yl)benzo[d]thiazole. $^1$H NMR (CD$_3$OD, 300 MHz) δ 9.21 (s, 1H), 7.99 (d, J=8.5 Hz, 1H), 7.92 (d, J=1.7 Hz, 1H), 7.39 (dd, J=8.5, 1.7 Hz, 1H), 7.33 (dd, J=7.4, 2.2 Hz, 1H), 7.20 (ddd, J=7.7, 4.9, 2.3 Hz, 1H), 6.98 (dd, J=9.6, 8.5 Hz, 1H), 4.25 (t, J=7.2 Hz, 2H), 3.10 (t, J=7.3 Hz, 2H), 2.74 (p, J=7.4 Hz, 2H), 2.22 (d, J=1.8 Hz, 3H). MS m/e: 350 (M+H)±.

Compound 18: 6-(2-(m-Tolyl)-5,6-dihydro-4H-pyrrolo[1,2-b]pyrazol-3-yl)imidazo[1,2-a]pyridine. $^1$H NMR (CD$_3$OD, 300 MHz) δ 8.35 (s, 1H), 7.80 (s, 1H), 7.57 (d, J=1.4 Hz, 1H), 7.47 (d, J=9.4 Hz, 1H), 7.33 (s, 1H), 7.26-7.15 (m, 3H), 7.11 (dd, J=9.3, 1.7 Hz, 1H), 4.26 (t, J=7.3 Hz, 2H), 3.10 (t, J=7.3 Hz, 2H), 2.75 (p, J=7.3 Hz, 2H), 2.32 (s, 3H). MS m/e: 315 (M+H)±.

Compound 19: 6-(2-(4-Fluorophenyl)-5,6-dihydro-4H-pyrrolo[1,2-b]pyrazol-3-yl)imidazo[1,2-a]pyridine. $^1$H NMR (CD$_3$OD, 300 MHz) 8.74 (s, 1H), 8.21 (d, J=2.1 Hz, 1H), 8.05 (d, J=2.1 Hz, 1H), 7.87 (d, J=9.5 Hz, 1H), 7.73 (dd, J=9.3, 1.6 Hz, 1H), 7.53-7.46 (m, 2H), 7.17-7.09 (m, 2H), 4.30 (t, J=7.3 Hz, 2H), 3.16 (t, J=7.3 Hz, 2H), 2.78 (p, J=7.3 Hz, 2H). MS m/e: 319 (M+H)±.

Compound 20: 6-(2-(4-Fluoro-3-methylphenyl)-5,6-dihydro-4H-pyrrolo[1,2-b]pyrazol-3-yl)imidazo[1,2-a]pyridine. $^1$H NMR (CD$_3$OD, 300 MHz) 8.74 (s, 1H), 8.21 (d, J=1.8 Hz, 1H), 8.05 (d, J=2.1 Hz, 1H), 7.87 (d, J=9.4 Hz, 1H), 7.72 (dd, J=9.4, 1.6 Hz, 1H), 7.39 (d, J=7.3 Hz, 1H), 7.30-7.18 (m, 1H), 7.04 (t, J=9.1 Hz, 1H), 4.29 (t, J=7.3 Hz, 2H), 3.16 (t, J=7.3 Hz, 2H), 2.78 (p, J=7.4 Hz, 2H), 2.26 (d, J=1.8 Hz, 3H). MS m/e: 333 (M+H)±.

Compound 21: 6-(2-(3-Methoxyphenyl)-5,6-dihydro-4H-pyrrolo[1,2-b]pyrazol-3-yl)imidazo[1,2-a]pyridine. $^1$H NMR (CD$_3$OD, 300 MHz) 8.74 (s, 1H), 8.20 (d, J=2.1 Hz, 1H), 8.05 (d, J=2.1 Hz, 1H), 7.86 (d, J=9.1 Hz, 1H), 7.74 (dd, J=9.4, 1.6 Hz, 1H), 7.28 (t, J=7.9 Hz, 1H), 7.06 (t, J=2.1 Hz, 1H), 7.00-6.93 (m, 2H), 4.30 (t, J=7.4 Hz, 2H), 3.78 (s, 3H), 3.16 (t, J=7.3 Hz, 2H), 2.78 (p, J=7.3 Hz, 2H). MS m/e: 331 (M+H)±.

Compound 22: 5-(2-(3-Chlorophenyl)-5,6-dihydro-4H-pyrrolo[1,2-b]pyrazol-3-yl)-1H-indazole. $^1$H NMR (CD$_3$OD, 300 MHz) δ 8.02 (d, J=0.9 Hz, 1H), 7.66 (dd, J=1.6, 0.9 Hz, 1H), 7.52 (dt, J=8.6, 1.0 Hz, 1H), 7.48-7.46 (m, 1H), 7.35-7.22 (m, 4H), 4.27 (t, J=7.3 Hz, 2H), 3.07 (t, J=7.3 Hz, 2H), 2.74 (p, J=7.4 Hz, 2H). MS m/e: 335 (M+H)±.

Compound 23: 6-(2-(3-Chlorophenyl)-5,6-dihydro-4H-pyrrolo[1,2-b]pyrazol-3-yl)-1H-indazole. $^1$H NMR (CD$_3$OD, 300 MHz) δ 8.04 (d, J=0.9 Hz, 1H), 7.73 (dd, J=8.4, 0.9 Hz, 1H), 7.49 (dd, J=1.8, 1.2 Hz, 1H), 7.37 (q, J=1.1 Hz, 1H), 7.35-7.24 (m, 3H), 7.05 (dd, J=8.4, 1.4 Hz, 1H), 4.26 (t, J=7.2 Hz, 2H), 3.08 (t, J=7.2 Hz, 2H), 2.73 (p, J=7.3 Hz, 2H). MS m/e: 335 (M+H)$^+$.

Compound 24: 6-(2-(3-Chlorophenyl)-5,6-dihydro-4H-pyrrolo[1,2-b]pyrazol-3-yl)-1-methyl-1H-benzo[d]imidazole. $^1$H NMR (CD$_3$OD, 300 MHz) δ 9.30 (s, 1H), 7.83-7.75 (m, 2H), 7.52-7.43 (m, 3H), 7.36-7.31 (m, 2H), 4.29 (t, J=7.3 Hz, 2H), 4.08 (d, J=0.6 Hz, 3H), 3.13 (t, J=7.3 Hz, 2H), 2.77 (p, J=7.4 Hz, 2H). MS m/e: 349 (M+H)±.

Compound 25: 6-(2-(3-Chlorophenyl)-5,6-dihydro-4H-pyrrolo[1,2-b]pyrazol-3-yl)imidazo[1,2-a]pyridine. $^1$H NMR (CD$_3$OD, 300 MHz) 8.77 (dd, J=1.7, 1.0 Hz, 1H), 8.22 (dd, J=2.2, 0.7 Hz, 1H), 8.06 (d, J=2.2 Hz, 1H), 7.89 (dt, J=9.4, 0.9 Hz, 1H), 7.75 (dd, J=9.4, 1.6 Hz, 1H), 7.54 (dt, J=2.3, 0.9 Hz, 2H), 7.39 (dd, J=5.0, 2.9 Hz, 1H), 7.36 (s, 1H), 4.31 (t, J=7.3 Hz, 2H), 3.15 (t, J=7.3 Hz, 2H), 2.78 (p, J=7.4 Hz, 2H). MS m/e: 335 (M+H)±.

Compound 26: 6-(2-(3-Chlorophenyl)-5,6-dihydro-4H-pyrrolo[1,2-b]pyrazol-3-yl)benzo[d]thiazole. $^1$H NMR (CD$_3$OD, 300 MHz) δ 9.23 (s, 1H), 8.03 (d, J=8.5 Hz, 1H), 7.96 (d, J=12 Hz, 1H), 7.49-7.45 (m, 1H), 7.42 (dd, J=8.5, 1.7 Hz, 1H), 7.38-7.25 (m, 3H), 4.28 (t, J=7.3 Hz, 2H), 3.11 (t, J=7.3 Hz, 2H), 2.75 (p, J=7.4 Hz, 2H). MS m/e: 352 (M+H)±.

Compound 27: 5-(2-(3-Methoxyphenyl)-5,6-dihydro-4H-pyrrolo[1,2-b]pyrazol-3-yl)-1H-indazole. $^1$H NMR (CD$_3$OD, 300 MHz) δ 8.00 (s, 1H), 7.66 (s, 1H), 7.49 (d, J=8.5 Hz, 1H), 7.26 (dd, J=8.7, 1.5 Hz, 1H), 7.20 (t, J=8.1 Hz, 1H), 7.03-6.98 (m, 2H), 6.86 (ddd, J=8.3, 2.6, 1.1 Hz, 1H), 4.25 (t, J=7.2 Hz, 2H), 3.65 (s, 3H), 3.06 (t, J=7.3 Hz, 2H), 2.72 (p, J=7.3 Hz, 2H). MS m/e: 331 (M+H)±.

Compound 28: 6-(2-(3-Methoxyphenyl)-5,6-dihydro-4H-pyrrolo[1,2-b]pyrazol-3-yl)-1H-indazole. $^1$H NMR (CD$_3$OD, 300 MHz) δ 8.02 (d, J=0.9 Hz, 1H), 7.71 (dd, J=8.5, 0.9 Hz, 1H), 7.38 (d, J=0.9 Hz, 1H), 7.22 (t, J=8.1 Hz, 1H), 7.07 (dd, J=8.4, 1.4 Hz, 1H), 7.04-6.99 (m, 2H), 6.88 (ddd, J=8.3, 2.6, 1.1 Hz, 1H), 4.26 (t, J=7.3 Hz, 2H), 3.67 (s, 3H), 3.10 (t, J=7.3 Hz, 2H), 2.74 (p, J=7.3 Hz, 2H). MS m/e: 331 (M+H)±.

Compound 29: 6-(2-(3-Methoxyphenyl)-5,6-dihydro-4H-pyrrolo[1,2-b]pyrazol-3-yl)-1-methyl-1H-benzo[d]imidazole. $^1$H NMR (CD$_3$OD, 300 MHz) δ 9.27 (s, 1H), 7.76 (dd, J=8.6, 0.7 Hz, 1H), 7.74 (dd, J=1.5, 0.7 Hz, 1H), 7.50 (dd, J=8.6, 1.5 Hz, 1H), 7.24 (t, J=7.91 Hz, 1H), 7.01 (dd, J=2.3, 1.5 Hz, 1H), 6.97 (ddd, J=7.6, 1.6, 1.0 Hz, 1H), 6.92 (ddd, J=8.3, 2.6, 1.0 Hz, 1H), 4.29 (t, J=7.3 Hz, 2H), 4.06 (d, J=0.5 Hz, 3H), 3.73 (s, 3H), 3.14 (t, J=7.3 Hz, 2H), 2.77 (p, J=7.3 Hz, 2H). MS m/e: 345 (M+H)±.

Compound 30: 6-(2-(3-Methoxyphenyl)-5,6-dihydro-4H-pyrrolo[1,2-b]pyrazol-3-yl)benzo[d]thiazole. MS m/e: 348 (M+H)±.

Compound 31: 5-(2-(3-Trifluoromethylphenyl)-5,6-dihydro-4H-pyrrolo[1,2-b]pyrazol-3-yl)-1H-indazole. $^1$H NMR (CD$_3$OD, 300 MHz) δ 8.02 (s, 1H), 7.77 (s, 1H), 7.67 (dd, J=1.5, 0.9 Hz, 2H), 7.64 (s, 1H), 7.58 (d, J=7.9 Hz, 1H), 7.52 (d, J=8.5 Hz, 1H), 7.46 (d, J=7.8 Hz, 1H), 7.25 (dd, J=8.6, 1.6 Hz, 1H), 4.28 (t, J=7.3 Hz, 2H), 3.07 (t, J=7.3 Hz, 2H), 2.74 (p, J=7.3 Hz, 2H). MS m/e: 369 (M+H)±.

Compound 32: 6-(2-(3-Trifluoromethylphenyl)-5,6-dihydro-4H-pyrrolo[1,2-b]pyrazol-3-yl)-1H-indazole. $^1$H NMR (CD$_3$OD, 300 MHz) δ 8.05 (d, J=0.9 Hz, 1H), 7.79 (s, 1H), 7.75 (dd, J=8.4, 0.9 Hz, 1H), 7.69-7.63 (m, 1H), 7.63-7.57 (m, 1H), 7.49 (t, J=7.8 Hz, 1H), 7.38 (d, J=0.9 Hz, 1H), 7.06 (dd, J=8.4, 1.4 Hz, 1H), 4.29 (t, J=7.3 Hz, 2H), 3.11 (t, J=7.3 Hz, 2H), 2.76 (p, J=7.3 Hz, 2H). MS m/e: 369 (M+H)±.

Compound 33: 1-Methyl-6-(2-(3-trifluoromethylphenyl)-5,6-dihydro-4H-pyrrolo[1,2-b]pyrazol-3-yl)-1H-benzo[d]imidazole. $^1$H NMR (CD$_3$OD, 300 MHz) δ 9.31 (s, 1H), 7.81 (dd, J=5.3, 0.6 Hz, 1H), 7.79 (dd, J=2.1, 0.9 Hz, 1H), 7.76-7.74 (m, 1H), 7.70-7.62 (m, 2H), 7.53 (d, J=7.6 Hz, 1H), 7.48 (dd, J=8.7, 1.4 Hz, 1H), 4.31 (t, J=7.2 Hz, 2H), 4.08 (d, J=0.6 Hz, 3H), 3.14 (t, J=7.2 Hz, 2H), 2.78 (p, J=7.3 Hz, 2H). MS m/e: 383 (M+H)±.

Compound 34: 6-(2-(3-Trifluoromethylphenyl)-5,6-dihydro-4H-pyrrolo[1,2-b]pyrazol-3-yl)imidazo[1,2-a]pyridine. MS m/e: 369 (M+H)$^+$.

Compound 35: 6-(2-(3-Trifluoromethylphenyl)-5,6-dihydro-4H-pyrrolo[1,2-b]pyrazol-3-yl)benzo[d]thiazole. $^1$H NMR (CD$_3$OD, 300 MHz) δ 9.24 (s, 1H), 8.03 (dd, J=8.5, 0.6 Hz, 1H), 7.97 (dd, J=1.7, 0.6 Hz, 1H), 7.76 (s, 1H), 7.70-7.58 (m, 2H), 7.51 (t, J=7.6 Hz, 1H), 7.43 (dd, J=8.5, 1.7 Hz, 1H), 4.30 (t, J=7.3 Hz, 2H), 3.12 (t, J=7.5 Hz, 2H), 2.77 (p, J=7.3 Hz, 2H). MS m/e: 386 (M+H)$^+$.

Compound 36: 7-(1H-Indazol-5-yl)-6-(m-tolyl)-2,3-dihydropyrazolo[5,1-b]oxazole. MS m/e: 317 (M+H)±.

Compound 37: 7-(1H-Indazol-6-yl)-6-(m-tolyl)-2,3-dihydropyrazolo[5,1-b]oxazole. $^1$H NMR (CD$_3$OD, 300 MHz) δ 7.99 (s, 1H), 7.56-7.54 (m, 1H), 7.37-7.35 (m, 1H), 7.34-7.32 (m, 1H), 7.26-7.18 (m, 3H), 7.08 (dd, J=8.5, 1.4 Hz, 1H), 5.24 (t, J=8.0 Hz, 2H), 4.43 (dd, J=8.6, 7.5 Hz, 2H), 2.32 (s, 3H). MS m/e: 317 (M+H)±.

Compound 38: 7-(1-Methyl-1H-benzo[d]imidazol-6-yl)-6-(m-tolyl)-2,3-dihydropyrazolo[5,1-b]oxazole. $^1$H NMR (CD$_3$OD, 300 MHz) δ 9.18 (s, 1H), 7.70 (dd, J=8.7, 0.7 Hz, 1H), 7.65 (dd, J=1.6, 0.7 Hz, 1H), 7.49 (dd, J=8.7, 1.6 Hz, 1H), 7.35-7.20 (m, 4H), 5.29 (t, J=8.1 Hz, 2H), 4.47 (dd, J=8.8, 7.3 Hz, 2H), 4.00 (d, J=0.6 Hz, 3H), 2.34 (d, J=0.6 Hz, 3H). MS m/e: 331 (M+H)±.

Compound 39: 7-(Benzo[d]thiazol-6-yl)-6-(m-tolyl)-2,3-dihydropyrazolo[5,1-b]oxazole. $^1$H NMR (CD$_3$OD, 300 MHz) δ 9.18 (s, 1H), 7.94 (dd, J=8.6, 0.6 Hz, 1H), 7.89 (dd, J=1.8, 0.6 Hz, 1H), 7.42 (dd, J=8.6, 1.7 Hz, 1H), 7.34-7.30 (m, 1H), 7.28-7.20 (m, 3H), 5.27 (dd, J=8.5, 7.3 Hz, 2H), 4.45 (dd, J=8.7, 7.3 Hz, 2H), 2.33 (s, 3H). MS m/e: 334 (M+H)±.

Compound 40: 3-(1H-Indazol-5-yl)-2-(m-tolyl)-6,7-dihydro-5H-pyrazolo[5,1-b][1,3]oxazine. $^1$H NMR (CD$_3$OD, 300 MHz) δ 7.97 (d, J=0.9 Hz, 1H), 7.64 (t, J=1.0 Hz, 1H), 7.43 (d, J=8.8 Hz, 1H), 7.29 (s, 1H), 7.24 (dd, J=8.6, 1.5 Hz, 1H), 7.20-7.12 (m, 3H), 4.44 (t, J=5.1 Hz, 2H), 4.27 (t, J=6.3 Hz, 2H), 2.40 (p, J=6.0 Hz, 2H), 2.28 (s, 3H). MS m/e: 331 (M+H)±.

Compound 41: 3-(1-Methyl-1H-benzo[c]imidazol-6-yl)-2-(m-tolyl)-6,7-dihydro-5H-pyrazolo[5,1-b][1,3]oxazine. $^1$H NMR (CD$_3$OD, 300 MHz) δ 9.24 (s, 1H), 7.72 (dd, J=1.5, 0.6 Hz, 1H), 7.69 (dd, J=8.7, 0.7 Hz, 1H), 7.47 (dd, J=8.7, 1.5 Hz, 1H), 7.29 (m, 1H), 7.23-7.14 (m, 3H), 4.49 (dd, J=5.9, 4.7 Hz, 2H), 4.29 (t, J=6.2 Hz, 2H), 4.03 (s, 3H), 2.47-2.36 (m, 2H), 2.31 (s, 3H). MS m/e: 345 (M+H)±.

Compound 42: 3-(Imidazo[1,2-a]pyridin-6-yl)-2-(m-tolyl)-6,7-dihydro-5H-pyrazolo[5,1-b][1,3]oxazine. MS m/e: 331 (M+H)±.

Compound 43: 3-(benzo[d]thiazol-6-yl)-2-(m-tolyl)-6,7-dihydro-5H-pyrazolo[5,1-b][1,3]oxazine. MS m/e: 348 (M+H)±.

Compound 44: 7-(imidazo[1,2-a]pyridin-6-yl)-6-(m-tolyl)-2,3-dihydropyrazolo[5,1-b]oxazole. MS m/e: 317 (M+H)±.

Compound 45: 6-(2-(4-Fluorophenyl)-5,6-dihydro-4H-pyrrolo[1,2-b]pyrazol-3-yl)quinoline. $^1$H NMR (CD$_3$OD, 300 MHz) δ 9.08 (dd, J=5.2, 1.5 Hz, 1H), 8.91 (d, J=8.2 Hz, 1H), 8.13 (d, J=8.8 Hz, 1H), 8.10 (d, J=2.1 Hz, 1H), 7.95 (dd, J=8.4, 5.2 Hz, 1H), 7.90 (dd, J=8.9, 2.0 Hz, 1H), 7.50-7.42 (m, 2H), 7.15-7.06 (m, 2H), 4.30 (t, J=7.3 Hz, 2H), 3.20 (t, J=7.3 Hz, 2H), 2.78 (p, J=7.3 Hz, 2H). MS m/e: 330 (M+H)±.

Compound 46: 6-(2-(m-Tolyl)-5,6-dihydro-4H-pyrrolo[1,2-b]pyrazol-3-yl)quinoline. $^1$H NMR (CD$_3$OD, 300 MHz) δ 9.09 (dd, J=5.3, 1.5 Hz, 1H), 8.96 (dd, J=8.2, 1.5 Hz, 1H), 8.13 (s, 1H), 8.11 (d, J=7.3 Hz, 1H), 7.98 (dd, J=8.4, 5.3 Hz, 1H), 7.92 (dd, J=8.9, 1.9 Hz, 1H), 7.32-7.29 (m, 1H), 7.27-7.16 (m, 3H), 4.30 (t, J=7.3 Hz, 2H), 3.21 (t, J=7.3 Hz, 2H), 2.79 (p, J=7.3 Hz, 2H), 2.31 (s, 3H). MS m/e: 326 (M+H)±.

Compound 47: 6-(2-(4-Fluoro-3-methylphenyl)-5,6-dihydro-4H-pyrrolo[1,2-b]pyrazol-3-yl)quinoline. $^1$H NMR (CD$_3$OD, 300 MHz) δ 9.08 (dd, J=5.2, 1.5 Hz, 1H), 8.91 (d, J=8.2 Hz, 1H), 8.12 (d, J=8.8 Hz, 1H), 8.09 (d, J=1.8 Hz, 1H), 7.95 (dd, J=8.4, 5.2 Hz, 1H), 7.89 (dd, J=8.9, 1.9 Hz, 1H), 7.36 (dd, J=7.5, 1.6 Hz, 1H), 7.25-7.18 (m, 1H), 7.01 (t, J=8.9 Hz, 1H), 4.29 (t, J=7.3 Hz, 2H), 3.19 (t, J=7.3 Hz, 2H), 2.78 (p, J=7.3 Hz, 2H), 2.23 (d, J=1.8 Hz, 3H). MS m/e: 344 (M+H)±.

Compound 48: 6-(2-(3-Methoxyphenyl)-5,6-dihydro-4H-pyrrolo[1,2-b]pyrazol-3-yl)quinoline. $^1$H NMR (CD$_3$OD, 300 MHz) δ 8.80 (dd, J=4.4, 1.7 Hz, 1H), 8.24 (dd, J=8.5, 0.9 Hz, 1H), 7.93 (d, J=8.8 Hz, 1H), 7.79 (d, J=2.1 Hz, 1H), 7.61 (dd, J=8.8, 2.0 Hz, 1H), 7.51 (dd, J=8.3, 4.3 Hz, 1H), 7.22 (t, J=7.8 Hz, 1H), 7.04-6.97 (m, 2H), 6.90 (ddd, J=8.2, 2.6, 1.0 Hz, 1H), 4.26 (t, J=7.2 Hz, 2H), 3.68 (s, 3H), 3.11 (t, J=7.2 Hz, 2H), 2.73 (p, J=7.3 Hz, 2H). MS m/e: 342 (M+H)±.

Compound 49: 6-(2-(3-Chlorophenyl)-5,6-dihydro-4H-pyrrolo[1,2-b]pyrazol-3-yl)quinoline. $^1$H NMR (CD$_3$OD, 300 MHz) δ 8.84 (dd, J=4.4, 1.7 Hz, 1H), 8.30 (d, J=8.2 Hz, 1H), 7.99 (d, J=8.8 Hz, 1H), 7.84 (d, J=2.1 Hz, 1H), 7.64 (dd, J=8.8, 2.0 Hz, 1H), 7.55 (dd, J=8.3, 4.3 Hz, 1H), 7.50 (td, J=1.8, 0.6 Hz, 1H), 7.40-7.28 (m, 3H), 4.30 (t, J=7.3 Hz, 2H), 3.16 (t, J=7.3 Hz, 2H), 2.77 (p, J=7.3 Hz, 2H). MS m/e: 346 (M+H)±.

Compound 50: 6-(2-(3-Trifluoromethylphenyl)-5,6-dihydro-4H-pyrrolo[1,2-b]pyrazol-3-yl)quinoline. $^1$H NMR (CD$_3$OD, 300 MHz) δ 9.09 (d, J=4.7 Hz, 1H), 8.90 (d, J=7.9 Hz, 1H), 8.15 (d, J=8.8 Hz, 1H), 8.13 (d, J=1.8 Hz, 1H), 7.96 (dd, J=8.4, 5.1 Hz, 1H), 7.92 (dd, J=8.8, 2.1 Hz, 1H), 7.79 (d, J=0.6 Hz, 1H), 7.72-7.65 (m, 2H), 7.55 (t, J=7.8 Hz, 1H), 4.33 (t, J=7.3 Hz, 2H), 3.21 (t, J=7.3 Hz, 2H), 2.80 (p, J=7.3 Hz, 2H). MS m/e: 380 (M+H)±.

Compound 51: 7-(Quinolin-6-yl)-6-(m-tolyl)-2,3-dihydropyrazolo[5,1-b]oxazole. MS m/e: 328 (M+H)±.

Compound 52: 7-(Quinoxalin-6-yl)-6-(m-tolyl)-2,3-dihydropyrazolo[5,1-b]oxazole. $^1$H NMR (CD$_3$OD, 300 MHz) δ 8.80 (s, 2H), 7.95 (dd, J=8.8, 0.6 Hz, 1H), 7.92 (d, J=1.8 Hz, 1H), 7.75 (dd, J=8.8, 2.0 Hz, 1H), 7.66 (d, J=11.1 Hz, 1H), 7.35 (s, 1H), 7.30-7.26 (m, 2H), 5.32 (dd, J=8.8, 7.6 Hz, 2H), 4.48 (dd, J=8.6, 7.5 Hz, 2H), 2.35 (s, 3H). MS m/e: 329 (M+H)±.

Compound 53: 6-(2-(4-Fluorophenyl)-5,6-dihydro-4H-pyrrolo[1,2-b]pyrazol-3-yl)quinoxaline. $^1$H NMR (CD$_3$OD, 300 MHz) δ 8.85 (s, 2H), 8.03 (d, J=8.8 Hz, 1H), 7.93 (d, J=1.5 Hz, 1H), 7.72 (dd, J=8.8, 2.0 Hz, 1H), 7.53-7.43 (m, 2H), 7.16-7.08 (m, 2H), 4.30 (t, J=7.3 Hz, 2H), 3.20 (t, J=7.3 Hz, 2H), 2.78 (p, J=7.3 Hz, 2H). MS m/e: 331 (M+H)±.

Compound 54: 6-(2-(m-Tolyl)-5,6-dihydro-4H-pyrrolo[1,2-b]pyrazol-3-yl)quinoxaline. $^1$H NMR (CD$_3$OD, 300 MHz) δ 8.83 (s, 2H), 7.97 (dd, J=8.8, 0.6 Hz, 1H), 7.93 (dd, J=2.0, 0.6 Hz, 1H), 7.69 (dd, J=8.8, 2.0 Hz, 1H), 7.33-7.30 (m, 1H), 7.25-7.17 (m, 3H), 4.28 (t, J=7.2 Hz, 2H), 3.18 (t, J=7.3 Hz, 2H), 2.77 (p, J=7.4 Hz, 2H), 2.31 (s, 3H). MS m/e: 327 (M+H)±.

Compound 55: 6-(2-(4-Fluoro-3-methylphenyl)-5,6-dihydro-4H-pyrrolo[1,2-b]pyrazol-3-yl)quinoxaline. $^1$H NMR (CD$_3$OD, 300 MHz) δ 8.84 (s, 2H), 8.00 (dd, J=8.8, 0.6 Hz, 1H), 7.91 (d, J=2.1 Hz, 1H), 7.70 (dd, J=8.8, 2.0 Hz, 1H), 7.36 (dd, J=7.3, 1.5 Hz, 1H), 7.27-7.17 (m, 1H), 7.01 (dd, J=9.7, 8.5 Hz, 1H), 4.28 (t, J=7.3 Hz, 2H), 3.18 (t, J=7.3 Hz, 2H), 2.77 (p, J=7.40 Hz, 2H), 2.23 (d, J=1.8 Hz, 3H). MS m/e: 345 (M+H)±.

Compound 56: 6-(2-(3-Methoxyphenyl)-5,6-dihydro-4H-pyrrolo[1,2-b]pyrazol-3-yl)quinoxaline. $^1$H NMR (CD$_3$OD, 300 MHz) δ 8.84 (s, 2H), 8.00 (d, J=8.8 Hz, 1H), 7.95 (d, J=2.1 Hz, 1H), 7.72 (dd, J=8.8, 2.0 Hz, 1H), 7.26 (t, J=7.9 Hz, 1H), 7.06-6.97 (m, 2H), 6.94 (ddd, J=8.3, 2.6, 1.0 Hz, 1H), 4.29 (t, J=7.2 Hz, 2H), 3.71 (s, 3H), 3.18 (t, J=7.3 Hz, 2H), 2.77 (p, J=8.2, 6.6 Hz, 2H). MS m/e: 343 (M+H)±.

Compound 57: 6-(2-(3-Chlorophenyl)-5,6-dihydro-4H-pyrrolo[1,2-b]pyrazol-3-yl)quinoxaline. MS m/e: 347 (M+H)±.

Compound 58: 6-(2-(3-Trifluoromethylphenyl)-5,6-dihydro-4H-pyrrolo[1,2-b]pyrazol-3-yl)quinoxaline. MS m/e: 381 (M+H)±.

Compound 59: 7-(1H-Indazol-5-yl)-6-(3-trifluoromethylphenyl)-2,3-dihydropyrazolo[5,1-b]oxazole. MS m/e: 371 (M+H)±.

Compound 60: 7-(1-Methyl-1H-benzo[d]imidazol-6-yl)-6-(3-trifluoromethylphenyl)-2,3-dihydropyrazolo[5,1-b]oxazole. MS m/e: 385 (M+H)±.

Compound 61: 7-(Imidazo[1,2-c]pyridin-6-yl)-6-(3-trifluoromethylphenyl)-2,3-dihydropyrazolo[5,1-b]oxazole. MS m/e: 371 (M+H)±.

Compound 62: 7-(Benzo[d]thiazol-6-yl)-6-(3-trifluoromethylphenyl)-2,3-dihydropyrazolo[5,1-b]oxazole. MS m/e: 388 (M+H)±.

Compound 63: 7-(Quinolin-6-yl)-6-(3-trifluoromethylphenyl)-2,3-dihydropyrazolo[5,1-b]oxazole. MS m/e: 382 (M+H)±.

Compound 64: 7-(Quinoxalin-6-yl)-6-(3-trifluoromethylphenyl)-2,3-dihydropyrazolo[5,1-b]oxazole. MS m/e: 383 (M+H)±.

Compound 65: 6-(4-Fluorophenyl)-7-(1H-indazol-6-yl)-2,3-dihydropyrazolo[5,1-b]oxazole. MS m/e: 321 (M+H)±.

Compound 66: 6-(4-Fluorophenyl)-7-(1-methyl-1H-benzo[d]imidazol-6-yl)-2,3-dihydropyrazolo[5,1-b]oxazole. MS m/e: 335 (M+H)±.

Compound 67: 6-(4-Fluorophenyl)-7-(imidazo[1,2-a]pyridin-6-yl)-2,3-dihydropyrazolo[5,1-b]oxazole. MS m/e: 321 (M+H)±.

Compound 68: 7-(Benzo[d]thiazol-6-yl)-6-(4-fluorophenyl)-2,3-dihydropyrazolo[5,1-b]oxazole. MS m/e: 338 (M+H)±.

Compound 69: 6-(4-Fluorophenyl)-7-(quinolin-6-yl)-2,3-dihydropyrazolo[5,1-b]oxazole. MS m/e: 332 (M+H)±.

Compound 70: 6-(4-Fluorophenyl)-7-(quinoxalin-6-yl)-2,3-dihydropyrazolo[5,1-b]oxazole. MS m/e: 333 (M+H)$^+$.

Compound 71: 7-(1H-Indazol-6-yl)-6-(3-trifluoromethylphenyl)-2,3-dihydropyrazolo[5,1-b]oxazole. MS m/e: 371 (M+H)±.

Compound 72: 6-(3-Methoxyphenyl)-7-(1-methyl-1H-benzo[d]imidazol-6-yl)-2,3-dihydropyrazolo[5,1-b]oxazole. MS m/e: 347 (M+H)±.

Compound 73: 7-(Imidazo[1,2-a]pyridin-6-yl)-6-(3-methoxyphenyl)-2,3-dihydropyrazolo[5,1-b]oxazole. MS m/e: 333 (M+H)±.

Compound 74: 7-(Benzo[d]thiazol-6-yl)-6-(3-methoxyphenyl)-2,3-dihydropyrazolo[5,1-b]oxazole. MS m/e: 350 (M+H)±.

Compound 75: 6-(3-Methoxyphenyl)-7-(quinolin-6-yl)-2,3-dihydropyrazolo[5,1-b]oxazole. MS m/e: 344 (M+H)±.

Compound 76: 6-(3-Methoxyphenyl)-7-(quinoxalin-6-yl)-2,3-dihydropyrazolo[5,1-b]oxazole. MS m/e: 345 (M+H)±.

Compound 77: 5-(2-(3-Fluorophenyl)-5,6-dihydro-4H-pyrrolo[1,2-b]pyrazol-3-yl)-1H-indazole. MS m/e: 319 (M+H)±.

Compound 78: 6-(2-(3-Fluorophenyl)-5,6-dihydro-4H-pyrrolo[1,2-b]pyrazol-3-yl)-1H-indazole. MS m/e: 319 (M+H)±.

Compound 79: 6-(2-(3-Fluorophenyl)-5,6-dihydro-4H-pyrrolo[1,2-b]pyrazol-3-yl)-1-methyl-1H-benzo[d]imidazole. MS m/e: 333 (M+H)$^+$.

Compound 80: 6-(2-(3-Fluorophenyl)-5,6-dihydro-4H-pyrrolo[1,2-b]pyrazol-3-yl)imidazo[1,2-a]pyridine. MS m/e: 319 (M+H)±.

Compound 81: 6-(2-(3-Fluorophenyl)-5,6-dihydro-4H-pyrrolo[1,2-b]pyrazol-3-yl)benzo[d]thiazole. MS m/e: 336 (M+H)⁺.

Compound 82: 6-(2-(3-Fluorophenyl)-5,6-dihydro-4H-pyrrolo[1,2-b]pyrazol-3-yl)quinoxaline. MS m/e: 331 (M+H)±.

Compound 83: 5-(2-(3,4-Difluorophenyl)-5,6-dihydro-4H-pyrrolo[1,2-b]pyrazol-3-yl)-1H-indazole. MS m/e: 337 (M+H)±.

Compound 84: 6-(2-(3,4-Difluorophenyl)-5,6-dihydro-4H-pyrrolo[1,2-b]pyrazol-3-yl)-1H-indazole. MS m/e: 337 (M+H)±.

Compound 85: 6-(2-(3,4-Difluorophenyl)-5,6-dihydro-4H-pyrrolo[1,2-b]pyrazol-3-yl)-1-methyl-1H-benzo[d]imidazole. MS m/e: 351 (M+H)±.

Compound 86: 6-(2-(3,4-Difluorophenyl)-5,6-dihydro-4H-pyrrolo[1,2-b]pyrazol-3-yl)imidazo[1,2-a]pyridine. MS m/e: 337 (M+H)±.

Compound 87: 6-(2-(3,4-Difluorophenyl)-5,6-dihydro-4H-pyrrolo[1,2-b]pyrazol-3-yl)benzo[d]thiazole. MS m/e: 354 (M+H)±.

Compound 88: 6-(2-(3,4-Difluorophenyl)-5,6-dihydro-4H-pyrrolo[1,2-b]pyrazol-3-yl)quinoline. MS m/e: 348 (M+H)±.

Compound 89: 6-(2-(3,4-Difluorophenyl)-5,6-dihydro-4H-pyrrolo[1,2-b]pyrazol-3-yl)quinoxaline. MS m/e: 349 (M+H)±.

Compound 90: 5-(2-(Benzo[d][1,3]dioxol-5-yl)-5,6-dihydro-4H-pyrrolo[1,2-b]pyrazol-3-yl)-1H-indazole. MS m/e: 345 (M+H)±.

Compound 91: 5-(2-(2,4-Difluorophenyl)-5,6-dihydro-4H-pyrrolo[1,2-b]pyrazol-3-yl)-1H-indazole. MS m/e: 337 (M+H)±.

Compound 92: 6-(2-(2,4-Difluorophenyl)-5,6-dihydro-4H-pyrrolo[1,2-b]pyrazol-3-yl)-1H-indazole. MS m/e: 337 (M+H)±.

Compound 93: 6-(2-(2,4-Difluorophenyl)-5,6-dihydro-4H-pyrrolo[1,2-b]pyrazol-3-yl)-1-methyl-1H-benzo[d]imidazole. MS m/e: 351 (M+H)±.

Compound 94: 6-(2-(2,4-Difluorophenyl)-5,6-dihydro-4H-pyrrolo[1,2-b]pyrazol-3-yl)imidazo[1,2-a]pyridine. MS m/e: 337 (M+H)±.

Compound 95: 6-(2-(2,4-Difluorophenyl)-5,6-dihydro-4H-pyrrolo[1,2-b]pyrazol-3-yl)quinoline. MS m/e: 348 (M+H)±.

Compound 96: 6-(2-(2,4-Difluorophenyl)-5,6-dihydro-4H-pyrrolo[1,2-b]pyrazol-3-yl)quinoxaline. MS m/e: 349 (M+H)±.

Compound 97: 6-(2-(2,4-Difluorophenyl)-5,6-dihydro-4H-pyrrolo[1,2-b]pyrazol-3-yl)benzo[d]thiazole. MS m/e: 354 (M+H)±.

Compound 98: 5-(2-(4-Methoxyphenyl)-5,6-dihydro-4H-pyrrolo[1,2-b]pyrazol-3-yl)-1H-indazole. MS m/e: 331 (M+H)±.

Compound 99: 6-(2-(4-Methoxyphenyl)-5,6-dihydro-4H-pyrrolo[1,2-b]pyrazol-3-yl)-1H-indazole. MS m/e: 331 (M+H)±.

Compound 100: 6-(2-(4-Methoxyphenyl)-5,6-dihydro-4H-pyrrolo[1,2-b]pyrazol-3-yl)benzo[d]thiazole. MS m/e: 348 (M+H)±.

Compound 101: 6-(2-(4-Methoxyphenyl)-5,6-dihydro-4H-pyrrolo[1,2-b]pyrazol-3-yl)quinoline. MS m/e: 342 (M+H)±.

Compound 102: 6-(2-(4-Methoxyphenyl)-5,6-dihydro-4H-pyrrolo[1,2-b]pyrazol-3-yl)quinoxaline. MS m/e: 343 (M+H)±.

Compound 103: 6-(2-(4-Fluorophenyl)-5,6-dihydro-4H-pyrrolo[1,2-b]pyrazol-3-yl)-[1,2,4]triazolo[1,5-a]pyridine. MS m/e: 320 (M+H)±.

Compound 104: 6-(2-(m-Tolyl)-5,6-dihydro-4H-pyrrolo[1,2-b]pyrazol-3-yl)-[1,2,4]triazolo[1,5-a]pyridine. MS m/e: 316 (M+H)±.

Compound 105: 6-(2-(4-Fluoro-3-methylphenyl)-5,6-dihydro-4H-pyrrolo[1,2-b]pyrazol-3-yl)-[1,2,4]triazolo[1,5-a]pyridine. MS m/e: 334 (M+H)±.

Compound 106: 6-(2-(3-Methoxyphenyl)-5,6-dihydro-4H-pyrrolo[1,2-b]pyrazol-3-yl)-[1,2,4]triazolo[1,5-a]pyridine. MS m/e: 332 (M+H)±.

Compound 107: 6-(2-(3-Chlorophenyl)-5,6-dihydro-4H-pyrrolo[1,2-b]pyrazol-3-yl)-[1,2,4]triazolo[1,5-a]pyridine. MS m/e: 336 (M+H)⁺.

Compound 108: 6-(2-(3-Trifluoromethylphenyl)-5,6-dihydro-4H-pyrrolo[1,2-b]pyrazol-3-yl)-[1,2,4]triazolo[1,5-a]pyridine. MS m/e: 370 (M+H)±.

Compound 109: 6-(2-(3-Fluorophenyl)-5,6-dihydro-4H-pyrrolo[1,2-b]pyrazol-3-yl)-[1,2,4]triazolo[1,5-a]pyridine. MS m/e: 320 (M+H)±.

Compound 110: 6-(2-(3,4-Difluorophenyl)-5,6-dihydro-4H-pyrrolo[1,2-b]pyrazol-3-yl)-[1,2,4]triazolo[1,5-a]pyridine. MS m/e: 338 (M+H)±.

Compound 111: 6-(2-(2,4-Difluorophenyl)-5,6-dihydro-4H-pyrrolo[1,2-b]pyrazol-3-yl)-[1,2,4]triazolo[1,5-a]pyridine. MS m/e: 338 (M+H)⁺.

Compound 112: 5-(2-(2,4,5-Trifluorophenyl)-5,6-dihydro-4H-pyrrolo[1,2-b]pyrazol-3-yl)-1H-indazole. MS m/e: 355 (M+H)⁺.

Compound 113: 6-(2-(2,4,5-Trifluorophenyl)-5,6-dihydro-4H-pyrrolo[1,2-b]pyrazol-3-yl)-1H-indazole. MS m/e: 355 (M+H)⁺.

Compound 114: 1-Methyl-6-(2-(2,4,5-trifluorophenyl)-5,6-dihydro-4H-pyrrolo[1,2-b]pyrazol-3-yl)-1H-benzo[d]imidazole. MS m/e: 369 (M+H)⁺.

Compound 115: 6-(2-(2,4,5-Trifluorophenyl)-5,6-dihydro-4H-pyrrolo[1,2-b]pyrazol-3-yl)imidazo[1,2-a]pyridine. MS m/e: 355 (M+H)⁺.

Compound 116: 6-(2-(2,4,5-Trifluorophenyl)-5,6-dihydro-4H-pyrrolo[1,2-b]pyrazol-3-yl)benzo[d]thiazole. MS m/e: 372 (M+H)±.

Compound 117: 6-(2-(2,4,5-Trifluorophenyl)-5,6-dihydro-4H-pyrrolo[1,2-b]pyrazol-3-yl)quinoline. MS m/e: 366 (M+H)⁺.

Compound 118: 6-(2-(2,4,5-Trifluorophenyl)-5,6-dihydro-4H-pyrrolo[1,2-b]pyrazol-3-yl)quinoxaline. MS m/e: 367 (M+H)±.

Compound 119: 6-(2-(2,4,5-Trifluorophenyl)-5,6-dihydro-4H-pyrrolo[1,2-b]pyrazol-3-yl)-[1,2,4]triazolo[1,5-a]pyridine. MS m/e: 356 (M+H)⁺.

Compound 120: 6-(2-(2-Chlorophenyl)-5,6-dihydro-4H-pyrrolo[1,2-b]pyrazol-3-yl)benzo[d]thiazole. MS m/e: 352 (M+H)±.

Compound 121: 6-(2-(2-Chlorophenyl)-5,6-dihydro-4H-pyrrolo[1,2-b]pyrazol-3-yl)-[1,2,4]triazolo[1,5-a]pyridine. MS m/e: 336 (M+H)⁺.

Compound 122: 5-(2-(3-Trifluoromethoxyphenyl)-5,6-dihydro-4H-pyrrolo[1,2-b]pyrazol-3-yl)-1H-indazole. MS m/e: 385 (M+H)⁺.

Compound 123: 6-(2-(3-Trifluoromethoxyphenyl)-5,6-dihydro-4H-pyrrolo[1,2-b]pyrazol-3-yl)-1H-indazole. MS m/e: 385 (M+H)⁺.

Compound 124: 6-(2-(3-Trifluoromethoxyphenyl)-5,6-dihydro-4H-pyrrolo[1,2-b]pyrazol-3-yl)imidazo[1,2-a]pyridine. MS m/e: 385 (M+H)⁺.

Compound 125: 6-(2-(3-Trifluoromethoxyphenyl)-5,6-dihydro-4H-pyrrolo[1,2-b]pyrazol-3-yl)benzo[d]thiazole. MS m/e: 402 (M+H)±.

Compound 126: 6-(2-(3-Trifluoromethoxyphenyl)-5,6-dihydro-4H-pyrrolo[1,2-b]pyrazol-3-yl)quinoxaline. MS m/e: 397 (M+H)±.

Compound 127: 6-(2-(3-Trifluoromethoxyphenyl)-5,6-dihydro-4H-pyrrolo[1,2-b]pyrazol-3-yl)-[1,2,4]triazolo[1,5-a]pyridine. MS m/e: 386 (M+H)±.

Compound 128: 5-(2-(3-Trifluoromethoxyphenyl)-5,6-dihydro-4H-pyrrolo[1,2-b]pyrazol-3-yl)benzo[d]isothiazole. MS m/e: 402 (M+H)±.

Compound 129: 6-(2-(2,3,4-Trifluorophenyl)-5,6-dihydro-4H-pyrrolo[1,2-b]pyrazol-3-yl)-1H-indazole. MS m/e: 355 (M+H)⁺.

Compound 130: 6-(2-(2,3,4-Trifluorophenyl)-5,6-dihydro-4H-pyrrolo[1,2-b]pyrazol-3-yl)imidazo[1,2-a]pyridine. MS m/e: 355 (M+H)⁺.

Compound 131: 6-(2-(2,3,4-Trifluorophenyl)-5,6-dihydro-4H-pyrrolo[1,2-b]pyrazol-3-yl)benzo[d]thiazole. MS m/e: 372 (M+H)±.

Compound 132: 6-(2-(2,3,4-Trifluorophenyl)-5,6-dihydro-4H-pyrrolo[1,2-b]pyrazol-3-yl)quinoxaline. MS m/e: 367 (M+H)±.

Compound 133: 6-(2-(2,3,4-Trifluorophenyl)-5,6-dihydro-4H-pyrrolo[1,2-b]pyrazol-3-yl)-[1,2,4]triazolo[1,5-a]pyridine. MS m/e: 356 (M+H)⁺.

Compound 134: 6-(2-(2-Fluorophenyl)-5,6-dihydro-4H-pyrrolo[1,2-b]pyrazol-3-yl)-1H-indazole. MS m/e: 319 (M+H)±.

Compound 135: 6-(2-(2-Fluorophenyl)-5,6-dihydro-4H-pyrrolo[1,2-b]pyrazol-3-yl)imidazo[1,2-a]pyridine. MS m/e: 319 (M+H)±.

Compound 136: 6-(2-(2-Fluorophenyl)-5,6-dihydro-4H-pyrrolo[1,2-b]pyrazol-3-yl)quinoxaline. MS m/e: 331 (M+H)±.

Compound 137: 6-(2-(2-Fluorophenyl)-5,6-dihydro-4H-pyrrolo[1,2-b]pyrazol-3-yl)-[1,2,4]triazolo[1,5-a]pyridine. MS m/e: 320 (M+H)±.

Compound 138: 5-(2-(3-Chloro-2-fluorophenyl)-5,6-dihydro-4H-pyrrolo[1,2-b]pyrazol-3-yl)-1H-indazole. MS m/e: 353 (M+H)⁺.

Compound 139: 6-(2-(3-Chloro-2-fluorophenyl)-5,6-dihydro-4H-pyrrolo[1,2-b]pyrazol-3-yl)imidazo[1,2-a]pyridine. MS m/e: 353 (M+H)⁺.

Compound 140: 6-(2-(3-Chloro-2-fluorophenyl)-5,6-dihydro-4H-pyrrolo[1,2-b]pyrazol-3-yl)benzo[d]thiazole. MS m/e: 370 (M+H)±.

Compound 141: 6-(2-(3-Chloro-2-fluorophenyl)-5,6-dihydro-4H-pyrrolo[1,2-b]pyrazol-3-yl)-[1,2,4]triazolo[1,5-a]pyridine. MS m/e: 354 (M+H)±.

Compound 142: 5-(2-(3-Chloro-4-fluorophenyl)-5,6-dihydro-4H-pyrrolo[1,2-b]pyrazol-3-yl)-1H-indazole. MS m/e: 353 (M+H)⁺.

Compound 143: 6-(2-(3-Chloro-4-fluorophenyl)-5,6-dihydro-4H-pyrrolo[1,2-b]pyrazol-3-yl)-1H-indazole. MS m/e: 353 (M+H)⁺.

Compound 144: 6-(2-(3-Chloro-4-fluorophenyl)-5,6-dihydro-4H-pyrrolo[1,2-b]pyrazol-3-yl)imidazo[1,2-a]pyridine. MS m/e: 353 (M+H)±.

Compound 145: 6-(2-(3-Chloro-4-fluorophenyl)-5,6-dihydro-4H-pyrrolo[1,2-b]pyrazol-3-yl)benzo[d]thiazole. MS m/e: 370 (M+H)±.

Compound 146: 6-(2-(3-Chloro-4-fluorophenyl)-5,6-dihydro-4H-pyrrolo[1,2-b]pyrazol-3-yl)quinoline. MS m/e: 364 (M+H)±.

Compound 147: 6-(2-(3-Chloro-4-fluorophenyl)-5,6-dihydro-4H-pyrrolo[1,2-b]pyrazol-3-yl)quinoxaline. MS m/e: 365 (M+H)±.

Compound 148: 6-(2-(3-Chloro-4-fluorophenyl)-5,6-dihydro-4H-pyrrolo[1,2-b]pyrazol-3-yl)-[1,2,4]triazolo[1,5-a]pyridine. MS m/e: 354 (M+H)±.

Compound 149: 5-(2-(3-Chloro-4-fluorophenyl)-5,6-dihydro-4H-pyrrolo[1,2-b]pyrazol-3-yl)benzo[d]isothiazole. MS m/e: 370 (M+H)±.

Compound 150: 5-(2-(4-Fluoro-3-trifluoromethoxyphenyl)-5,6-dihydro-4H-pyrrolo[1,2-b]pyrazol-3-yl)-1H-indazole. MS m/e: 403 (M+H)±.

Compound 151: 6-(2-(4-Fluoro-3-trifluoromethoxyphenyl)-5,6-dihydro-4H-pyrrolo[1,2-b]pyrazol-3-yl)imidazo[1,2-a]pyridine. MS m/e: 403 (M+H)±.

Compound 152: 6-(2-(4-Fluoro-3-trifluoromethoxyphenyl)-5,6-dihydro-4H-pyrrolo[1,2-b]pyrazol-3-yl)benzo[d]thiazole. MS m/e: 420 (M+H)±.

Compound 153: 6-(2-(4-Fluoro-3-trifluoromethoxyphenyl)-5,6-dihydro-4H-pyrrolo[1,2-b]pyrazol-3-yl)quinoxaline. MS m/e: 415 (M+H)±.

Compound 154: 6-(2-(4-Fluoro-3-trifluoromethoxyphenyl)-5,6-dihydro-4H-pyrrolo[1,2-b]pyrazol-3-yl)-[1,2,4]triazolo[1,5-a]pyridine. MS m/e: 404 (M+H)±.

Compound 155: 5-(2-(3-Chloro-2,4-difluorophenyl)-5,6-dihydro-4H-pyrrolo[1,2-b]pyrazol-3-yl)-1H-indazole. MS m/e: 371 (M+H)±.

Compound 156: 6-(2-(3-Chloro-2,4-difluorophenyl)-5,6-dihydro-4H-pyrrolo[1,2-b]pyrazol-3-yl)-1H-indazole. MS m/e: 371 (M+H)±.

Compound 157: 6-(2-(3-Chloro-2,4-difluorophenyl)-5,6-dihydro-4H-pyrrolo[1,2-b]pyrazol-3-yl)imidazo[1,2-a]pyridine. MS m/e: 371 (M+H)±.

Compound 158: 6-(2-(3-Chloro-2,4-difluorophenyl)-5,6-dihydro-4H-pyrrolo[1,2-b]pyrazol-3-yl)benzo[d]thiazole. MS m/e: 388 (M+H)±.

Compound 159: 6-(2-(3-Chloro-2,4-difluorophenyl)-5,6-dihydro-4H-pyrrolo[1,2-b]pyrazol-3-yl)quinoxaline. MS m/e: 383 (M+H)±.

Compound 160: 6-(2-(3-Chloro-2,4-difluorophenyl)-5,6-dihydro-4H-pyrrolo[1,2-b]pyrazol-3-yl)-[1,2,4]triazolo[1,5-a]pyridine. MS m/e: 372 (M+H)±.

Compound 161: 5-(2-(2,4-Difluoro-3-methoxyphenyl)-5,6-dihydro-4H-pyrrolo[1,2-b]pyrazol-3-yl)-1H-indazole. MS m/e: 367 (M+H)±.

Compound 162: 6-(2-(2,4-Difluoro-3-methoxyphenyl)-5,6-dihydro-4H-pyrrolo[1,2-b]pyrazol-3-yl)benzo[d]thiazole. MS m/e: 384 (M+H)±.

Compound 163: 6-(2-(2,4-Difluoro-3-methoxyphenyl)-5,6-dihydro-4H-pyrrolo[1,2-b]pyrazol-3-yl)-[1,2,4]triazolo[1,5-a]pyridine. MS m/e: 368 (M+H)⁺.

Compound 164: 6-(2-(2-Fluoro-5-methoxyphenyl)-5,6-dihydro-4H-pyrrolo[1,2-b]pyrazol-3-yl)imidazo[1,2-a]pyridine. MS m/e: 349 (M+H)±.

Compound 165: 6-(2-(2-Fluoro-5-methoxyphenyl)-5,6-dihydro-4H-pyrrolo[1,2-b]pyrazol-3-yl)quinoxaline. MS m/e: 361 (M+H)±.

Compound 166: 6-(2-(2-Fluoro-3-methoxyphenyl)-5,6-dihydro-4H-pyrrolo[1,2-b]pyrazol-3-yl)-[1,2,4]triazolo[1,5-a]pyridine. MS m/e: 350 (M+H)⁺.

Compound 167: 5-(2-(2,4-Difluoro-3-methylphenyl)-5,6-dihydro-4H-pyrrolo[1,2-b]pyrazol-3-yl)-1H-indazole. MS m/e: 351 (M+H)±.

Compound 168: 6-(2-(2,4-Difluoro-3-methylphenyl)-5,6-dihydro-4H-pyrrolo[1,2-b]pyrazol-3-yl)-1H-indazole. MS m/e: 351 (M+H)±.

Compound 169: 6-(2-(2,4-Difluoro-3-methylphenyl)-5,6-dihydro-4H-pyrrolo[1,2-b]pyrazol-3-yl)imidazo[1,2-a]pyridine. MS m/e: 351 (M+H)±.

Compound 170: 6-(2-(2,4-Difluoro-3-methylphenyl)-5,6-dihydro-4H-pyrrolo[1,2-b]pyrazol-3-yl)benzo[d]thiazole. MS m/e: 368 (M+H)±.

Compound 171: 6-(2-(2,4-Difluoro-3-methylphenyl)-5,6-dihydro-4H-pyrrolo[1,2-b]pyrazol-3-yl)quinoline. MS m/e: 362 (M+H)±.

Compound 172: 6-(2-(2,4-Difluoro-3-methylphenyl)-5,6-dihydro-4H-pyrrolo[1,2-b]pyrazol-3-yl)quinoxaline. MS m/e: 363 (M+H)±.

Compound 173: 6-(2-(2,4-Difluoro-3-methylphenyl)-5,6-dihydro-4H-pyrrolo[1,2-b]pyrazol-3-yl)-[1,2,4]triazolo[1,5-a]pyridine. MS m/e: 352 (M+H)±.

Compound 174: 6-(2-(5-Chloro-2-fluorophenyl)-5,6-dihydro-4H-pyrrolo[1,2-b]pyrazol-3-yl)-1H-indazole. MS m/e: 353 (M+H)+.

Compound 175: 6-(2-(5-Chloro-2-fluorophenyl)-5,6-dihydro-4H-pyrrolo[1,2-b]pyrazol-3-yl)benzo[d]thiazole. MS m/e: 370 (M+H)±.

Compound 176: 6-(2-(5-Chloro-2-fluorophenyl)-5,6-dihydro-4H-pyrrolo[1,2-b]pyrazol-3-yl)quinoline. MS m/e: 364 (M+H)±.

Compound 177: 6-(2-(5-Chloro-2-fluorophenyl)-5,6-dihydro-4H-pyrrolo[1,2-b]pyrazol-3-yl)quinoxaline. MS m/e: 365 (M+H)±.

Compound 178: 6-(2-(5-Chloro-2-fluorophenyl)-5,6-dihydro-4H-pyrrolo[1,2-b]pyrazol-3-yl)-[1,2,4]triazolo[1,5-a]pyridine. MS m/e: 354 (M+H)±.

Compound 179: 5-(2-(2,4-Difluoro-5-methylphenyl)-5,6-dihydro-4H-pyrrolo[1,2-b]pyrazol-3-yl)-1H-indazole. MS m/e: 351 (M+H)±.

Compound 180: 6-(2-(2,4-Difluoro-5-methylphenyl)-5,6-dihydro-4H-pyrrolo[1,2-b]pyrazol-3-yl)-1H-indazole. MS m/e: 351 (M+H)±.

Compound 181: 6-(2-(2,4-Difluoro-5-methylphenyl)-5,6-dihydro-4H-pyrrolo[1,2-b]pyrazol-3-yl)imidazo[1,2-a]pyridine. MS m/e: 351 (M+H)±.

Compound 182: 6-(2-(2,4-Difluoro-5-methylphenyl)-5,6-dihydro-4H-pyrrolo[1,2-b]pyrazol-3-yl)benzo[d]thiazole. MS m/e: 368 (M+H)±.

Compound 183: 6-(2-(2,4-Difluoro-5-methylphenyl)-5,6-dihydro-4H-pyrrolo[1,2-b]pyrazol-3-yl)quinoline. MS m/e: 362 (M+H)±.

Compound 184: 6-(2-(2,4-Difluoro-5-methylphenyl)-5,6-dihydro-4H-pyrrolo[1,2-b]pyrazol-3-yl)quinoxaline. MS m/e: 363 (M+H)±.

Compound 185: 6-(2-(2,4-Difluoro-5-methylphenyl)-5,6-dihydro-4H-pyrrolo[1,2-b]pyrazol-3-yl)-[1,2,4]triazolo[1,5-a]pyridine. MS m/e: 352 (M+H)±.

Compound 186: 5-(2-(5-Chloro-2,4-difluorophenyl)-5,6-dihydro-4H-pyrrolo[1,2-b]pyrazol-3-yl)-1H-indazole. MS m/e: 371 (M+H)±.

Compound 187: 6-(2-(5-Chloro-2,4-difluorophenyl)-5,6-dihydro-4H-pyrrolo[1,2-b]pyrazol-3-yl)-1H-indazole. MS m/e: 371 (M+H)±.

Compound 188: 6-(2-(5-Chloro-2,4-difluorophenyl)-5,6-dihydro-4H-pyrrolo[1,2-b]pyrazol-3-yl)imidazo[1,2-a]pyridine. MS m/e: 371 (M+H)±.

Compound 189: 6-(2-(5-Chloro-2,4-difluorophenyl)-5,6-dihydro-4H-pyrrolo[1,2-b]pyrazol-3-yl)benzo[d]thiazole. MS m/e: 388 (M+H)±.

Compound 190: 6-(2-(5-Chloro-2,4-difluorophenyl)-5,6-dihydro-4H-pyrrolo[1,2-b]pyrazol-3-yl)quinoline. MS m/e: 382 (M+H)±.

Compound 191: 6-(2-(5-Chloro-2,4-difluorophenyl)-5,6-dihydro-4H-pyrrolo[1,2-b]pyrazol-3-yl)quinoxaline. MS m/e: 383 (M+H)±.

Compound 192: 6-(2-(5-Chloro-2,4-difluorophenyl)-5,6-dihydro-4H-pyrrolo[1,2-b]pyrazol-3-yl)-[1,2,4]triazolo[1,5-a]pyridine. $^1$H NMR (CDCl$_3$, 300 MHz) δ 8.40 (dd, J=1.8, 0.9 Hz, 1H), 8.32 (s, 1H), 7.67 (dd, J=9.1, 1.0 Hz, 1H), 7.64 (dd, J=8.2, 7.3 Hz, 1H), 7.31 (dd, J=9.1, 1.8 Hz, 1H), 6.89 (t, J=8.9 Hz, 1H), 4.30 (t, J=7.3 Hz, 2H), 3.09 (t, J=7.3 Hz, 2H), 2.75 (p, J=7.3 Hz, 2H). MS m/e: 372 (M+H)±.

Compound 193: 6-(2-(2,5-Difluorophenyl)-5,6-dihydro-4H-pyrrolo[1,2-b]pyrazol-3-yl)-1H-indazole. $^1$H NMR (DMSO-d$_6$, 300 MHz) δ 12.89 (br s, 1H), 8.03 (d, J=0.9 Hz, 1H), 7.69 (dd, J=8.4, 0.8 Hz, 1H), 7.36-7.25 (m, 3H), 7.24 (d, J=0.9 Hz, 1H), 6.97 (dd, J=8.4, 1.4 Hz, 1H), 4.25 (t, J=7.2 Hz, 2H), 3.12 (t, J=7.2 Hz, 2H), 2.68 (p, J=7.3 Hz, 2H). MS m/e: 337 (M+H)±.

Compound 194: 6-(2-(2,5-Difluorophenyl)-5,6-dihydro-4H-pyrrolo[1,2-b]pyrazol-3-yl)imidazo[1,2-a]pyridine. $^1$H NMR (DMSO-d$_6$, 300 MHz) δ 8.84 (dd, J=1.7, 1.0 Hz, 1H), 8.33 (dd, J=0.7 Hz, 1H), 8.20 (d, J=2.1 Hz, 1H), 7.94 (d, J=9.4 Hz, 1H), 7.66 (dd, J=9.4, 1.7 Hz, 1H), 7.43-7.23 (m, 3H), 4.29 (t, J=7.3 Hz, 2H), 3.15 (t, J=7.3 Hz, 2H), 2.71 (p, J=7.3 Hz, 2H). MS m/e: 337 (M+H)±.

Compound 195: 6-(2-(2,5-Difluorophenyl)-5,6-dihydro-4H-pyrrolo[1,2-b]pyrazol-3-yl)benzo[d]thiazole. $^1$H NMR (CD$_3$OD, 300 MHz) δ 9.20 (s, 1H), 7.97 (d, J=8.5 Hz, 1H), 7.89 (d, J=1.8 Hz, 1H), 7.37 (dd, J=8.5, 1.8 Hz, 1H), 7.27-7.07 (m, 3H), 4.30 (t, J=7.3 Hz, 2H), 3.18 (t, J=7.3 Hz, 2H), 2.78 (p, J=7.3 Hz, 2H). MS m/e: 354 (M+H)±.

Compound 196: 6-(2-(2,5-Difluorophenyl)-5,6-dihydro-4H-pyrrolo[1,2-b]pyrazol-3-yl)quinoline. $^1$H NMR (CD$_3$OD, 300 MHz) δ 9.05 (dd, J=5.1, 1.6 Hz, 1H), 8.86 (d, J=8.4 Hz, 1H), 8.10 (d, J=9.1 Hz, 1H), 8.03 (d, J=1.9 Hz, 1H), 7.94-7.89 (m, 2H), 7.36-7.30 (m, 1H), 7.27-7.09 (m, 2H), 4.34 (t, J=7.3 Hz, 2H), 3.27 (t, J=7.3 Hz, 2H), 2.82 (p, J=7.3 Hz, 2H). MS m/e: 348 (M+H)±.

Compound 197: 6-(2-(2,5-Difluorophenyl)-5,6-dihydro-4H-pyrrolo[1,2-b]pyrazol-3-yl)quinoxaline. $^1$H NMR (CD$_3$OD, 300 MHz) δ 8.84 (s, 2H), 8.03 (d, J=8.8 Hz, 1H), 7.87 (d, J=1.8 Hz, 1H), 7.74 (dd, J=8.8, 2.0 Hz, 1H), 7.34-7.28 (m, 1H), 7.26-7.10 (m, 2H), 4.33 (t, J=7.3 Hz, 2H), 3.27 (t, J=7.3 Hz, 2H), 2.82 (p, J=7.3 Hz, 2H). MS m/e: 349 (M+H)±.

Compound 198: 6-(2-(2,5-Difluorophenyl)-5,6-dihydro-4H-pyrrolo[1,2-b]pyrazol-3-yl)-[1,2,4]triazolo[1,5-a]pyridine. $^1$H NMR (CD$_3$OD, 300 MHz) δ 8.62 (dd, J=1.7, 0.9 Hz, 1H), 8.46 (s, 1H), 7.75 (dd, J=9.2, 1.0 Hz, 1H), 7.58 (dd, J=9.2, 1.7 Hz, 1H), 7.33 (dddd, J=8.6, 5.6, 3.1, 0.5 Hz, 1H), 7.25-7.11 (m, 2H), 4.31 (t, J=7.3 Hz, 2H), 3.19 (t, J=7.3 Hz, 2H), 2.79 (p, J=7.3 Hz, 2H). MS m/e: 338 (M+H)±.

Compound 199: 7-(2-(2,5-difluorophenyl)-5,6-dihydro-4H-pyrrolo[1,2-b]pyrazol-3-yl)-2-methoxyquinoxaline $^1$H NMR (DMSO-d$_6$, 300 MHz) 8.49 (s, 1H), 7.88 (d, J=8.4 Hz, 1H), 7.53 (m, 1H), 7.31 (m, 4H), 4.22 (t, J=6.9 Hz, 2H), 3.97 (s, 3H), 3.14 (t, J=7.5 Hz, 2H), 2.64 (m, 2H) ppm; MS m/e: 379.5 (M+H)±.

Compound 200: 7-(2-(2,5-difluorophenyl)-5,6-dihydro-4H-pyrrolo[1,2-b]pyrazol-3-yl)-2-(2-methoxyethoxy)quinoxaline $^1$H NMR (CD$_3$OD, 300 MHz) 8.40 (s, 1H), 7.85 (d, J=8.4 Hz, 1H), 7.59 (m, 1H), 7.41 (dd, J=8.7, 2.1 Hz, 1H), 7.18 (m, 3H), 4.58 (m, 2H), 4.28 (t, J=7.2 Hz, 2H), 3.81 (m, 2H), 3.42 (s, 3H), 3.20 (t, J=7.5 Hz, 2H), 2.76 (m, 2H) ppm; MS m/e: 423.5 (M+H)±.

Compound 201: 6-(2-(2-fluorophenyl)-5,6-dihydro-4H-pyrrolo[1,2-b]pyrazol-3-yl)benzo[d]thiazole.

Example 2: AlphaScreen® SureFire® SMAD3 (p-Ser423/425) Assay

The p-SMAD-3 (Ser423/425) SureFire® assay has been designed to measure the phosphorylation of endogenous cellular p-SMAD-3 (Ser423/425) in cell lysates and is a system for the screening of both modulators of receptor activation (e.g. agonists and antagonists) as well as agents acting intracellularly, such as small molecule inhibitors of upstream events. The assay will measure p-SMAD-3 (Ser423/425) activation by either cloned or endogenous receptors, and can be applied to primary cells.

1× Lysis buffer: 1 ml of 5× Lysis buffer was diluted with 4 ml of sterile water. After dilution, excess 1× Lysis buffer can be frozen and thawed up to 5 times without loss in activity.

P-SMAD-3 (Ser423/425) SureFire® Assay Protocols

Step A: Preparation of Buffers

Activation buffer: The buffer was warmed slowly to 37° C. and gently mixed to re-suspend. Activation buffer can be stored at room temperature with no loss in activity.

Reaction buffer: The buffer was kept at 4° C. while in use.

AlphaScreen® Protein A IgG Kit: The kit was stored at 4° C. in the dark.

Reaction buffer+Activation buffer+AlphaScreen® Acceptor beads: Reaction buffer (40 parts), Activation Buffer (10 parts) and Acceptor beads (1 part) were mixed and the mixture was stored at room temperature and used the same day. Mixture was added to 384-well plates; excess mixture was discarded.

Dilution buffer+AlphaScreen® Donor beads: Dilution buffer (20 parts) and Donor beads (1 part) were mixed and the mixture was stored at room temperature and used the same day. Excess mixture was discarded.

Assay control samples: After reconstitution in 250 µl of water, lysates were at −20° C. in single use aliquots.

Step B: Preparation of Samples and Cells 96-well Assay Protocol for 293FT and RMS13 adherent cells can be carried out manually or in high throughput with liquid handling robots.

The cells (80 µL of cells for 96 well plates) were plated in collagen coated tissue culture plates in RPMI or FreeStyle medium (Invitrogen) and incubated overnight. For manual analysis, 6 plates for GDF8, 6 plates for TGFβ, and optionally 6 plates for Alk5ca(ALK5 constitutively active) were used.

The compound dilution plates were prepared as follows: 12 µL of DMSO was transferred into first column of 96-well plate, and 16 µL of DMSO was transferred into columns 2-12 of the 96-well plate. 12 µL of compound solution was transferred into first column of the DMSO-containing 96-well plate. Three-fold dilution was performed up to column 10 of the DMSO-containing 96-well plate.

Step C: Treatment and Analysis

The plate containing cells were treated with compounds for about 10 minutes, and then ligand was added. GDF8 or TGFb was added to plates to stimulate. 293FL cells were stimulated for 90 minutes at 37° C.; and RMS13 cells were stimulated for 60 minutes at 37° C. The medium was then removed from the cells, and 1× Lysis Buffer (about 25 µL) was added and the plate was gently agitated on plate shaker for 5-10 minutes.

The lysate (5 µL) was then placed into 384-well shallow plates avoiding the generation of bubbles. To this, the Reaction Buffer+Activation Buffer+AlphaScreen® Acceptor beads mixture (5 µL) was added. The plate was sealed with adhesive cover and shielded from light (e.g., with metal foil), and agitated gently on plate shaker for 2 hours at room temperature.

Dilution buffer+AlphaScreen® Donor beads (2 µL) was then added, and the plate was intubated on the plate shaker for an additional 1½ hours. After completion, the plate was read on Synergy-4 or Enspire plate reader, using AlphaScreen® pSMAD3® settings.

Representative results for inhibition of GDF8 (data=GDF pSMAD (MPC11) (µM)) and TGF-β (data=TGF-β pSMAD (MPC-11) (µM)) signaling are shown in Table 1 (A=<0.1 µM, B=0.1–<0.5 µM, C=0.5–<1.0 µM, D=1.0-10.0 µM, E=10 µM):

| No. | GDF8 | TGF-β |
|---|---|---|
| 1 | C | D |
| 2 | A | B |
| 3 | A | B |
| 4 | C | D |
| 5 | B | B |
| 6 | B | 1.04 |
| 7 | A | A |
| 8 | A | A |
| 9 | A | B |
| 10 | C | D |
| 11 | A | B |
| 12 | A | B |
| 13 | A | B |
| 14 | B | C |
| 15 | C | D |
| 16 | A | B |
| 17 | B | B |
| 18 | A | B |
| 19 | B | D |
| 20 | B | B |
| 21 | B | D |
| 22 | A | B |
| 23 | B | B |
| 24 | A | A |
| 25 | A | B |
| 26 | A | B |
| 27 | B | C |
| 28 | A | B |
| 29 | B | B |
| 30 | A | B |
| 31 | A | B |
| 32 | A | B |
| 33 | A | A |
| 34 | A | A |
| 35 | A | B |
| 36 | B | C |
| 37 | A | B |
| 38 | A | A |
| 39 | A | B |
| 40 | C | D |
| 41 | A | B |
| 42 | B | B |
| 43 | B | C |
| 44 | A | B |
| 45 | D | E |
| 46 | B | D |
| 47 | B | D |
| 48 | C | D |
| 49 | B | C |
| 50 | B | D |
| 51 | B | D |
| 52 | A | B |
| 53 | B | D |
| 54 | A | B |
| 55 | B | C |
| 56 | B | C |
| 57 | A | B |
| 58 | B | C |
| 59 | B | C |

| No. | GDF8 | TGF-β |
|-----|------|-------|
| 60 | A | B |
| 61 | B | B |
| 62 | B | C |
| 63 | D | D |
| 64 | B | D |
| 65 | B | C |
| 66 | A | B |
| 67 | B | D |
| 68 | B | D |
| 69 | D | D |
| 70 | B | D |
| 71 | B | C |
| 72 | B | C |
| 73 | B | D |
| 74 | B | D |
| 75 | D | D |
| 76 | B | C |
| 77 | B | D |
| 78 | C | D |
| 79 | B | B |
| 80 | C | D |
| 81 | B | D |
| 82 | B | D |
| 83 | A | C |
| 84 | B | D |
| 85 | B | B |
| 86 | B | C |
| 87 | B | D |
| 88 | D | D |
| 89 | B | D |
| 90 | C | D |
| 91 | B | C |
| 92 | B | D |
| 93 | A | B |
| 94 | A | B |
| 95 | C | D |
| 96 | B | C |
| 97 | A | B |
| 98 | B | C |
| 99 | B | D |
| 100 | C | D |
| 101 | D | E |
| 102 | C | D |
| 103 | B | C |
| 104 | A | A |
| 105 | A | B |
| 106 | B | C |
| 107 | A | B |
| 108 | A | B |
| 109 | B | C |
| 110 | B | C |
| 111 | A | B |
| 112 | B | C |
| 113 | B | D |
| 114 | A | A |
| 115 | A | B |
| 116 | A | B |
| 117 | B | D |
| 118 | A | C |
| 119 | A | B |
| 120 | C | D |
| 121 | B | C |
| 122 | A | A |
| 123 | A | B |
| 124 | A | A |
| 125 | B | B |
| 126 | B | B |
| 127 | A | A |
| 128 | B | C |
| 129 | B | D |
| 130 | B | D |
| 131 | B | C |
| 132 | C | D |
| 133 | B | C |
| 134 | C | D |
| 135 | C | D |
| 136 | C | D |
| 137 | B | C |
| 138 | C | D |
| 139 | B | C |
| 140 | C | C |
| 141 | B | C |
| 142 | B | B |
| 143 | B | C |
| 144 | B | B |
| 145 | B | C |
| 146 | D | D |
| 147 | B | C |
| 148 | A | B |
| 149 | C | D |
| 150 | B | D |
| 151 | B | D |
| 152 | B | D |
| 153 | C | D |
| 154 | B | C |
| 155 | B | D |
| 156 | B | D |
| 157 | B | C |
| 158 | A | C |
| 159 | C | D |
| 160 | B | C |
| 161 | C | D |
| 162 | C | D |
| 163 | B | D |
| 164 | C | D |
| 165 | A | A |
| 166 | B | C |
| 167 | B | C |
| 168 | B | C |
| 169 | B | B |
| 170 | B | C |
| 171 | D | D |
| 172 | C | D |
| 173 | B | B |
| 174 | A | B |
| 175 | A | A |
| 176 | A | B |
| 177 | A | A |
| 178 | A | A |
| 179 | B | C |
| 180 | C | D |
| 181 | B | B |
| 182 | B | B |
| 183 | B | D |
| 184 | B | B |
| 185 | A | A |
| 186 | B | B |
| 187 | B | C |
| 188 | A | A |
| 189 | B | B |
| 190 | B | C |
| 191 | A | B |
| 192 | A | A |
| 193 | B | D |
| 194 | B | C |
| 195 | A | B |
| 196 | C | D |
| 197 | A | C |
| 198 | A | B |
| 199 | B | D |
| 200 | B | C |
| 201 | B | D |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:
1. A compound having the structure of formula (I):

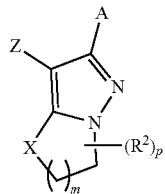

or a pharmaceutically acceptable salt, prodrug or N-oxide thereof, or solvate or hydrate thereof,
wherein
m is 1 or 2;
p is 0 or 1;
X is —CH$_2$— or —O—;
A is

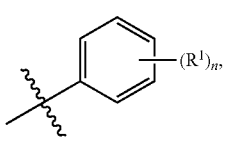

n is 0, 1, 2, 3, 4, or 5;
wherein each R$^1$ is independently halogen, —C$_1$-C$_6$alkyl, —C$_1$-C$_6$haloalkyl, —C$_1$-C$_6$alkoxy, —C$_1$-C$_6$haloalkoxy, C$_{3-8}$Cak(C$_{0-6}$alkyl), Hca(C$_{0-6}$alkyl), Ar(C$_{0-6}$alkyl), Het(C$_{0-6}$alkyl), —O—(C$_0$-C$_6$alkyl)-Ar, —O—(C$_0$-C$_6$alkyl)-Het, —O—(C$_0$-C$_6$alkyl)-Cak, —O—(C$_0$-C$_6$alkyl)-Hca, —NO$_2$, or —CN, wherein the Ar, Het, Cak, Hca, and alkyl are optionally substituted with 1, 2, 3, or 4 groups that are each independently halogen, cyano, nitro, —OR$^a$, —SR$^a$, —NR$^a_2$, —C(O)OR$^a$, —C(O)NR$^a_2$, —C(O)R$^a$, —S(O)R$^a$, —S(O)$_2$R$^a$, —S(O)OR$^a$, —S(O)$_2$OR$^a$, —S(O)NR$^a_2$, —S(O)$_2$NR$^a_2$, —OC(O)R$^a$, —OC(O)OR$^a$, —OC(O)NR$^a_2$, —N(R)C(O)R$^a$, —N(R)C(O)OR$^a$, —N(R)C(O)NR$^a_2$, —N(R)S(O)R$^a$, —N(R$^a$)S(O)$_2$R$^a$, C$_1$-C$_6$alkyl, or C$_1$-C$_6$haloalkyl;
each R$^a$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano; or

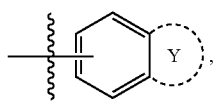

wherein the Y ring is a 5- to 9-membered Hca optionally substituted by halo or C$_1$-C$_6$alkyl;
each R$^2$ is independently halogen, C$_1$-C$_6$alkyl, C$_1$-C$_6$haloalkyl, —OR$^c$, —SR$^c$, —NR$^c_2$, C$_{3-8}$Cak, —NO$_2$ or —CN, wherein each R$^c$ is independently hydrogen, C$_1$-C$_6$alkyl, or C$_1$-C$_6$haloalkyl; and Z is a fused bicyclic ring of the formula,

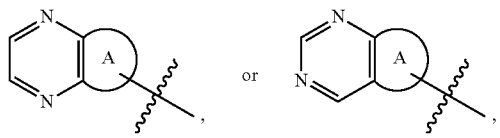

wherein
ring A is Ar or 5- or 6-membered Het,
wherein
Z is optionally substituted by one or two —R$^Z$ groups that are each independently halogen, cyano, C$_{1-6}$alkyl, C$_{1-6}$haloalkyl, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)S(O)$_2$R, —O—C$_{1-6}$alkyl-OR, —O—C$_{1-6}$alkyl-SR, —O—C$_{1-6}$alkyl-NR$_2$, or C$_{3-8}$Cak wherein each Cak and alkyl group is optionally substituted by one or two —R$^{Z2}$ groups;
wherein each —R$^{Z2}$ is independently halogen, cyano, C$_{1-6}$alkyl, C$_{1-6}$haloalkyl, —C$_1$-C$_6$alkoxy, —OR$^b$, —NR$^b_2$, —C(O)R$^b$, —C(O)OR$^b$, —C(O)NR$^b_2$, —S(O)$_2$NR$^b_2$, or —S(O)$_2$R$^b$;
each R is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, and alkyl are optionally substituted with C$_1$-C$_6$alkyl, halogen, or C$_1$-C$_6$haloalkyl; and
each R$^b$ is independently hydrogen or C$_1$-C$_6$alkyl.

2. The compound of claim 1, wherein A is:

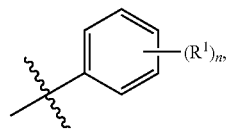

wherein n is 0, 1, 2, or 3; or

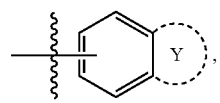

wherein the Y ring is a 5- to 7-membered Hca optionally substituted by halo or C$_1$-C$_6$alkyl.
3. The compound of claim 1, wherein n is 1 or 2.
4. The compound of claim 1, wherein n is 1.
5. The compound of claim 1, wherein n is 2.
6. The compound of claim 1, wherein n is 0.
7. The compound of claim 1, wherein p is 1.
8. The compound of claim 1, wherein p is 0.
9. The compound of claim 1, wherein each R$^2$ is independently halogen, C$_1$-C$_6$alkyl, C$_1$-C$_6$haloalkyl, or —OR$^c$.
10. The compound of claim 1, wherein m is 1.
11. The compound of claim 1, wherein m is 2.

12. The compound of claim 1, which is of the formula:

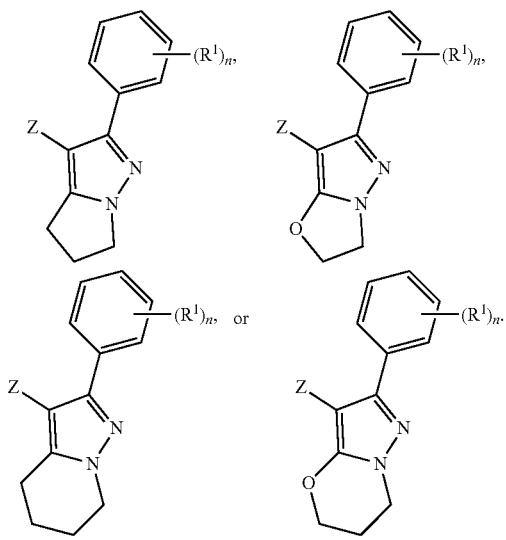

13. A method for treating a disease or condition mediated by or involving a member of the TGF-β receptor superfamily in a subject in need thereof, comprising administering an effective TGF-β receptor superfamily inhibiting amount of a compound according to claim 1.

14. The method of claim 13, wherein the disease or condition is pulmonary hypertension, chronic renal disease, acute renal disease, wound healing, arthritis, osteoporosis, kidney disease, congestive heart failure, ulcer, ocular disorder, corneal wound, diabetic nephropathy, impaired neurological function, Alzheimer's disease, atherosclerosis, peritoneal or sub-dermal adhesion, kidney fibrosis, lung fibrosis, idiopathic pulmonary fibrosis, liver fibrosis, hepatitis B, hepatitis C, alcohol-induced hepatitis haemochromatosis, primary biliary cirrhosis, restenosis, retroperitoneal fibrosis, mesenteric fibrosis, endometriosis, keloids, cancer, abnormal bone function, inflammatory disorder, scarring or photoaging of the skin; or wherein the disease or condition is benign or malignant tumor, carcinoma of the brain, kidney, liver, adrenal gland, bladder, breast, stomach, gastric tumors, ovaries rectum, prostate, pancreas, lung, vagina or thyroid, sarcoma, glioblastomas, multiple myeloma or gastrointestinal cancer, colon carcinoma or colorectal adenoma, tumor of the neck and head, epidermal hyperproliferation, melanoma, psoriasis, prostate hyperplasia, neoplasia, neoplasia of epithelial character, leukemias, lymphomas, mammary carcinoma or leukemia; or the disease or condition is Cowden syndrome, Lhermitte-Dudos disease, Bannayan-Zonana syndrome, or other disease in which the PI3K/PKB pathway is aberrantly activated.

15. A method for treating cancer in which TGF-β signaling is implicated in a subject in need thereof, comprising administering an effective GDF-8 or TGF-β inhibiting amount of a compound according to claim 1 in combination with the administration of a therapeutically effective amount of one or more chemotherapeutic agents.

16. The method of claim 15, wherein the one or more chemotherapeutic agents is independently selected from the group consisting of antimetabolites, alkylating agents, coordination compounds, platinum complexes, DNA cross-linking compounds, inhibitors of transcription enzymes, tyrosine kinase inhibitors, protein kinase inhibitors, topoisomerase inhibitors, DNA minor-groove binding compounds, vinca alkyloids, taxanes, antitumor antibiotics, hormones, aromatase inhibitors, enzymes, growth factor receptors antibodies, cytokines, cell surface markers antibodies, HDAC inhibitors, HSP 90 inhibitors, BCL-2 inhibitors, B-raf inhibitors, MEK inhibitors, mTOR inhibitors, proteasome inhibitors and monoclonal antibodies; or wherein the one or more chemotherapeutic agents is independently selected from the group consisting of ABT-199, mechlorothamine, cyclophosphamide, ifosfamide, melphalan, chlorambucil, ethyleneimines, methylmelamines, procarbazine, dacarbazine, temozolomide, busulfan, carmustine, lomustine, methotrexate, fluorouracil, capecitabine, cytarabine, gemcitabine, cytosine arabinoside, mecaptopurine, fludarabine, cladribine, thioguanine, azathioprine, vinblastine, vincristine, paclitaxel, docetaxel, colchicine, actinomycin D, daunorubicin, bleomycin, L-asparaginase, cisplatin, carboplatin, oxaliplatin, prednisone, dexamethasone, amino glutethimide, formestane, anastrozole, hydroxyprogesterone caproate, medroxyprogesterone, tamoxifen, amsacrine, mitoxantrone, topotecan, irinotecan, camptothecin, afatinib, axitinib, bosutinib, bortezomib, carfilzomib, cabozantinib, cediranib, crizotinib, dasatinib, dabrafenib, evorolimus, ibrutinib, LDK378, LGX818, MEK162, regorafenib, ruxolitinib, selumetinib, sorafenib, trametinib, vemurafenib, erlotinib, gefitinib, imatinib, lapatinib, lestaurtinib, nilotinib, palbociclib, pazopanib, pomatinib, semaxanib, sirolimus, sunitinib, temsirolimus, vatalanib, vandetanib, anti Her2 antibodies, interferon-α, interferon-γ, interleukin 2, GM CSF, anti CTLA 4 antibodies, rituximab, anti CD33 antibodies, MGCD0103, vorinostat, 17-AAG, thalidomide, lenalidomide, rapamycin, CCI-779, doxorubicine, gemcitabine, melphalan, NPI052, gemtuzumab, alemtuzumab, cetuximab, ibritumomab tiuxaetan, tositumomab, iodine-131 tositumomab, trastuzumab, ado-trastuzumab emtansine, obinutuzumab, bevacizumab, rituximab, and anti-TRAIL death receptor antibodies.

* * * * *